(12) United States Patent
Helliwell et al.

(10) Patent No.: US 7,732,660 B2
(45) Date of Patent: Jun. 8, 2010

(54) METHODS AND MEANS FOR PRODUCING EFFICIENT SILENCING CONSTRUCT USING RECOMBINATIONAL CLONING

(75) Inventors: Christopher A. Helliwell, Canberra (AU); Susan V. Wesley, Ongole (IN); Peter M. Waterhouse, Newtown (AU)

(73) Assignee: Commonwealth Scientific and Industrial Research Corporation, Campbell (AU)

( * ) Notice: Subject to any disclaimer, the term of this patent is extended or adjusted under 35 U.S.C. 154(b) by 889 days.

(21) Appl. No.: 11/034,069

(22) Filed: Jan. 13, 2005

(65) Prior Publication Data

US 2005/0164394 A1 Jul. 28, 2005

(51) Int. Cl.
*C12N 15/82* (2006.01)
*C12N 15/87* (2006.01)

(52) U.S. Cl. .................................. 800/278; 800/295
(58) Field of Classification Search ............... 800/278, 800/295
See application file for complete search history.

(56) References Cited

FOREIGN PATENT DOCUMENTS

| WO | WO 96/40724 | 12/1996 |
|---|---|---|
| WO | WO 98/53083 | 11/1998 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 00/01846 | 1/2000 |
| WO | WO 00/44914 | 8/2000 |
| WO | WO 00/49035 | 8/2000 |

OTHER PUBLICATIONS

Opalinska et al. (Nature Reviews, 2002, 1:503-514).*
P.M. Waterhouse et al., "Virus Resistance and Gene Silencing in Plants can be Induced by Simultaneous Expression of Sense and Antisense RNA," *Proc. Natl. Acad. Sci. USA*, (Nov. 1998) pp. 13959-13964, vol. 95, National Academy of Science, Washington, D.C. USA.
J.Z. Levin, et al., "Methods of Double-Stranded RNA-Mediated Gene Inactivation in *Arabidopsis* and Their Use to Define an Essential Gene in Methionine Biosynthesis", *Plant Molecular Biology*, (Dec. 2000) pp. 759-775, vol. 44, No. 6, Nijhoff Publishers, Dordrecht, NL.
J.L. Hartley et al., "DNA Cloning Using in vitro Site-Specific Recombination" *Genome Research*, (Nov. 2000), pp. 1788-1795, vol. 10, No. 11, Cold Spring Harbor Laboratory Press, US.
A.J.M. Walhout et al., "Gateway Recombinational Cloning: Application to the Cloning of Large Numbers of Open Reading Frames or ORFeomes", *Methods in Enzymology*, (2000), pp. 575-592, vol. 328, Academic Press Inc., San Diego, CA, US.
L. Qinghua et al., "The Univector Plasmid-Fusion System a Method for Rapid Construction of Recombinant DNA Without Restriction Enzymes", *Current Biology*, (Dec. 1998) pp. 1300-1309, vol. 8, No. 4, Current Science, GB.
N. Tavernarakis et al., "Heritable and Inducible Genetic Interference by Double-Stranded RNA Encoded by Transgenes", *Nature Genetics*, (Feb. 2000), pp. 180-183, vol. 24, Nature America, New York, US.

(Continued)

*Primary Examiner*—J. E Angell
(74) *Attorney, Agent, or Firm*—Buchanan, Ingersoll & Rooney, PC

(57) ABSTRACT

Methods and vectors and kits are provided for producing chimeric nucleic acid constructs capable of producing dsRNA for silencing target nucleic acid sequences of interest using recombinational cloning.

21 Claims, 6 Drawing Sheets

OTHER PUBLICATIONS

L. Timmons et al., "Specific Interference by Ingested dsRNA", *Nature*, (Oct. 1998), p. 854, vol. 395, No. 6705, MacMillan Journals Ltd., London, GB.

A. Fire, "RNA-triggered Gene Silencing", *Trends in Genetics*, (Sep. 1999), pp. 358-363, vol. 15, No. 9, Elsevier Science Publishers B.V. Amsterdam, NL.

C. Helliwell et al., "Constructs and Methods for High-Throughput Gene Silencing in Plants", *Methods: A Companion to Methods in Enzymology*, (Aug. 2003), pp. 2003-2008, vol. 30, No. 4, Academic Press Inc., NY, NY, US.

AzpiroLeehan and Feldmann "T-DNA Insertion Mutagenesis in *Arabidopsis*: Going Back and Forth" (1997) *Trends Genet.* 13:152-156.

Fire et al. "Potent and Specific Genetic Interference by Double-Stranded RNA in *Caenorhabditis elegans*" (1998) *Nature* 391:806-811.

Hamilton et al. "A Transgene With Repeated DNA Causes High Frequency, Post-transcriptional Suppression of ACC-oxidase Gene Expression in Tomato" (1998) *Plant J.* 15:737-746.

Hoess et al. "The Role of the *loxP* Spacer Region in P1 Site-Specific Recombination" (1986) *Nucl. Acids Res.* 14:2287.

Landy "Dynamic, Structural, and Regulatory Aspects of λ Site-Specific Recombination" (1989) *Ann. Rev. Biochem.* 58:913.

Martienssen "Functional Genomics: Probing Plant Gene Function and Expression with Transposons"(1998) *Proc. Natl. Acad. Sci. USA* 95:2021-2026.

Montgomery et al. "Double-Stranded RNA as a Mediator in Squence-Specific Genetic Silencing and Co-Suppression" (1998) *Trends in Genetics* 14:255-258.

Ross-MacDonald et al. "Large-Scale Analysis of the Yeast Genome by Transposon Tagging and Gene Disruption" (1999) *Nature* 402:413-418.

Smith et al. "Total Silencing by Intron-Spliced Hairpin RNAs" (2000) *Nature* 407:319-320.

Wagner and Sun"Double-Stranded RNA Poses Puzzle" (1998) *Nature* 391:744-745.

Waterhouse et al. "Virus Resistance and Gene Silencing in Plants Can be Induced by Simultaneous Expression of Sense and Antisense RNA" (1998) *Proc. Natl. Acad. Sci. USA* 95:13959-13964.

Wesley et al. "Construct Design for Efficient, Effective and High-Throughput Gene Silencing in Plants" (2001) *The Plant Journal* 27(6):581-590.

* cited by examiner

METHODS AND MEANS FOR PRODUCING EFFICIENT SILENCING CONSTRUCT USING RECOMBINATIONAL CLONING

CROSS-REFERENCE TO RELATED APPLICATIONS

This application claims priority to U.S. application Ser. No. 10/055,001, filed Jan. 25, 2002, and from U.S. Provisional Application Ser. No. 60/264, 067, filed Jan. 25, 2001 and U.S. Provisional Application Ser. No. 60/333,743, filed Nov. 29, 2001. The entire content of these prior applications is incorporated herein by reference.

FIELD OF THE INVENTION

This invention relates to efficient methods and means for producing chimeric nucleic acid constructs capable of producing dsRNA useful for silencing target nucleic acid sequences of interest. The efficiency of the disclosed methods and means further allows high throughput analysis methods to determine the function of isolated nucleic acids, such as ESTs, without a known function and may further be put to use to isolate particular genes or nucleotide sequences from a preselected group of genes.

BACKGROUND ART

Increasingly, the nucleotide sequence of whole genomes of organisms, including *Arabidopsis thaliana*, has been determined and as these data become available, they provide a wealth of unmined information. The ultimate goal of these genome projects is to identify the biological function of every gene in the genome.

Attribution of a function to a nucleic acid with a particular nucleotide sequence can be achieved in a variety of ways. Some of the genes have been characterized directly using the appropriate assays. Others have been attributed with a tentative function through homology with (parts of) genes having a known function in other organisms. Loss-of-function mutants, obtained e.g. by tagged insertional mutagenesis have also been very informative about the role of some of these unknown genes (AzpiroLeehan and Feldmann 1997; Martienssen 1998) particularly in the large-scale analysis of the yeast genome (Ross-MacDonald et al., 1999).

Structural mutants resulting in a loss-of-function may also be mimicked by interfering with the expression of a nucleic acid of interest at the transcriptional or post-transcriptional level. Silencing of genes, particularly plant genes using antisense or co-suppression constructs to identify gene function, especially for a larger number of targets, is however hampered by the relatively low proportion of silenced individuals obtained, particularly those wherein the silencing level is almost complete.

Recent work has demonstrated that the silencing efficiency could be greatly improved both on quantitative and qualitative level using chimeric constructs encoding RNA capable of forming a double stranded RNA by basepairing between the antisense and sense RNA nucleotide sequences respectively complementary and homologous to the target sequences.

Fire et al., 1998 describe specific genetic interference by experimental introduction of double-stranded RNA in *Caenorhabditis elegans*. The importance of these findings for functional genomics has been discussed (Wagner and Sun, 1998).

WO 99/32619 provides a process of introducing RNA into a living cell to inhibit gene expression of a target gene in that cell. The process may be practiced ex vivo or in vivo. The RNA has a region with double-stranded structure. Inhibition is sequence-specific in that the nucleotide sequences of the duplex region of the RNA and or a portion of the target gene are identical.

Waterhouse et al. 1998 describes that virus resistance and gene silencing in plants can be induced by simultaneous expression of sense and anti-sense RNA. The sense and anti-sense RNA may be located in one transcript that has self-complementarity.

Hamilton et al. 1998 describes that a transgene with repeated DNA, i.e. inverted copies of its 5' untranslated region, causes high frequency, post-transcriptional suppression of ACC-oxidase expression in tomato.

WO 98/53083 describes constructs and methods for enhancing the inhibition of a target gene within an organism, which involve inserting into the gene-silencing vector an inverted, repeat sequence of all or part of a polynucleotide region within the vector.

WO 99/53050 provides methods and means for reducing the phenotypic expression of a nucleic acid of interest in eukaryotic cells, particularly in plant cells. These methods involve introducing chimeric genes encoding sense and anti-sense RNA molecules directed towards the target nucleic acid, which are capable of forming a double stranded RNA region by base-pairing between the regions with the sense and antisense nucleotide sequence, or introducing the RNA molecules themselves. Preferably, the RNA molecules comprise simultaneously both sense and antisense nucleotide sequences.

WO 99/49029 relates generally to a method of modifying gene expression and to synthetic genes for modifying endogenous gene expression in a cell, tissue or organ of a transgenic organism, in particular to a transgenic animal of plant. Synthetic genes and genetic constructs, capable of forming a dsRNA which are capable of repressing, delaying or otherwise reducing the expression of an endogenous gene or a target gene in an organism when introduced thereto are also provided.

WO 99/61631 relates to methods to alter the expression of a target gene in a plant using sense and antisense RNA fragments of the gene. The sense and antisense RNA fragments are capable of pairing and forming a double-stranded RNA molecule, thereby altering the expression of the gene. The present invention also relates to plants, their progeny and seeds thereof obtained using these methods.

WO 00/01846 provides a method of identifying DNA responsible for conferring a particular phenotype in a cell. That method comprises a) constructing a cDNA or genomic library of the DNA of the cell in a suitable vector in an orientation relative to (a) promoter(s) capable of initiating transcription of the cDNA or DNA to double stranded (ds) RNA upon binding of an appropriate transcription factor to the promoter(s); b) introducing the library into one or more of cells comprising the transcription factor, and c) identifying and isolating a particular phenotype of a cell comprising the library and identifying the DNA or cDNA fragment from the library responsible for conferring the phenotype. Using this technique, it is also possible to assign function to a known DNA sequence by a) identifying homologues of the DNA sequence in a cell, b) isolating the relevant DNA homologue(s) or a fragment thereof from the cell, c) cloning the homologue or fragment thereof into an appropriate vector in an orientation relative to a suitable promoter capable of initiating transcription of dsRNA from said DNA homologue or fragment upon binding of an appropriate transcription factor to the promoter and d) introducing the vector into the cell from step a) comprising the transcription factor.

WO 00/44914 also describes composition and methods for in vivo and in vitro attenuation of gene expression using double stranded RNA, particularly in zebrafish.

WO 00/49035 discloses a method for silencing the expression of an endogenous gene in a cell. That method involves overexpressing in the cell a nucleic acid molecule of the endogenous gene and an antisense molecule including a nucleic acid molecule complementary to the nucleic acid molecule of the endogenous gene, wherein the overexpression of the nucleic acid molecule of the endogenous gene and the antisense molecule in the cell silences the expression of the endogenous gene.

Smith et al., 2000 as well as WO 99/53050 described that intron containing dsRNA further increased the efficiency of silencing.

However, the prior art has not solved the problems associated with the efficient conversion of any nucleotide sequence of interest into a chimeric construct capable of producing a dsRNA in eukaryotic cells, particularly in plant cells, and preferably in a way amenable to the processing of large number of nucleotide sequences.

These and other problems have been solved as described hereinafter in the different embodiments and claims.

SUMMARY OF THE INVENTION

It is an object of the invention to provide vectors comprising the following operably linked DNA fragments a) an origin of replication allowing replication in microorganisms (1), preferably bacteria; particularly *Escherichia coli*; b) a selectable marker region (2) capable of being expressed in microorganisms, preferably bacteria; and c) a chimeric DNA construct comprising in sequence (i) a promoter or promoter region (3) capable of being recognized by RNA polymerases of a eukaryotic cell, preferably a plant-expressible promoter; (ii) a first recombination site (4), a second recombination site (5), a third recombination site (6) and a fourth recombination site (7); and (iii) a 3' transcription terminating and polyadenylation region (8) functional in the eukaryotic cell; wherein the first recombination site (4) and the fourth recombination site (7) are capable of reacting with a same recombination site, preferably are identical, and the second recombination site (5) and the third recombination site (6), are capable of reacting with a same recombination site, preferably are identical; and wherein the first recombination site (4) and the second recombination site (5) do not recombine with each other or with a same recombination site or the third recombination site (6) and the fourth recombination site (7) do not recombine with each other or with a same recombination site. Optionally the vector may further include additional elements such as: a second selectable marker gene (9) between the first (4) and second recombination site (5) and/or a third selectable marker gene (10) between the third (6) and fourth recombination site (7) and/or a region flanked by intron processing signals (11), preferably an intron, functional in the eukaryotic cell, located between the second recombination site (5) and the third recombination site (6) and/or a fourth selectable marker gene (19), located between the second (5) and third recombination site (6) and/or left and right border T-DNA sequences flanking the chimeric DNA construct and/or a selectable marker gene capable of being expressed in eukaryotic, preferably plant, cells, preferably located between the left and the right T-DNA border sequences and/or an origin of replication capable of functioning in *Agrobacterium* spp. Selectable marker genes may be selected from the group consisting of an antibiotic resistance gene, a tRNA gene, an auxotrophic marker, a toxic gene, a phenotypic marker, an antisense oligonucleotide; a restriction endonuclease; a restriction endonuclease cleavage site, an enzyme cleavage site, a protein binding site, an sequence complementary PCR primer. Preferably the first (4) and fourth recombination site (7) are attR1 comprising the nucleotide sequence of SEQ ID No 4 and the second (5) and third (6) recombination site are attR2 comprising the nucleotide sequence of SEQ ID No 5 or the first (4) and fourth recombination site (7) are attP1 comprising the nucleotide sequence of SEQ ID No 10 and the second (5) and third (6) recombination site are attP2 comprising the nucleotide sequence of SEQ ID No 11.

It is another objective of the invention to provide a kit comprising an acceptor vector according to invention, preferably further comprising at least one recombination protein capable of recombining a DNA segment comprising at least one of the recombination sites.

It is yet another objective of the invention to provide a method for making a chimeric DNA construct capable of expressing a dsRNA in a eukaryotic cell comprising the steps of combining in vitro:

an acceptor vector as herein before described;
an insert DNA, preferably a linear or circular insert DNA, comprising
  a DNA segment of interest (12) flanked by
  a fifth recombination site (13) which is capable of recombining with the first (4) or fourth recombination site (7) on the vector; and
  a sixth recombination site (14) which is capable of recombining with the second (5) or third recombination site (6) on the vector;
at least one site specific recombination protein capable of recombining the first (4) or fourth (7) and the fifth recombination site (13) and the second (5) or third (6) and the sixth recombination site (14);
allowing recombination to occur in the presence of at least one recombination protein, preferably selected from Int and IHF and (ii) Int, Xis, and IHF, so as to produce a reaction mixture comprising product DNA molecules, the product DNA molecule comprising in sequence:
  the promoter or promoter region (3) capable of being recognized by RNA polymerases of the eukaryotic cell;
  a recombination site (15) which is the recombination product of the first (4) and the fifth recombination site (13);
  the DNA fragment of interest (12);
  a recombination site (16) which is the recombination product of the second (4) and the sixth recombination site (14);
  a recombination site (17) which is the recombination product of the third (5) and the sixth recombination site (14);
  the DNA fragment of interest in opposite orientation (12);
  a recombination site (18) which is the recombination product of the fourth (7) and the fifth recombination site (13); and
  the 3' transcription terminating and polyadenylation region (8) functional in the eukaryotic cell; and
selecting the product DNA molecules, preferably in vivo.

The method allows that multiple insert DNAs comprising different DNA fragments of interest are processed simultaneously.

The invention also provides a method for preparing a eukaryotic non-human organism, preferably a plant, wherein the expression of a target nucleic acid of interest is reduced or inhibited, the method comprising:

preparing a chimeric DNA construct capable of expressing a dsRNA in cells of the eukaryotic non-human organism according to methods of the invention;

introducing the chimeric DNA construct in cells of the eukaryotic non-human organism; and isolating the transgenic eukaryotic organism.

It is also an objective of the invention to provide a method for isolating a nucleic acid molecule involved in determining a particular trait, comprising the steps of:

preparing a library of chimeric DNA constructs capable of expressing a dsRNA in cells of the eukaryotic non-human organism according to any one of the methods of the invention;

introducing individual representatives of the library of chimeric DNA constructs in cells of the eukaryotic non-human organism;

isolating a eukaryotic organism exhibiting the particular trait; and isolating the nucleic acid molecule.

The invention also provides a eukaryotic non-human organism, preferably a plant comprising a chimeric DNA construct obtainable through the methods of the invention.

BRIEF DESCRIPTION OF THE FIGURES

FIG. 1. Schematic representation of vectors and method used in a preferred embodiment of the invention.

Figure 1A:
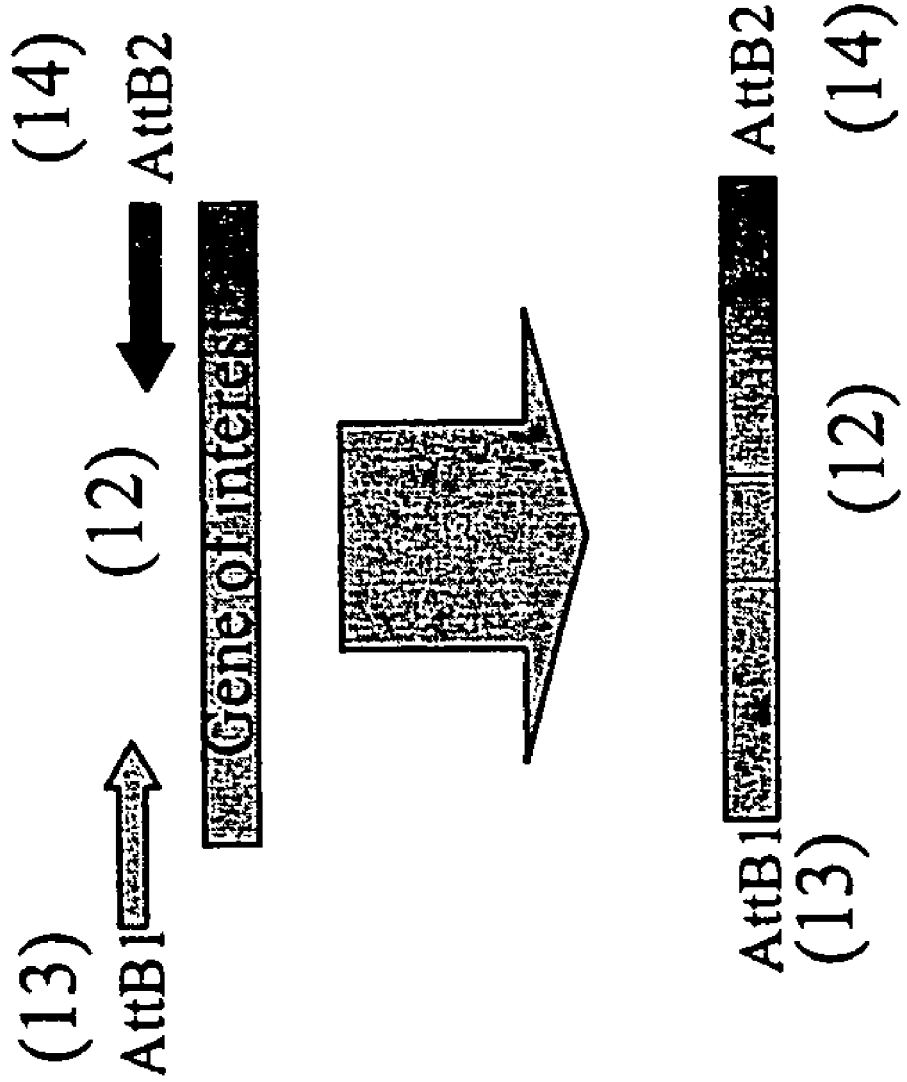
FIG. 1A: A nucleic acid of interest (12) is amplified by PCR using primers comprising two different recombination sites (13, 14) which cannot react with each other or with the same other recombination site. This results in "insert DNA" wherein the nucleic acid of interest (12) is flanked by two different recombination sites (13, 14).

This results in a chimeric DNA construct with the desired configuration comprising a eukaryotic promoter region (3); a recombination site (15) produced by the recombination between recombination sites (4) and (13); a first copy of the DNA of interest (12); a recombination site (16) produced by the recombination between recombination sites (5) and (14); optionally an intron sequence flanked by intron processing signals (11); a recombination site (17) produced by the recombination between recombination sites (6) and (14); a second copy of the DNA of interest (12) in opposite orientation to the first copy of the DNA of interest; a recombination site (18) produced by the recombination between recombination sites (7) and (13); a eukaryotic transcription terminator and polyadenylation signal (8).

Figure 2B:
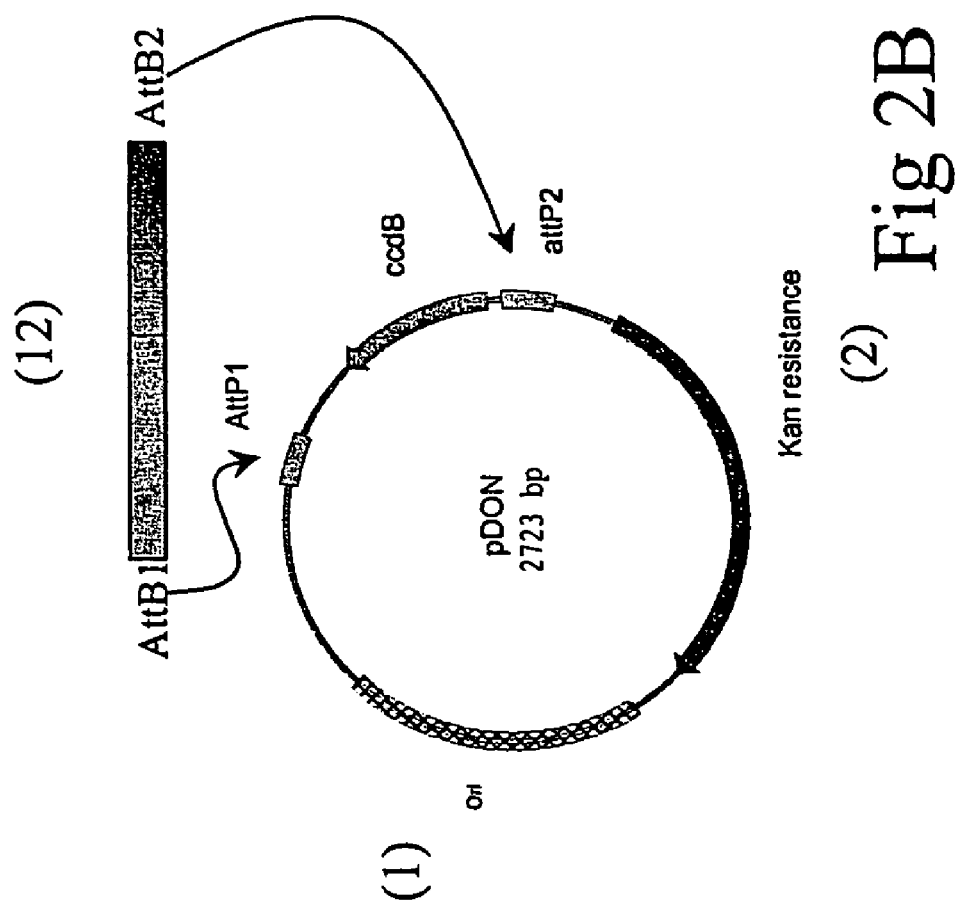
Figure 2A:
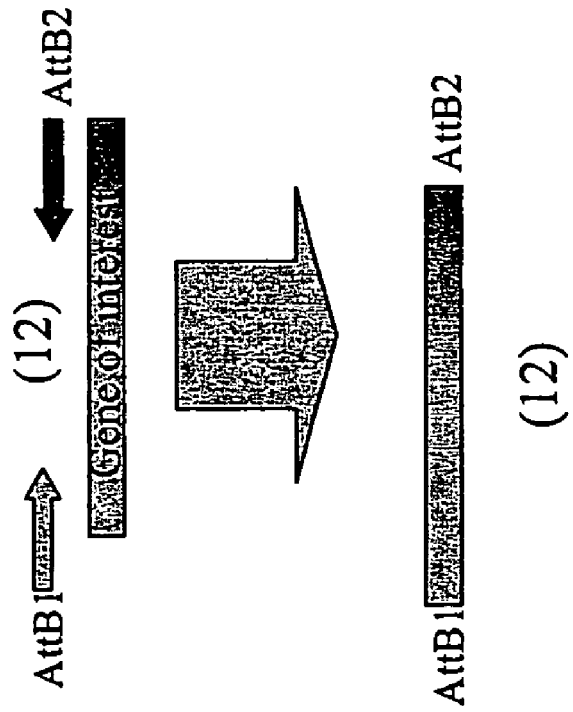

FIG. 2A: A nucleic acid of interest (12) is amplified by PCR using primers comprising two different recombination sites which upon recombination with the recombination sites on an intermediate vector (FIG. 2B) will yield recombination sites compatible with the first (4) and fourth (5) and with the second (6) and third (7) recombination site on the acceptor vector respectively.

FIG. 2B: The insert DNA obtained in FIG. 2A is allowed to recombine with the intermediate vector in the presence of at least one recombination protein to obtain an intermediate DNA wherein the DNA of interest (12) is flanked by two different recombination sites (13, 14) and which further comprises an origin of replication (1) and a selectable marker gene (2).

Figure 1B:
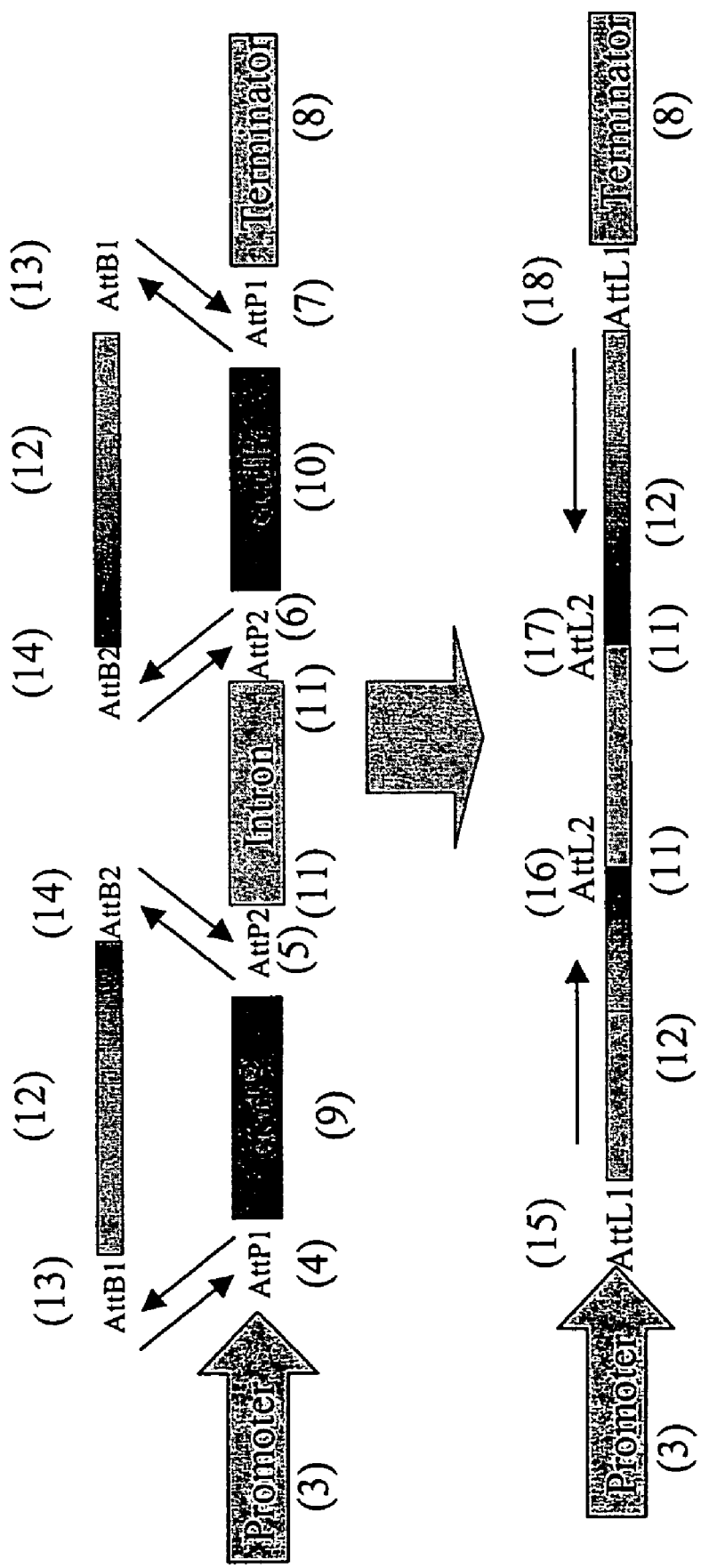
FIG. 1B. Using at least one recombination protein, the insert DNA is allowed to recombine with the acceptor vector between the recombination sites, whereby the first (4) and fourth recombination site (7) react with one of the recombination sites (13) flanking the PCR amplified DNA of interest (12) and the second (5) and third (6) recombination site on the acceptor vector recombine with the other recombination site (14) flanking the DNA of interest (12). The desired product DNA can be isolated by selecting for loss of the selectable marker genes (9) and (10) located between respectively the first (4) and second (5) recombination sites and the third (6) and fourth (7) recombination sites. Optionally, an additional selectable marker gene may be included between the second (5) and third (6) recombination site to allow selection for the presence of this selectable marker gene and consequently for the optional intron sequence, which is flanked by functional intron processing signal sequences (11). The acceptor vector, as well as the product vector further comprises an origin of replication (Ori; (1)) and a selectable marker gene (2) to allow selection for the presence of the plasmid.
Figure 2C:
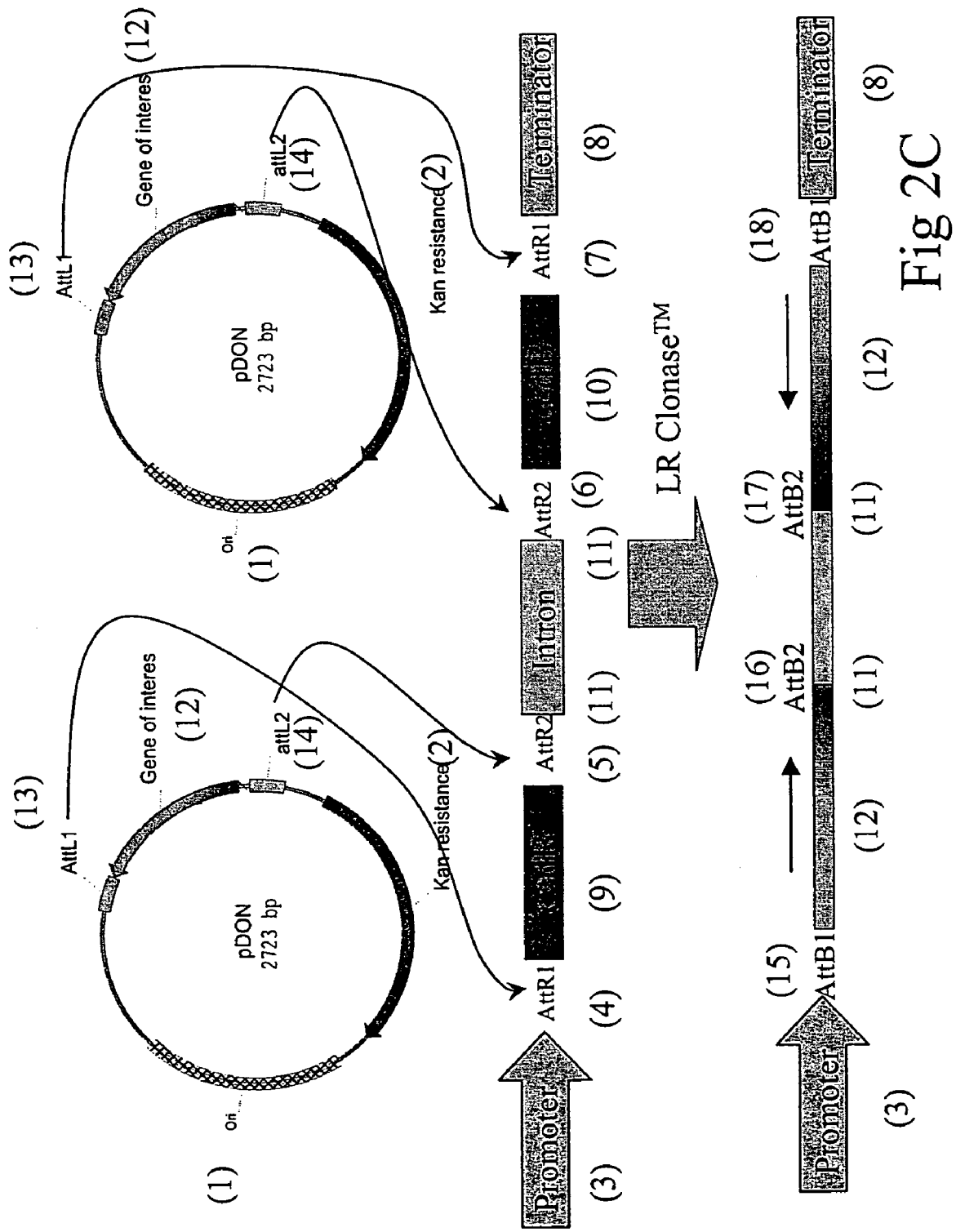

FIG. 2C: The intermediate DNA is then allowed to recombine with the acceptor vector using at least one second recombination protein (basically as described for FIG. 1B).

Figure 3:
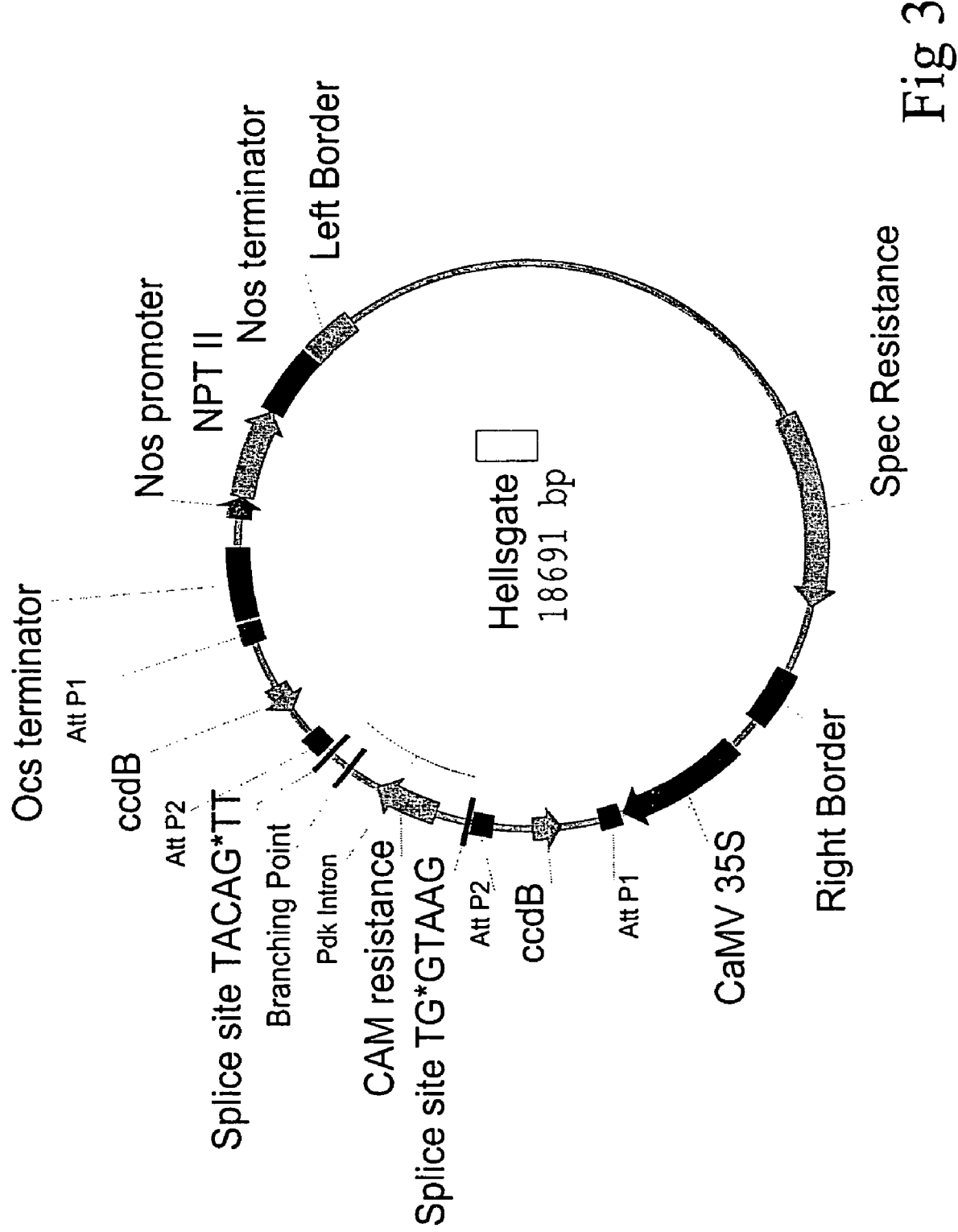

FIG. 3: Schematic representation of the acceptor vector "pHELLSGATE"

Figure 4:
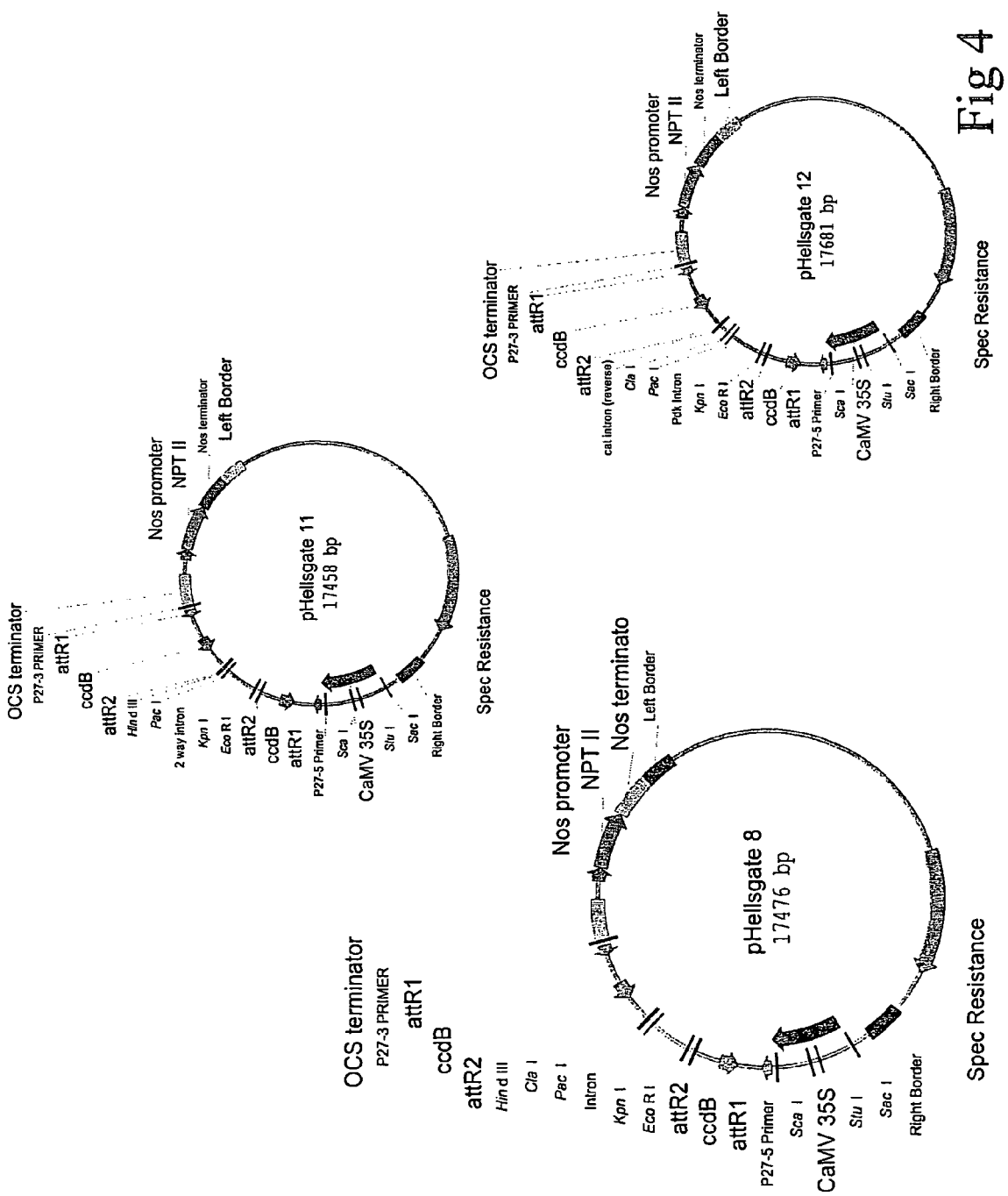

FIG. 4: Schematic representation of the acceptor vectors "pHELLSGATE 8" "pHELLSGATE 11" and "pHELLSGATE 12".

DETAILED DESCRIPTION OF PREFERRED EMBODIMENTS

The current invention is based on the unexpected finding by the inventors that recombinational cloning was an efficient one-step method to convert a nucleic acid fragment of interest into a chimeric DNA construct capable of producing a dsRNA transcript comprising a sense and antisense nucleotide sequence capable of being expressed in eukaryotic cells. The dsRNA molecules are efficient effectors of gene silencing. These methods improve the efficiency problems previously encountered to produce chimeric DNAs with long inverted repeats.

Thus, in a first embodiment, the invention provides a method for making a chimeric DNA construct or chimeric gene capable of expressing an RNA transcript in a eukaryotic cell, the RNA being capable of internal basepairing between a stretch of nucleotides corresponding to a nucleic acid of interest and its complement (i.e. the stretch of nucleotides in inverted orientation) located elsewhere in the transcript (and thus forming a hairpin RNA) comprising the following steps:

providing an "acceptor vector" comprising the following operably linked DNA fragments:

an origin of replication allowing replication in a host cell (1), a selectable marker region (2) capable of being expressed in the host cell; and a chimeric DNA construct comprising in sequence:

a promoter or promoter region (3) capable of being recognized by RNA polymerases of a eukaryotic cell;

a first recombination site (4), a second recombination site (5), a third recombination site (6) and a fourth recombination site (7), whereby the first (4) and fourth recombination site (7) are capable of reacting with the same other recombination site and preferably are identical to each other;

the second (5) and third (6) recombination site are also capable of reacting with the same other recombination site and preferably are identical to each other;

the first (4) and second (5) recombination site do not recombine with each other or with the same other recombination site; and
the third (6) and fourth (7) recombination site do not recombine with each other or with the same other recombination site; and
a 3' transcription terminating and polyadenylation region (8) functional in a eukaryotic cell;
providing an "insert DNA" comprising
the DNA segment of interest (12) flanked by
a fifth recombination site (13) which is capable of recombining with the first(4) or fourth (7) recombination site but preferably not with the second (5) or third (6) recombination site;
a sixth recombination site (14), which is capable of recombining with the second (5) or third (6) recombination site but preferably not with the first (4) or fourth (7) recombination site.
combining in vitro the insert DNA and the acceptor vector in the presence of at least one specific recombination protein; and
allowing the recombination to occur to produce a reaction mixture comprising inter alia "product DNA" molecules which comprise in sequence
the promoter or promoter region (3) capable of being recognized by RNA polymerases of a eukaryotic cell;
a recombination site (15) which is the recombination product of the first (4) and fifth recombination site (13);
a first copy of the DNA fragment of interest (12);
a recombination site (16) which is the recombination product of the second (4) and the sixth recombination site (14);
a recombination site (17) which is the recombination product of the third (5) and the sixth recombination site (14);
a second copy of the DNA fragment of interest in opposite orientation (12) with regard to the first copy;
a recombination site (18) which is the recombination product of the fourth (7) and the fifth recombination site (13); and
a 3' transcription terminating and polyadenylation region (8) functional in a eukaryotic cell; and
selecting the product DNA molecules.

This method is schematically outlined in FIG. 1, with non-limiting examples of recombination sites and selectable markers.

As used herein, a "host cell" is any prokaryotic or eukaryotic organism that can be a recipient for the acceptor vector or the product DNA. Conveniently, the host cell will be an *Escherichia coli* strain commonly used in recombinant DNA methods.

A "recombination protein" is used herein to collectively refer to site-specific recombinases and associated proteins and/or co-factors. Site-specific recombinases are enzymes that are present in some viruses and bacteria and have been characterized to have both endonuclease and ligase properties. These recombinases (along with associated proteins in some cases) recognize specific sequences of bases in DNA and exchange the DNA segments flanking those segments. Various recombination proteins are described in the art(see WO 96/40724 herein incorporated by reference in its entirety, at least on page 22 to 26). Examples of such recombinases include Cre from bacteriophage P1 and Integrase from bacteriophage lambda.

Cre is a protein from bacteriophage P1 (Abremski and Hoess, 1984) which catalyzes the exchange between 34 bp DNA sequences called loxP sites (see Hoess et al., 1986. Cre is available commercially (Novagen, Catalog 69247-1).

Integrase (Int) is a protein from bacteriophage lambda that mediates the integration of the lambda genome into the *E. coli* chromosome. The bacteriophage lambda Int recombinational proteins promote irreversible recombination between its substrate att sites as part of the formation or induction of a lysogenic state. Reversibility of the recombination reactions results from two independent pathways for integrative or excisive recombination. Cooperative and competitive interactions involving four proteins (Int, Xis, IHF and FIS) determine the direction of recombination. Integrative recombination involves the Int and IHF proteins and attP (240 bp) and attB (25b) recombination sites. Recombination results in the formation of two new sites: attL and affR. A commercial preparation comprising Int and IHF proteins is commercially available (BP clonase™; Life Technologies). Excisive recombination requires Int, IHF, and Xis and sites attL and attR to generate attP and attB. A commercial preparation comprising Int, IHF and Xis proteins is commercially available (LR clonase™; Life Technologies).

A "recombination site" as used herein refers to particular DNA sequences, which a recombinase and possibly associated proteins recognizes and binds. The recombination site recognized by Cre recombinase is loxP which is a 34 base pair sequence comprised of two 13 base pair inverted repeats (serving as recombinase binding sites) flanking an 8 base pair core sequence. The recombination sites attB, attP, attL and attR are recognized by lambda integrase. AttB is an approximately 25 base pair sequence containing two 9 base pair core-type Int binding sites and a 7 base pair overlap region. AttP is an approximately 240 base pair sequence containing core-type Int binding sites and arm-type Int binding sites as well as sites for auxiliary proteins IHF, FIS and Xis (Landy 1993). Each of the att sites contains a 15 bp core sequence with individual sequence elements of functional significance lying within, outside and across the boundaries of this common core (Landy, 1989) Efficient recombination between the various att sites requires that the sequence of the central common region is substantially identical between the recombining partners. The exact sequence however is modifiable as disclosed in WO 96/40724 and the variant recombination sites selected from

```
attB1:    AGCCTGCTTTTTTGTACAAACTTGT;  (SEQ ID No 1)

attB2:    AGCCTGCTTTCTTGTACAAACTTGT;  (SEQ ID No 2)

attB3:    ACCCAGCTTTCTTGTACAAACTTGT;  (SEQ ID No 3)

attR1:    GTTCAGCTTTTTTGTACAAACTTGT;  (SEQ ID No 4)

attR2:    GTTCAGCTTTCTTGTACAAACTTGT;  (SEQ ID No 5)

attR3:    GTTCAGCTTTCTTGTACAAAGTTGG;  (SEQ ID No 6)

attL1:    AGCCTGCTTTTTTGTACAAAGTTGG;  (SEQ ID No 7)

attL2:    AGCCTGCTTTCTTGTACAAAGTTGG;  (SEQ ID No 8)

attL3:    ACCCAGCTTTCTTGTACAAAGTTGG;  (SEQ ID No 9)

attP1:    GTTCAGCTTTTTTGTACAAAGTTGG;  (SEQ ID No 10)
or attP2,P3: GTTCAGCTTTCTTGTACAAAGTTGG   (SEQ ID No 11)
``` allow more flexibility in the choice of suitable pairs or recombination sites that have the capability to recombine (as indicated by their index number).

It will be clear to the skilled artisan that a correspondence is required between the recombination site(s) used and the recombination proteins used.

In one embodiment, the following combinations of recombination sites for the acceptor vector are present in the acceptor vector:
  the first (4) and fourth (7) recombination sites are identical and comprise
    attP1 comprising
      the nucleotide sequence of SEQ ID No 10 and
  the second (5) and third (6) recombination site are also identical and comprise
    attP2 comprising
      the nucleotide sequence of SEQ ID No 11; or
  the first (4) and fourth (7) recombination sites are identical and comprise
    attR1 comprising
      the nucleotide sequence of SEQ ID No 4 and
  the second (5) and third (6) recombination site are also identical and comprise
    attR2 comprising
      the nucleotide sequence of SEQ ID No 5; and the following combinations of recombination sites for the insert DNA are used:
  the fifth (13) recombination site comprises
    attB1 comprising
      the nucleotide sequence of SEQ ID No 1 and
  the sixth (14) recombination site comprises
    attB2 comprising
      the nucleotide sequence of SEQ ID No 2, the combination being suitable for recombination with the first acceptor vector mentioned above; or
  the fifth (13) recombination site comprises
    attL1 comprising
      the nucleotide sequence of SEQ ID No 7 and
  the sixth (14) recombination site comprises
    attL2 comprising
      the nucleotide sequence of SEQ ID No 8, the combination being suitable for recombination with the second acceptor vector mentioned above.

It has been unexpectedly found that product DNA molecules (resulting from recombination between the above mentioned second acceptor vector with attR recombination sites (such as pHELLSGATE 8) and insert DNA flanked by attL recombination sites) wherein the gene inserts in both orientations are flanked by attB recombination sites are more effective in silencing of the target gene(both quantitatively and qualitatively) than product DNA molecules (resulting from recombination between the above mentioned first acceptor vector with attP recombination sites (such as pHELLSGATE or pHELLSGATE 4) and insert DNA flanked by attB recombination sites) wherein the gene inserts in both orientations are flanked by attL recombination sites. Although not intending to limit the invention to a particular mode of action it is thought that the greater length of the attL sites and potential secondary structures therein may act to inhibit transcription yielding the required dsRNA to a certain extent. However, acceptor vectors such as the above mentioned first acceptor vectors with attP sites may be used when target gene silencing to a lesser extent would be useful or required.

The dsRNA obtained by the chimeric DNA construct made according to the invention may be used to silence a nucleic acid of interest, i.e., to reduce its phenotypic expression, in a eukaryotic organism, particularly a plant, either directly or by transcription of the chimeric DNA construct in the cells of the eukaryotic organism. When this is the case, the following considerations may apply.

The length of the nucleic acid of interest (12) may vary from about 10 nucleotides (nt) up to a length equaling the length (in nucleotides) of the target nucleic acid whose phenotypic expression is to be reduced. Preferably the total length of the sense nucleotide sequence is at least 10 nt, or at least 19 nt, or at least 21 nt, or at least 25 nt, or at least about 50 nt, or at least about 100 nt, or at least about 150 nt, or at least about 200 nt, or at least about 500 nt. It is expected that there is no upper limit to the total length of the sense nucleotide sequence, other than the total length of the target nucleic acid. However for practical reasons (such as, e.g., stability of the chimeric genes) it is expected that the length of the sense nucleotide sequence should not exceed 5000 nt, particularly should not exceed 2500 nt and could be limited to about 1000 nt.

It will be appreciated that the longer the total length of the nucleic acid of interest (12), the less stringent the requirements for sequence identity between the nucleic acid of interest and the corresponding sequence in the target gene. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target nucleic acid. However, it is preferred that the nucleic acid of interest always includes a sequence of about 10 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense sequence, the number of gaps should be minimized, particularly for the shorter sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP, which is part of the Wisconsin Package Version 10.1 (Genetics Computer Group, Madison, Wis., USA) using the default scoring matrix with a gap creation penalty of 50 and a gap extension penalty of 3. Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are the to be essentially similar or have a certain degree of sequence identity with DNA sequences, thymine (T) in the DNA sequence is considered equal to uracil (U) in the RNA sequence.

The "insert DNA" may conveniently be provided using DNA amplification procedures, such as PCR, of the nucleic acid of interest, using as primers oligonucleotide sequences incorporating appropriate recombination sites as well as oligonucleotide sequences appropriate for the amplification of the nucleic acid of interest. However, alternative methods are available in the art to provide the nucleic acid of interest with the flanking recombination sites, including but not limited to covalently linking oligonucleotides or nucleic acid fragments comprising such recombination sites to the nucleic acid(s) of interest using ligase(s).

The providing of the appropriate flanking recombination sites to the nucleic acid may also proceed in several steps. For example, in a first step the flanking sites provided to the nucleic acid of interest may be such that upon recombination with the recombination sites in an intermediate vector new recombination sites are created flanking the nucleic acid of interest, now compatible for recombination with the acceptor vector. This scheme is outlined in FIG. 2, with non-limiting examples of recombination sites and selectable markers. It is understood that the insert DNA may be in a circular form or in a linear form.

As used herein, an "origin of replication" is a DNA fragment which allows replication of the acceptor vector in microorganisms, preferably bacteria, particularly *E. coli* strains, and ensures that upon multiplication of the microorganism, the daughter cells receive copies of the acceptor vector.

"Selectable marker (gene)" is used herein to indicate a DNA segment that allows selection or screening for the presence or absence of that DNA segment under suitable conditions. Selectable markers include but are not limited to:

DNA segments that encode products which provide resistance against otherwise toxic compounds (e.g. antibiotic resistance genes, herbicide resistance genes);

DNA segments encoding products which are otherwise lacking in the recipient cell (e.g. tRNA genes, auxotrophic markers);

DNA segments encoding products which suppress the activity of a gene product;

DNA segments encoding products which can readily be identified (e.g. β-galactosidase, green fluorescent protein (GFP), β-glucuronidase (GUS));

DNA segments that bind products which are otherwise detrimental to cell survival and/or function;

DNA segments that are capable of inhibiting the activity of any of the DNA segments Nos (1) to (5) (e.g. antisense oligonucleotides);

DNA segments that bind products that modify a substrate (e.g. restriction endonuclease);

DNA segments that can be used to isolate a desired molecule (e.g. specific protein binding sites);

DNA segments that encode a specific nucleotide sequence which can be otherwise non-functional (e.g. for PCR amplification of subpopulations of molecules);

DNA segments, which when absent, directly or indirectly confer sensitivity to particular compound(s); and/or DNA segments, which when absent, directly or indirectly confer resistance to particular compound(s).

Preferred first selectable markers (2) are antibiotic resistance genes. A large number of antibiotic resistance genes, particularly which can be used in bacteria, are available in the art and include but are not limited to aminoglycoside phosphotransferase I and II, chloramphenicol acetyltransferase, beta-lactamase, and/or aminoglycoside adenosyltransferase.

Preferred second selectable markers (9) and third selectable markers (10) are selectable markers allowing a positive selection when absent or deleted after recombination (i.e. in the product DNA) such as but not limited to ccdB gene the product of which interferes with *E coli* DNA gyrase and thereby inhibits growth of most *E. coli* strains. Preferably, the second and third markers are identical.

In one embodiment of the invention, the acceptor comprises a fourth selectable marker (19) between the second (5) and third (6) recombination site, preferably a marker allowing positive selection for the presence thereof, such as a antibiotic resistance gene, e.g. chloramphenicol resistance gene. Preferably, the fourth selectable marker should be different from first selectable marker and different from the second and third selectable marker. The presence of a fourth selectable marker allows to select or screen for the retention of the DNA region between the second (5) and third (6) recombination site in the product DNA. This increases the efficiency with which the desired product DNAs having the nucleic acid of interest cloned in inverted repeat and operably linked to eukaryotic expression signals may be obtained. However, it has been found that with most of the acceptor vectors tested, the presence of a selectable marker is not required and has little influence on the ratio of expected and desired product DNA molecules (which usually exceeds about 90% of obtained product DNA molecules) to undesired product DNA molecules.

It will be understood that a person skilled in the art has a number of techniques available for recognizing the expected and desired product DNA molecules, such as but not limited to restriction enzyme digests or even determining the nucleotide sequence of the recombination product.

In another embodiment of the invention, the acceptor vector further comprises a pair of intron processing signals (11) or an intron sequence functional in the eukaryotic cell, preferably located between the second (5) and third (6) recombination site. However, the pair of intron processing signals or the intron may also be located elsewhere in the chimeric construct between the promoter or promoter region (3) and the terminator region (8). As indicated in the background art, this will improve the efficiency with which the chimeric DNA construct encoding the dsRNA will be capable of reducing the phenotypic expression of the target gene in the eukaryotic cell. A particularly preferred intron functional in cells of plants is the pdk intron (*Flaveria trinervia* pyruvate orthophosphate dikinase intron 2; see WO99/53050 incorporated by reference). The fourth selectable marker (19) may be located between the intron processing signals or within the intron (if these are located between the second and third recombination site), but may also be located adjacent to the intron processing signals or the intron.

A person skilled in the art will recognize that the product DNA molecules, resulting from a recombination with an acceptor vector as herein described, which comprise a region between the second (5) and third (6) recombination will fall into two classes which can be recognized by virtue of the orientation of that intervening region. In the embodiments wherein the acceptor vector also comprises an intron, the different orientation may necessitate an additional step of identifying the correct orientation. To avoid this additional step, the acceptor vector may comprise an intron that can be spliced out independent of its orientation (such as present in pHELLSGATE 11) or the acceptor vector may comprise a spliceable intron in both orientations (such as present in pHELLSGATE 12).

As used herein, the term "promoter" denotes any DNA that is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters. Other suitable promoters include tissue-specific or organ-specific promoters including but not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865) and the like.

The acceptor vector may further comprise a selectable marker for expression in a eukaryotic cell. Selectable marker genes for expression in eukaryotic cells are well known in the art, including but not limited to chimeric marker genes. The chimeric marker gene can comprise a marker DNA that is operably linked at its 5' end to a promoter, functioning in the host cell of interest, particularly a plant-expressible promoter, preferably a constitutive promoter, such as the CaMV $^{35}$S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable color to the transformed plant cell, such as the A1 gene (Meyer et al., 1987), can provide herbicide resistance to the transformed plant cell, such as the bar gene, encoding resistance to phosphinothricin (EP 0,242,246), or can provide antibiotic resistance to the transformed cells, such as the aac(6') gene, encoding resistance to gentamycin (WO94/01560).

The acceptor vector may also further comprise left and right T-DNA border sequences flanking the chimeric DNA construct, and may comprise an origin of replication functional in *Agrobacterium* spp. and/or a DNA region of homology with a helper Ti-plasmid as described in EP0 116718.

The efficiency and ease by which any nucleic acid of interest may be converted into a chimeric DNA construct comprising two copies of the nucleic acid of interest in inverted repeat and operably linked to eukaryotic 5' and 3' regulatory regions using the means and methods according to the invention, makes these particularly apt for automation and high throughput analysis.

It will be clear to the person skilled in the art that the acceptor vectors as hereinbefore described can be readily adapted to provide a vector which can be used to produce in vitro large amounts of double stranded RNA or RNAi comprising a complementary sense and antisense portion essentially similar to a target gene of choice as described elsewhere in this application, by exchanging the promoter capable of being expressed in a eukaryotic cell for a promoter recognized by any RNA polymerase. Very suitable promoters to this end are the promoters recognized by bacteriophage single subunit RNA polymerases such as the promoters recognized by bacteriophage single subunit RNA polymerase such as the RNA polymerases derived from the *E. coli* phages T7, T3, φI, φII, W31, H, Y, A1, 122, cro, C21, C22, and C2; *Pseudomonas putida* phage gh-1; *Salmonella typhimurium* phage SP6; *Serratia marcescens* phage IV; *Citrobacter* phage ViIII; and *Klebsiella* phage No.11 (Hausmann, Current Topics in Microbiology and Immunology, 75: 77-109 (1976); Korsten et al., J. Gen Virol. 43: 57-73 (1975); Dunn et al., *Nature New Biology*, 230: 94-96 (1971); Towle et al., *J. Biol. Chem.* 250: 1723-1733 (1975); Butler and Chamberlin, *J. Biol. Chem.*, 257: 5772-5778 (1982)). Examples of such promoters are a T3 RNA polymerase specific promoter and a T7 RNA polymerase specific promoter, respectively. A T3 promoter to be used as a first promoter in the CIG can be any promoter of the T3 genes as described by McGraw et al, *Nucl. Acid Res.* 13: 6753-6766 (1985). Alternatively, a T3 promoter may be a T7 promoter that is modified at nucleotide positions-10, -11 and -12 in order to be recognized by T3 RNA polymerase (Klement et al., *J. Mol. Biol.* 215, 21-29 (1990)). A preferred T3 promoter is the promoter having the "consensus" sequence for a T3 promoter, as described in U.S. Pat. No. 5,037,745. A T7 promoter which may be used according to the invention, in combination with T7 RNA polymerase, comprises a promoter of one of the T7 genes as described by Dunn and Studier, *J. Mol. Biol.* 166: 477-535 (1983). A preferred T7 promoter is the promoter having the "consensus" sequence for a T7 promoter, as described by Dunn and Studier (supra).

Thus, the invention also provides an acceptor vector comprising:

origin of replication allowing replication in a host cell (1);

a selectable marker region (2) capable of being expressed in the host cell; and a chimeric DNA construct comprising in sequence:

a promoter or promoter region (3) capable of being recognized by a bacteriophage single subunit RNA polymerase;

a first recombination site (4), a second recombination site (5), a third recombination site (6) and a fourth recombination site (7) whereby the first (4) and fourth recombination site (7) are capable of reacting with the same other recombination site and preferably are identical to each other;

the second (5) and third (6) recombination site are also capable of reacting with the same other recombination site and preferably are identical to each other;

the first (4) and second (5) recombination site do not recombine with each other or with the same other recombination site; and the third (6) and fourth (7) recombination site do not recombine with each other or with the same other recombination site; and a 3' transcription terminating and polyadenylation region (8) functional in a eukaryotic cell.

The acceptor vector may be used to convert a DNA fragment of interest into an inverted repeat structure as described elsewhere in the application and dsRNA can be produced in large amounts by contacting the acceptor vector DNA with the appropriate bacteriophage single subunit RNA polymerase under conditions well known to the skilled artisan.

The so-produced dsRNA can then be used for delivery into cells prone to gene silencing, such as plant cells, fungal cells or animal cells. dsRNA may be introduced in animal cells via liposomes or other transfection agents (e.g. Clonfection transfection reagent or the CalPhos Mammalian transfection kit from ClonTech) and could be used for methods of treatment of animals, including humans, by silencing the appropriate target genes.

The acceptor vectors may also be equipped with any prokaryotic promoter suitable for expression of dsRNA in a particular prokaryotic host. The prokaryotic host can be used as a source of dsRNA, e.g. by feeding it to an animal, such as a nematode, in which the silencing of the target gene is envisioned.

The promoter capable of expression in eukaryotic cell may also be a promoter capable of expression in a mammalian cell and vectors according to the invention may transiently be delivered using a retroviral delivery system or other animal transfection system.

In another embodiment of the invention, a method is provided for making a eukaryotic organism, particularly a plant, wherein the phenotypic expression of a target nucleic acid of interest is reduced or inhibited, comprising the steps of preparing a chimeric DNA construct comprising a nucleic acid of interest (12) comprising a nucleotide sequence of at least 19 bp or 25 bp having at least 70% sequence identity to the target nucleic acid of interest and capable of expressing a dsRNA in cells of the eukaryotic organism, particularly a plant according to the methods of the current invention and introducing the chimeric DNA construct in cells of the eukaryotic organism, and isolating eukaryotic organism transgenic for the chimeric DNA construct.

As used herein, "phenotypic expression of a target nucleic acid of interest" refers to any quantitative trait associated with the molecular expression of a nucleic acid in a host cell and may thus include the quantity of RNA molecules transcribed or replicated, the quantity of post-transcriptionally modified RNA molecules, the quantity of translated peptides or proteins, the activity of such peptides or proteins.

A "phenotypic trait" associated with the phenotypic expression of a nucleic acid of interest refers to any quantitative or qualitative trait, including the trait mentioned, as well as the direct or indirect effect mediated upon the cell, or the organism containing that cell, by the presence of the RNA molecules, peptide or protein, or posttranslationally modified peptide or protein. The mere presence of a nucleic acid in a host cell, is not considered a phenotypic expression or a phenotypic trait of that nucleic acid, even though it can be quantitatively or qualitatively traced. Examples of direct or indirect effects mediated on cells or organisms are, e.g., agronomically or industrial useful traits, such as resistance to a pest or disease; higher or modified oil content etc.

As used herein, "reduction of phenotypic expression" refers to the comparison of the phenotypic expression of the target nucleic acid of interest to the eukaryotic cell in the presence of the RNA or chimeric genes of the invention, to the phenotypic expression of the target nucleic acid of interest in the absence of the RNA or chimeric genes of the invention. The phenotypic expression in the presence of the chimeric RNA of the invention should thus be lower than the phenotypic expression in absence thereof, preferably be only about 25%, particularly only about 10%, more particularly only about 5% of the phenotypic expression in absence of the chimeric RNA, especially the phenotypic expression should be completely inhibited for all practical purposes by the presence of the chimeric RNA or the chimeric gene encoding such an RNA.

A reduction of phenotypic expression of a nucleic acid where the phenotype is a qualitative trait means that in the presence of the chimeric RNA or gene of the invention, the phenotypic trait switches to a different discrete state when compared to a situation in which such RNA or gene is absent. A reduction of phenotypic expression of a nucleic acid may thus, i.a. be measured as a reduction in transcription of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a target nucleic acid of interest, may be accompanied by or correlated to an increase in a phenotypic trait.

As used herein a "target nucleic acid of interest" refers to any particular RNA molecule or DNA sequence which may be present in a eukaryotic cell, particularly a plant cell whether it is an endogenous nucleic acid, a transgenic nucleic acid, a viral nucleic acid, or the like.

Methods for making transgenic eukaryotic organisms, particularly plants are well known in the art. Gene transfer can be carried out with a vector that is a disarmed Ti-plasmid, comprising a chimeric gene of the invention, and carried by *Agrobacterium*. This transformation can be carried out using the procedures described, for example, in EP 0 116 718. Particular kinds of *Agrobacterium* mediated transformation methods are the so-called in planta methods, which are particularly suited for *Arabidopsis* spp. transformation (e.g., Clough and Bent, *Plant J.* 16: 735-534, 1998). Alternatively, any type of vector can be used to transform the plant cell, applying methods such as direct gene transfer (as described, for example, in EP 0 233 247), pollen-mediated transformation (as described, for example, in EP 0 270 356, WO85/01856 and U.S. Pat. No. 4,684,611), plant RNA virus-mediated transformation (as described, for example, in EP 0 067 553 and U.S. Pat. No. 4,407,956), liposome-mediated transformation (as described, for example, in U.S. Pat. No. 4,536,475), and the like. Other methods, such as microprojectile bombardment, as described for corn by Fromm et al. (1990) and Gordon-Kamm et at (1990), are suitable as well. Cells of monocotyledonous plants, such as the major cereals, can also be transformed using wounded and/or enzyme-degraded compact embryogenic tissue capable of forming compact embryogenic callus, or wounded and/or degraded immature embryos as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the chimeric gene for reduction of the phenotypic expression of a nucleic acid of interest of the invention in other varieties of the same or related plant species, or in hybrid plants. Seeds obtained from the transformed plants contain the chimeric genes of the invention as a stable genomic insert.

In another embodiment, the invention provides a method for isolating a nucleic acid molecule involved in determining a particular phenotypic trait of interest. The method involves the following steps:

preparing a library of chimeric DNA constructs capable of expressing a dsRNA in cells of the eukaryotic non-human organism using the methods and means described in the current invention;

introducing individual representatives of this library of chimeric DNA constructs in cells of the eukaryotic non-human organism, preferably by stable integration in their genome, particularly their nuclear genome;

isolating a eukaryotic organism exhibiting the particular trait; and isolating the corresponding nucleic acid molecule present in the eukaryotic organism with the trait of interest, preferably from the aforementioned library.

It will be understood that the methods and means of the invention may be used to determine the function of an isolated nucleic acid fragment or sequence with unknown function, by converting a part or the whole of that nucleic acid fragment or sequence according to the methods of the invention into a chimeric construct capable of making a dsRNA transcript when introduced in a eukaryotic cell, introducing that chimeric DNA construct into a eukaryotic organism to isolate preferably a number of transgenic organisms and observing changes in phenotypic traits.

The invention also provides acceptor vectors, as described in this specification as well as kits comprising such vectors.

It will be understood that the vectors, methods and kits according to the invention may be used in all eukaryotic organisms which are prone to gene silencing including yeast, fungi, plants, animals such as nematodes, insects and arthropods, vertebrates including mammals and humans.

Also provided by the invention are non-human organisms comprising chimeric DNA constructs comprising in sequence the following operably linked DNA fragments a promoter or promoter region (3) capable of being recognized by RNA polymerases of the eukaryotic cell; a recombination site (15) which is the recombination product of the first (4) recombination site on the acceptor vector and the fifth recombination site (13) flanking the DNA of interest; a first DNA copy of the nucleic acid fragment of interest (12);

a recombination site (16) which is the recombination product of the second (4) recombination site on the acceptor vector and the sixth recombination site (14) flanking the DNA of interest;

a recombination site (17) which is the recombination product of the third (5) recombination site on the acceptor vector and the sixth recombination site (14) flanking the DNA of interest;

a second DNA copy of the nucleic acid fragment of interest in opposite orientation (12) compared to the first copy;

a recombination site (18) which is the recombination product of the fourth (7) recombination site on the acceptor vector and the fifth recombination site (13) flanking the DNA of interest; and a 3' transcription terminating and polyadenylation region (8) functional in a eukaryotic cell.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region that is functionally or structurally defined, may comprise additional DNA regions etc.

The term "gene" means any DNA fragment comprising a DNA region (the "transcribed DNA region") that is transcribed into a RNA molecule (e.g., a mRNA) in a cell operably linked to suitable regulatory regions, e.g., a plant-expressible promoter. A gene may thus comprise several operably linked DNA fragments such as a promoter, a 5' leader sequence, a coding region, and a 3' region comprising a polyadenylation site. A plant gene endogenous to a particular plant species (endogenous plant gene) is a gene which is naturally found in that plant species or which can be introduced in that plant species by conventional breeding. A chimeric gene is any gene that is not normally found in a plant species or, alternatively, any gene in which the promoter is not associated in nature with part or all of the transcribed DNA region or with at least one other regulatory region of the gene.

The term "expression of a gene" refers to the process wherein a DNA region which is operably linked to appropriate regulatory regions, particularly to a promoter, is transcribed into an RNA which is biologically active i.e., which is either capable of interaction with another nucleic acid or which is capable of being translated into a polypeptide or protein. A gene is the to encode an RNA when the end product of the expression of the gene is biologically active RNA, such as e.g. an antisense RNA, a ribozyme or a replicative intermediate. A gene is the to encode a protein when the product of the expression of the gene is a protein or polypeptide.

A nucleic acid is "capable of being expressed", when the nucleic acid, when introduced in a suitable host cell, particularly in a plant cell, can be transcribed (or replicated) to yield an RNA, and/or translated to yield a polypeptide or protein in that host cell.

The following non-limiting Examples describe the construction of acceptor vectors and the application thereof for the conversion of nucleic acid fragments of interest into chimeric DNA constructs capable of expressing a dsRNA transcript in eukaryotic cells. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology*, Current Protocols, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Other references for standard molecular biology techniques include Sambrook and Russell (2001) *Molecular Cloning: A Laboratory Manual*, Third Edition, Cold Spring Harbor Laboratory Press, NY, Volumes I and II of Brown (1998) *Molecular Biology LabFax*, Second Edition, Academic Press (UK). Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR-Basics: From Background to Bench*, First Edition, Springer Verlag, Germany.

Throughout the description and Examples, reference is made to the following sequences:

SEQ ID No 1: core sequence of recombination site attB1
SEQ ID No 2: core sequence of recombination site attB2
SEQ ID No 3: core sequence of recombination site attB3
SEQ ID No 4: core sequence of recombination site attR1
SEQ ID No 5: core sequence of recombination site attR2
SEQ ID No 6: core sequence of recombination site attR3
SEQ ID No 7: core sequence of recombination site attL1
SEQ ID No 8: core sequence of recombination site attL2
SEQ ID No 9: core sequence of recombination site attL3
SEQ ID No 10: core sequence of recombination site attP1
SEQ ID No 11: core sequence of recombination sites attP2,P3
SEQ ID No 12: nucleotide sequence of chalcone synthase gene of *Arabidopsis*
SEQ ID No 13: nucleotide sequence of the acceptor vector "pHELLSGATE"
SEQ ID No 14: oligonucleotide attB1 "forward" primer used for amplification of 400 bp and 200 bp CHS fragments.

SEQ ID No 15: oligonucleotide attB2 "reverse" primer for amplification of the 400 bp CHS fragment.
SEQ ID No 16: oligonucleotide attB2 "reverse" primer for amplification of the 200 bp CHS fragment.
SEQ ID No 17: oligonucleotide attB1 "forward" primer used for amplification of 100 bp CHS fragment.
SEQ ID No 18: oligonucleotide attB2 "reverse" primer for amplification of the 100 bp CHS fragment.
SEQ ID No 19: oligonucleotide attB1 "forward" primer used for amplification of 50 bp CHS fragment.
SEQ ID No 20: oligonucleotide attB2 "reverse" primer for amplification of the 50 bp CHS fragment.
SEQ ID No 21: oligonucleotide attB1 "forward" primer for amplification of the 25 bp CHS fragment.
SEQ ID No 22: oligonucleotide attB2 "reverse" primer for the 25 bp fragment.
SEQ ID No 23: nucleotide sequence of the acceptor vector "pHELLSGATE 4"
SEQ ID No 24: nucleotide sequence of the acceptor vector "pHELLSGATE 8"
SEQ ID No 25: nucleotide sequence of the acceptor vector "pHELLSGATE 11"
SEQ ID No 26: nucleotide sequence of the acceptor vector "pHELLSGATE 12"

EXAMPLES

Example 1

Construction of the Acceptor Vector pHELLSGATE

With the completion of the *Arabidopsis* genome project, the advent of micro-array technology and the ever-increasing investigation into plant metabolic, perception, and response pathways, a rapid targeted way of silencing genes would be of major assistance. The high incidence and degree of silencing in plants transformed with chimeric genes containing simultaneously a sense and antisense nucleotide sequence, as well as a functional intron sequence suggested that such vectors could form the basis of a high-throughput silencing vector. However, one of the major obstacles in using such conventional cloning vectors for a large number of defined genes or a library of undefined genes would be cloning the hairpin arm sequences for each gene in the correct orientations.

Attempts to clone PCR products of sense and antisense arms together with the appropriately cut vector as a single step four-fragment ligation failed to give efficient or reproducible results. Therefore, a construct (PHELLSGATE) was made to take advantage of Gateway™ (Life Technologies). With this technology, a PCR fragment is generated, bordered with recombination sites (attB1 and attB2) which is directionally recombined, in vitro, into a plasmid containing two sets of suitable recombination sites (attP1 and attP2 sites) using the commercially available recombination protein preparation.

The pHELLSGATE vector was designed such that a single PCR product from primers with the appropriate attB1 and attB2 sites would be recombined into it simultaneously to form the two arms of the hairpin. The ccdB gene, which is lethal in standard *E. coli* strains such as DH5α (but not in DB3.1), was placed in the locations to be replaced by the arm sequences, ensuring that only recombinants containing both arms would be recovered. Placing a chloramphenicol resistance gene within the intron, gives a selection to ensure the retention of the intron in the recombinant plasmid.

pHELLSGATE comprises the following DNA fragments:
a spectinomycin/streptomycin resistance gene (SEQ ID No 13 from the nucleotide at position 7922 to the nucleotide sequence at 9985);
a right T-DNA border sequence (SEQ ID No 13 from the nucleotide at position 10706 to the nucleotide sequence at 11324);
a CaMV35S promoter (SEQ ID No 13 from the nucleotide at position 11674 to the nucleotide sequence at 13019);
an attP1 recombination site (complement of the nucleotide sequence of SEQ ID No 13 from the nucleotide at position 17659 to the nucleotide sequence at 17890);
a ccdB selection marker (complement of the nucleotide sequence of SEQ ID No 13 from the nucleotide at position 16855 to the nucleotide at position 17610);
an attP2 recombination site (complement of the nucleotide sequence of SEQ ID No 13 from the nucleotide at position 16319 to the nucleotide at position 16551);
pdk intron2 (SEQ ID No 13 from the nucleotide at position 14660 to the nucleotide at position 16258) flanked by the intron splice site (TACAG*TT (SEQ ID No 13 from the nucleotide at position 16254 to the nucleotide sequence at 16260) and the intron splice site (TG*GTAAG) (SEQ ID No 13 from the nucleotide at position 14660 to the nucleotide sequence at 14667) and comprising a chloramphenicol resistance gene (SEQ ID No 13 from the nucleotide at position 15002 to the nucleotide at position 15661);
an attP2 recombination site (SEQ ID No 13 from the nucleotide at position 14387 to the nucleotide at position 14619);
a ccdB selection marker (complement of the nucleotide sequence of SEQ ID No 13 from the nucleotide at position 13675 to the nucleotide at position 13980);
an attP1 recombination site (SEQ ID No 13 from the nucleotide at position 13048 to the nucleotide at position 13279);
an octopine synthase gene terminator region (SEQ ID No 13 from the nucleotide at position 17922 to the nucleotide sequence at 18687);
a chimeric marker selectable in plants comprising:
a nopaline synthase promoter (SEQ ID No 13 from the nucleotide at position 264 to the nucleotide sequence at 496);
a nptII coding region (SEQ ID No 13 from the nucleotide at position 497 to the nucleotide sequence at 1442); and
a nopaline synthase gene terminator (SEQ ID No 13 from the nucleotide at position 1443 to the nucleotide sequence at 2148);
a left T-DNA border sequence (SEQ ID No 13 from the nucleotide at position 2149 to the nucleotide sequence at 2706);
an origin of replication; and
a kanamycin resistance gene;

The complete nucleotide sequence of pHELLSGATE is represented in the sequence listing (SEQ ID No 13) and a schematic figure can be found in FIG. 3.

Example 2

Use of the pHELLSGATE to Convert Nucleic Acid Fragments of Interest into dsRNA Producing Chimeric Silencing Genes.

To test the acceptor vector pHELLSGATE, about 400 bp, 200 bp, 100 bp, 50 bp and 25 bp fragments of the *Arabidopsis thaliana* chalcone synthase isomerase coding sequence (SEQ ID No 12) (having respectively the nucleotide sequence of SEQ ID No 12 from the nucleotide at position 83 to the nucleotide at position 482; the nucleotide sequence of SEQ ID No 12 from the nucleotide at position 83 to the nucleotide at position 222; the nucleotide sequence of SEQ ID No 12 from the nucleotide at position 83 to the nucleotide at position 182; the nucleotide sequence of SEQ ID No 12 from the nucleotide at position 83 to the nucleotide at position 132; and the nucleotide sequence of SEQ ID No 12 from the nucleotide at position 83 to the nucleotide at position 107) were used as nucleic acid fragments of insert for construction of chimeric genes capable of producing dsRNA.

This gene was chosen because its mutant allele has been reported in *Arabidopsis* to give distinct phenotypes. The CHS tt4(85) EMS mutant (Koornneef, 1990) produces inactive CHS resulting in no anthocyanin pigment in either the stem or seed-coat. Wildtype plants produce the purple-red pigment in both tissues.

In a first step, the respective fragments were PCR amplified using specific primers further comprising attB1 and attB2 recombination sites. AttB1 and attB2 specific primers were purchased from Life Technologies. The 25 and 50 bp fragments flanked by att sites were made by dimerization of the primers.

The following combinations of primers were used:

For the 400 bp fragment:

Forward Primer:

GGGGACAAGTTTGTACAAAAAAGCAGGCTGCACTGC (SEQ ID No 14) TAACCCTGAGAACCATGTGCTTC;

Reverse Primer:

GGGGACCACTTTGTACAAGAAAGCTGGGTCGCTTGA (SEQ ID No 15) CGGAAGGACGGAGACCAAGAAGC.

For the 200 bp fragment:

Forward Primer:

GGGGACAAGTTTGTACAAAAAAGCAGGCTGCACTGC (SEQ ID No 14) TAACCCTGAGAACCATGTGCTTC;

Reverse Primer:

GGGGACCACTTTGTACAAGAAAGCTGGGTAGGAGCC (SEQ ID No 16) ATGTAAGCACACATGTGTGGGTT.

For the 100 bp fragment:

Forward Primer:

GGGGACAAGTTTGTACAAAAAAGCAGGCTGCACTGC (SEQ ID No 17) TAACCCTGAGAACCATGTGCTTCAGGCGGAGTATCC TGACTACTACTTCCGCATCACCAACAGT;

Reverse Primer:

GGGGACCACTTTGTACAAGAAAGCTGGGTAACTTCT (SEQ ID No 18) CCTTGAGGTCGGTCATGTGTTCACTGTTGGTGATGC GGAAGTAGTAGTCAGGATACTCCGCCTG.

For the 50 bp fragment:

Forward Primer:

GGGGACAAGTTTGTACAAAAAAGCAGGCTGCACTGC (SEQ ID No 19) TAACCCTGAGAACCATGTGCTTCAGGCGGAGTATCC TGACTAC;

Reverse Primer:

GGGGACCACTTTGTACAAGAAAGCTGGGTGTAGTCA (SEQ ID No 20) GGATACTCCGCCTGAAGCACATGGTTCTCAGGGTTA GCAGTGC.

For the 25 bp fragment:

Forward Primer:

GGGGACAAGTTTGTACAAAAAAGCAGGCTGCACTGC (SEQ ID No 21) TAACCCTGAGAACCATGT;

Reverse Primer:

GGGGACCACTTTGTACAAGAAAGCTGGGTACATGGT (SEQ ID No 22) TCTCAGGGTTAGCAGTGC.

PCR amplification and recombination using the GATEWAY™ technology with the commercially available BP Clonase (Life Technologies) were performed according to the manufacturer's instructions.

Bacterial colonies obtained on chloramphenicol-containing plates spread with *E. coli* DH5α bacteria, transformed (by electroporation or by heatshocking RbCl2 treated competent *E. coli* cells) with the in vitro recombination reaction were screened. Colonies containing the desired recombinant plasmid were obtained in each case. For the about 400 bp fragment, 24 colonies were screened and 23 contained the desired construct with the 400 bp in inverted repeat, operably linked to the CaMV35S promoter. For the about 200 bp fragment, 36 colonies were screened and 35 contained the desired construct with the 200 bp in inverted repeat, operably linked to the CaMV35S promoter. For the about 50 bp fragment, six colonies were screened and four contained the desired construct with the 50 bp in inverted repeat, operably linked to the CaMV35S promoter. For the 25 bp fragment, six colonies were screened and one contained the desired construct with the 400 bp in inverted repeat, operably linked to the CaMV35S promoter. In a number of cases, the structure was confirmed by sequence analysis.

These results show that this vector facilitates the rapid, efficient, and simple production of hpRNA (hairpin RNA constructs). pHELLSGATE is a T-DNA vector, with a high-copy-number origin of replication for ease of handling. Recombinant pHELLSGATE constructs can be directly transformed into *Agrobacterium* for transformation of the chimeric construct into plants. This system can be used in high throughput applications.

Example 3

Evaluation of Plants Comprising the Chimeric Genes of Example 2.

The vectors containing the dsRNA producing chimeric constructs with the 400, 200, 100, 50 and 25 nucleotides of chalcone synthase in inverted repeat (Example 2) were introduced into *Agrobacterium tumefaciens* strain AGL1, GV3101 or LBA4404 either by electroporation or tri-parental mating.

Transgenic *Arabidopsis* lines are obtained by transformation with these *Agrobacteria* using the dipping method of Clough and Bent (1998).

Chalcone synthase activity is monitored by visual observation of stem and leaf color (normally in plants grown under high light, and by unaided or microscope assisted visual observation of seed-coat color.

Most of the transgenic lines transformed with the abovementioned CHS silencing constructs show pronounced silencing. The seed color of most of these lines is virtually indistinguishable from seed of the tt4(85) mutant to the naked eye. Examination of the seed under a light microscope reveals that the degree of pigmentation is generally uniform in the cells of the coat of an individual seed, and among seeds of the same line.

Example 4

Construction of the Acceptor Vectors pHELLSGATE 4, pHELLSGATE 8, pHELLSGATE 11 and pHELLSGATE 12.

pHELLSGATE 4 was made by excising the DNA fragment comprising the pdk intron and chloramphenicol resistance gene from pHellsgate (Example 1) with HindIII and EcoRI and replacing it with a HindIII/EcoRI DNA fragment containing only the pdk intron. The complete nucleotide sequence of pHELLSGATE 4 is represented in the sequence listing (SEQ ID No 23).

pHellsgate 8 was made by PCR amplification using pHellsgate DNA as a template and oligonucleotides with the sequence 5'GGGCTCGAGACAAGTTTGTA-CAAAAMGCTG 3' and 5'GGCTCGAGACCACTTTGTA-CAAGAAAGC 3' as primers. These primers modify the attP sites within pHellsgate to attR sites. The resulting fragment was sequenced and inserted into the XhoI site of a vector upstream of a DNA fragment containing the pdk intron fragment. Similarly an XbaI/XbaI fragment amplified with the oligonucleotides 5'GGGTCTAGACAAGTTTGTA-CAAAAAAGCTG 3' and 5'GGGTCTAGACCACTTTGTA-CAAGAAAGC 3' as primers and pHELLSGATE as template DNA to modify the attP sites of this cassette to attR sites. This fragment was sequenced and inserted into the XbaI site of the intermediate described above downstream of the pdk intron. The complete nucleotide sequence of pHELLSGATE 8 is represented in the sequence listing (SEQ ID No 24) and a schematic figure can be found in FIG. 4.

pHELLSGATE 11 is similar to pHELLSGATE 8 except that the pdk intron has been engineered to contain a branching point in the complementary strand such that splicing of the intron is independent of its orientation (a so-called "two-way intron"). The complete nucleotide sequence of pHELLS-GATE 11 is represented in the sequence listing (SEQ ID No 25) and a schematic representation thereof can be found in FIG. 4.

pHELLSGATE 12 is also similar to pHELLSGATE 8 except that the pdk intron has been duplicated as an inverted repeat. The complete nucleotide sequence of pHELLSGATE 12 is represented in the sequence listing (SEQ ID No 26) and a schematic representation thereof can be found in FIG. 4.

Example 5

Use of the Different pHELLSGATE Vectors to Generate dsRNA Chimeric Silencing Genes Targeted Towards Three Different Model Target Genes.

The efficiency in gene silencing of the different pHELLS-GATE vectors was tested by inserting fragments of three target genes: Flowering locus C (FLC); Ethylene insensitive 2 (EIN2); and Phytoene desaturase (PDC). For FLC a 390 bp fragment was used (from the nucleotide at position 303 to the nucleotide at position 692 of the nucleotide sequence available as Genbank Accession Nr AF116527). For EIN2 a 580 bp fragment was used (from the nucleotide at position 541 to the nucleotide at position 1120 of the nucleotide sequence available as Genbank Accession Nr AF141203). For PDS a 432 bp fragment was used (from the nucleotide at position 1027 to the nucleotide at position 1458 of the nucleotide sequence available as Genbank Accession Nr L16237). Genes of interest were amplified using gene specific primers with either a 5' attB1 extension (GGGGACAAGTTTGTA-CAAAAAAGCAGGCT) or an attB2 extension (GGGAC-CACTTTGTACAAGAAAGCTGGGT) using F1 Taq DNA polymerase (Fisher Biotec, Subiaco, Wash., Australia) according to the manufacturer's protocol. PCR products were precipitated by adding 3 volumes TE and two volumes 30% (w/v) PEG 3000, 30 mM $MgCl_2$ and centrifuging at 13000 g for 15 minutes.

Recombination reaction of PCR products with either pDONR201 (Invitrogen, Groningen, The Netherlands) or pHellsgate 4 were carried out in a total volume of 10 μL with 2 μL BP clonase buffer (Invitrogen), 1-2 μL PCR product 150 ng plasmid vector and 2 μL BP clonase (Invitrogen). The reaction was incubated at room temperature (25° C.) for 1 h to overnight. After the incubation, 1 μL proteinase K (2 μg/μL; Invitrogen) was added and incubated for 10 min at 37° C. 1-2 μL of the mix was used to transform DH5α; colonies were selected on the appropriate antibiotics. Clones were checked either by digestion of DNA minipreps or PCR. Recombination reactions from pDONR201 clones to pHellsgate 8, 11 or 12 were carried out in 10 μL total volume with 2 μL LR clonase buffer (Invitrogen), 2 μL pDONR201 clone (approximately 150 ng), 300 ng pHellsgate 8, 11 or 12 and 2 μL LR clonase (Invitrogen). The reaction was incubated overnight at room temperature, proteinase-treated and used to transform *E. coli* DH5α as for the BP clonase reaction.

Transformation of *Arabidopsis* was performed according to via the floral dip method (Clough and Bent, 1998). Plants were selected on agar solidified MS media supplemented with 100 mgA timentin and 50 mgA kanamycin. For FLC and PDS constructs, the C24 ecotype was used; for EIN2 constructs, Landsberg erecta was used. For scoring of EIN2 phenotypes, transformed T1 plants were transferred to MS media containing 50 μM 1-aminocyclopropane-1-carboxylic acid (ACC) together with homozygous EIN2-silenced lines and wild type Landberg erecta plants. T1 FLC hpRNA plants were scored by transferring to MS plates and scoring days to flower or rosette leaves at flowering compared to C24 wild type plants and flc mutant lines. T1 PDS hpRNA plants were scored by looking at bleaching of the leaves. The results of the analysis of plants transformed with the different pHELLS-GATE vectors are shown in Table 1.

All plants transformed with pHellsgate 4-FLC and pHellsgate 8-FLC flowered significantly earlier than wildtype C24 and in both cases plants flowering with the same number of rosette leaves as the flc-20 line (carrying a stable Ds insertion in the first intron of the FLC gene) were observed. There was no clear difference in rosette leaves at flowering between the sets of plants transformed with the pHellsgate 4-FLC and pHellsgate 8-FLC constructs.

A difference in the effectiveness of the pHellsgate 4-EIN2 and pHellsgate 8-EIN2 plants was observed. Of 36 transformants for pHG4-EIN2, there were no plants with an observable ACC-resistant phenotype under the conditions used for this experiment, whereas eight of the 11 plants carrying the pHG8-EIN2 transgene showed some degree of ACC-resistance. The extent to which the pHG8-EIN2 plants were resistant to ACC was variable indicating that the severity of silencing varies between transformants.

The great majority of plants carrying pHG4-PDS and pHG8-PDS showed a phenotype consistent with the loss of photoprotection due to the absence of carotenoids. The weakest phenotype was a bleaching of the cotyledons, with the true leaves not bleaching at any stage in the life cycle. The bleached cotyledon phenotype was only seen in plants transformed with PDS hpRNA constructs; we confirmed that the plants with this phenotype also contained the PDS hpRNA construct (data not shown) strongly suggesting that this phenotype is due to PDS silencing and not bleaching from the kanamycin selection. Plants transformed with the pHellsgate 4-PDS construct gave only this weak bleached cotyledon phenotype. In contrast, the five of the pHellsgate 8-PDS plants had the weak phenotype and three showed a stronger phenotype with extensive or complete bleaching of the true leaves.

TABLE 1

| Construct | Test genes | T1 plants | Rate of silencing |
|---|---|---|---|
| HELLSGATE 4 | FLC | 13 | 12 |
| | EIN2 | 36 | 0 |
| | PDS | 12 | 11 |
| HELLSGATE 8 | FLC | 6 | 6 |
| | EIN2 | 11 | 8 |
| | PDS | 9 | 8 |

TABLE 1-continued

| Construct | Test genes | T1 plants | Rate of silencing |
|---|---|---|---|
| HELLSGATE 11 | FLC | 2 | 2 |
| | EIN2 | 30 | 11 |
| | PDS | 11 | 11 |
| HELLSGATE 11 (intervening region in inverse orientation) | FLC | 8 | 6 |
| | EIN2 | | |
| | PDS | | |
| HELLSGATE 12 | FLC | 13 | 11 |
| | EIN2 | 26 | 12 |
| | PDS | | |
| HELLSGATE 12 (intervening region in inverse orientation) | FLC | 9 | 8 |
| | EIN2 | 5 | 2 |
| | PDS | | |
| | CHS | | |

REFERENCES

An et al. (1996) *The Plant Cell* 8, 15-30
AzpiroLeehan and Feldmann (1997) *Trends Genet* 13: 152-156
Clough and Bent (1998) *Plant J.* 16: 735-743
Fire et al. (1998) *Nature* 391: 806-811
Fromm et al. (1990) *Bio/Technology* 8: 833
Gordon-Kamm et al. (1990) *The Plant Cell* 2: 603
Hamilton et al. (1998) *Plant J.* 15: 737-746
Hoess et al. (1986) *Nucl. Acids Res.* 14: 2287
Hudspeth et al. (1989) *Plant Mol. Biol.* 12: 579-589
Keil et al. (1989) *EMBO J.* 8: 1323-1330
Keller et al. (1988) *EMBO J.* 7: 3625-3633
Keller et al. (1989) *Genes & Devel.* 3: 1639-1646
Koornneef (1990) *Theor. Appl. Gen.* 80: 852-857
Landy (1993) *Current Opinions in Genetics and Development* 3: 699-707
Landy (1989) *Ann. Rev. Biochem.* 58: 913
Martienssen (1998) *Proc. Natl. Acad. Sci. USA* 95: 2021-2026
Meyer et al. (1987) *Nature* 330: 677
Needleman and Wunsch (1970) *J. Mol. Biol.* 48: 443453
Peleman et al. (1989) *Gene* 85: 359-369
Ross-MacDonald et al. (1999) *Nature* 402: 413-418
Smith et al. (2000) *Nature* 407: 319-320
Wagner and Sun (1998) *Nature* 391: 744-745
Waterhouse et al (1998) *Proc. Natl. Acad. Sci. USA* 95: 13959-13964

We claim:

1. A method for preparing a plant comprising a final chimeric DNA construct, said method comprising:

preparing a final chimeric DNA construct capable of expressing a dsRNA of interest in a plant cell; said final chimeric DNA construct of interest comprising a DNA of interest (12) comprising a nucleotide sequence encoding said dsRNA of interest according to a method comprising the steps of combining in vitro a vector, an insert DNA and at least one site specific recombinase protein, said vector comprising the following operably linked DNA fragments:

an origin of replication allowing replication in a recipient cell (1), a selectable marker region (2) capable of being expressed in said recipient cell; and a first chimeric DNA construct comprising in sequence:

a promoter or promoter region (3) capable of being recognized by RNA polymerases of a plant cell;

a first recombination site (4), a second recombination site (5), a third recombination site (6) and a fourth recombination site (7);

a 3' transcription terminating and polyadenylation region (8) functional in said plant cell;

wherein said first recombination site (4) and said fourth recombination site (7) are capable of reacting with a same recombination site, and said second recombination site (5) and said third recombination site (6), are capable of reacting with a same recombination site;

and wherein said first recombination site (4) and said second recombination site (5) do not recombine with each other or with a same recombination site; or said third recombination site (6) and said fourth recombination site (7) do not recombine with each other or with a same recombination site;

said insert DNA comprising said DNA segment of interest (12) flanked by a fifth recombination site (13) which is capable of recombining with said first (4) or fourth (7) recombination site on said vector; and a sixth recombination site (14) which is capable of recombining with said second (5) or third (6) recombination site on said vector;

said at least one site specific recombination protein being capable of recombining said first (4) or fourth (7) and said fifth (13) recombination site and said second (5) or third (6) and said sixth (14) recombination site;

allowing recombination to occur so as to produce a reaction mixture comprising product DNA molecules, said product DNA molecule comprising in sequence:

said promoter or promoter region (3) capable of being recognized by RNA polymerases of said plant cell;

a recombination site (15) which is the recombination product of said first (4) and said fifth (13) recombination site;

said DNA fragment of interest (12);

a recombination site (16) which is the recombination product of said second (4) and said sixth (14) recombination site;

a recombination site (17) which is the recombination product of said third (5) and said sixth (14) recombination site;

said DNA fragment of interest in opposite orientation (12);

a recombination site (18) which is the recombination product of said fourth (7) and said fifth (13) recombination site; and said 3' transcription terminating and polyadenylation region (8) functional in said plant cell;

selecting said product DNA molecules comprising said final chimeric DNA construct; and introducing said final chimeric DNA construct into at least one cell of said plant thereby preparing a plant comprising said final chimeric DNA construct.

2. A plant obtained through the method of claim 1.

3. The method according to claim 1, wherein said first (4) and second recombination site (5) flank a second selectable marker gene (10) and said third (6) and fourth recombination site (7) flank a third selectable marker gene (9).

4. The method according to claim 1 wherein said first chimeric DNA construct comprises a region flanked by intron processing signals (11), functional in said plant cell, located between said second recombination site (5) and said third recombination site (6).

5. The method according to claim 4 wherein said region flanked by intron processing signals is an intron sequence functional in said plant cell.

6. The method according to claim 4 wherein said vector further comprises a fourth selectable marker gene (19), located between said second (5) and third (6) recombination site.

7. The method according to claim 1, wherein said vector comprises a selectable marker gene selected from the group consisting of an antibiotic resistance gene, a tRNA gene, an auxotrophic marker, a toxic gene, a phenotypic marker, an antisense oligonucleotide; a restriction endonuclease; a restriction endonuclease cleavage site, an enzyme cleavage site, a protein binding site, an a sequence complementary PCR primer.

8. The method according to claim 1, wherein said wherein said promoter (3) of said vector is a plant-expressible promoter.

9. The method according to claim 1, wherein said first chimeric DNA construct is flanked by left and right border T-DNA sequences.

10. The method according to claim 1 wherein said vector further comprises a selectable marker gene capable of being expressed in plant cells located between said left and said right T-DNA border sequences.

11. The method according to claim 1, wherein said vector of claim 8, further comprises an origin of replication capable of functioning in *Agrobacterium* sp.

12. The method according to claim 1, wherein said first (4) and fourth (7) recombination site is attR1 comprising the nucleotide sequence of SEQ ID No 4 and said second (5) and third (6) recombination site is attR2 comprising the nucleotide sequence of SEQ ID No 5.

13. The method according to claim 1, wherein said first (4) and fourth (7) recombination site is attP1 comprising the nucleotide sequence of SEQ ID No 10 and said second (5) and third (6) recombination site is attP2 comprising the nucleotide sequence of SEQ ID No 11.

14. The method according to claim 1, wherein said vector comprises the sequence of SEQ ID No 13.

15. The method according to claim 1, wherein said vector comprises the sequence of SEQ ID No 23.

16. The method according to claim 1, wherein said vector comprises the sequence of SEQ ID No 24.

17. The method according to claim 1, wherein said vector comprises the sequence of SEQ ID No 25.

18. The method according to claim 1, wherein said vector comprises the sequence of SEQ ID No 26.

19. The method according to claim 1, wherein said insert DNA is a linear DNA molecule.

20. The method according to claim 1, wherein said insert DNA is a circular DNA molecule.

21. The method according to claim 1, wherein said at least one recombination protein is selected from (i) Int (λ integrase) and IHF (integration host factor) and (ii) Int, Xis (λ excisionase), and IHF.

* * * * *

SEQUENCE LISTING

<160> NUMBER OF SEQ ID NOS: 26

<210> SEQ ID NO 1
<211> LENGTH: 25
<212> TYPE: DNA
<213> ORGANISM: Artificial sequence
<220> FEATURE:
<223> OTHER INFORMATION: core sequence of recombination site attB1

<400> SEQUENCE: 1
agcctgcttt tttgtacaaa cttgt                                    25

```
<210> SEQ ID NO 2
<211> LENGTH: 25
<212> TYPE: DNA
<213> ORGANISM: Artificial sequence
<220> FEATURE:
<223> OTHER INFORMATION: core sequence of recombination site attB2

<400> SEQUENCE: 2
agcctgcttt cttgtacaaa cttgt                                              25

<210> SEQ ID NO 3
<211> LENGTH: 25
<212> TYPE: DNA
<213> ORGANISM: Artificial sequence
<220> FEATURE:
<223> OTHER INFORMATION: core sequence of recombination site attB3

<400> SEQUENCE: 3
acccagcttt cttgtacaaa cttgt                                              25

<210> SEQ ID NO 4
<211> LENGTH: 25
<212> TYPE: DNA
<213> ORGANISM: Artificial sequence
<220> FEATURE:
<223> OTHER INFORMATION: core sequence of recombination site attR1

<400> SEQUENCE: 4
gttcagcttt tttgtacaaa cttgt                                              25

<210> SEQ ID NO 5
<211> LENGTH: 25
<212> TYPE: DNA
<213> ORGANISM: Artificial sequence
<220> FEATURE:
<223> OTHER INFORMATION: core sequence of recombination site attR2

<400> SEQUENCE: 5
gttcagcttt cttgtacaaa cttgt                                              25

<210> SEQ ID NO 6
<211> LENGTH: 25
<212> TYPE: DNA
<213> ORGANISM: Artificial sequence
<220> FEATURE:
<223> OTHER INFORMATION: core sequence of recombination site attR3

<400> SEQUENCE: 6
gttcagcttt cttgtacaaa gttgg                                              25

<210> SEQ ID NO 7
<211> LENGTH: 25
<212> TYPE: DNA
<213> ORGANISM: Artificial sequence
<220> FEATURE:
<223> OTHER INFORMATION: core sequence of recombination site attL1

<400> SEQUENCE: 7
agcctgcttt tttgtacaaa gttgg                                              25

<210> SEQ ID NO 8
<211> LENGTH: 25
<212> TYPE: DNA
<213> ORGANISM: Artificial sequence
<220> FEATURE:
<223> OTHER INFORMATION: core sequence of recombination site attL2
```

```
<400> SEQUENCE: 8
agcctgcttt cttgtacaaa gttgg                                              25

<210> SEQ ID NO 9
<211> LENGTH: 25
<212> TYPE: DNA
<213> ORGANISM: Artificial sequence
<220> FEATURE:
<223> OTHER INFORMATION: core sequence of recombination site attL3

<400> SEQUENCE: 9
acccagcttt cttgtacaaa gttgg                                              25

<210> SEQ ID NO 10
<211> LENGTH: 25
<212> TYPE: DNA
<213> ORGANISM: Artificial sequence
<220> FEATURE:
<223> OTHER INFORMATION: core sequence of recombination site attP1

<400> SEQUENCE: 10
gttcagcttt tttgtacaaa gttgg                                              25

<210> SEQ ID NO 11
<211> LENGTH: 25
<212> TYPE: DNA
<213> ORGANISM: Artificial sequence
<220> FEATURE:
<223> OTHER INFORMATION: core sequence of recombination site attP2,P3

<400> SEQUENCE: 11
gttcagcttt cttgtacaaa gttgg                                              25

<210> SEQ ID NO 12
<211> LENGTH: 1188
<212> TYPE: DNA
<213> ORGANISM: Artificial sequence
<220> FEATURE:
<223> OTHER INFORMATION: cDNA sequence of the Arabidopsis thaliana
      chalcone synthase coding region

<400> SEQUENCE: 12
atggtgatgg ctggtgcttc ttctttggat gagatcagac aggctcagag agctgatgga     60
cctgcaggca tcttggctat tggcactgct aaccctgaga accatgtgct tcaggcggag    120
tatcctgact actacttccg catcaccaac agtgaacaca tgaccgacct caaggagaag    180
ttcaagcgca tgtgcgacaa gtcgacaatt cggaaacgtc acatgcatct gacggaggaa    240
ttcctcaagg aaaacccaca catgtgtgct tacatggctc cttctctgga caccagacag    300
gacatcgtgg tggtcgaagt ccctaagcta ggcaaagaag cggcagtgaa ggccatcaag    360
gagtggggcc agcccaagtc aaagatcact catgtcgtct tctgcactac ctccggcgtc    420
gacatgcctg gtgctgacta ccagctcacc aagcttcttg gtctccgtcc ttccgtcaag    480
cgtctcatga tgtaccagca aggttgcttc gccggcggta ctgtcctccg tatcgctaag    540
gatctcgccg agaacaaccg tggagcacgt gtcctcgttg tctgctctga gatcacagcc    600
gttaccttcc gtggtccctc tgacacccac cttgactccc tcgtcggtca ggctcttttc    660
agtgatggcg ccgccgcact cattgtgggg tcggaccctg acacatctgt cggagagaaa    720
cccatctttg agatggtgtc tgccgctcag accatccttc cagactctga tggtgccata    780
gacggacatt tgagggaagt tggtctcacc ttccatctcc tcaaggatgt tcccggcctc    840
```

```
atctccaaga acattgtgaa gagtctagac gaagcgttta aacctttggg gataagtgac    900
tggaactccc tcttctggat agcccaccct ggaggtccag cgatcctaga ccaggtggag    960
ataaagctag gactaaagga agagaagatg agggcgacac gtcacgtgtt gagcgagtat   1020
ggaaacatgt cgagcgcgtg cgttctcttc atactagacg agatgaggag gaagtcagct   1080
aaggatggtg tggccacgac aggagaaggg ttggagtggg gtgtcttgtt tggtttcgga   1140
ccaggtctca ctgttgagac agtcgtcttg cacagcgttc ctctctaa                1188
```

```
<210> SEQ ID NO 13
<211> LENGTH: 18691
<212> TYPE: DNA
<213> ORGANISM: Artificial sequence
<220> FEATURE:
<223> OTHER INFORMATION: acceptor vector pHELLSGATE
<220> FEATURE:
<221> NAME/KEY: misc_feature
<222> LOCATION: (7922)..(9985)
<223> OTHER INFORMATION: spectinomycin resistance
<220> FEATURE:
<221> NAME/KEY: misc_feature
<222> LOCATION: (10706)..(11324)
<223> OTHER INFORMATION: right T-DNA border fragment
<220> FEATURE:
<221> NAME/KEY: misc_feature
<222> LOCATION: (11674)..(13019)
<223> OTHER INFORMATION: CaMV35S promoter fragment
<220> FEATURE:
<221> NAME/KEY: misc_feature
<222> LOCATION: (17890)..(17659)
<223> OTHER INFORMATION: attP1 recombination site (complement)
<220> FEATURE:
<221> NAME/KEY: misc_feature
<222> LOCATION: (17610)..(16855)
<223> OTHER INFORMATION: ccdB selection marker (complement)
<220> FEATURE:
<221> NAME/KEY: misc_feature
<222> LOCATION: (16551)..(16319)
<223> OTHER INFORMATION: attP2 recombination site (complement)
<220> FEATURE:
<221> NAME/KEY: misc_feature
<222> LOCATION: (14660)..(16258)
<223> OTHER INFORMATION: pdk2 intron 2
<220> FEATURE:
<221> NAME/KEY: misc_feature
<222> LOCATION: (15002)..(15661)
<223> OTHER INFORMATION: chloramphenicol resistance gene
<220> FEATURE:
<221> NAME/KEY: misc_feature
<222> LOCATION: (14387)..(14619)
<223> OTHER INFORMATION: attP2 recombination site
<220> FEATURE:
<221> NAME/KEY: misc_feature
<222> LOCATION: (13675)..(13980)
<223> OTHER INFORMATION: ccdB selection marker (complement)
<220> FEATURE:
<221> NAME/KEY: misc_feature
<222> LOCATION: (13048)..(13279)
<223> OTHER INFORMATION: attP1 recombination site
<220> FEATURE:
<221> NAME/KEY: misc_feature
<222> LOCATION: (17922)..(18687)
<223> OTHER INFORMATION: octopine synthase gene terminator region
<220> FEATURE:
<221> NAME/KEY: misc_feature
<222> LOCATION: (264)..(496)
<223> OTHER INFORMATION: nopaline synthase gene promoter
<220> FEATURE:
<221> NAME/KEY: misc_feature
<222> LOCATION: (497)..(1442)
<223> OTHER INFORMATION: nptII coding region
<220> FEATURE:
<221> NAME/KEY: misc_feature
<222> LOCATION: (1443)..(2148)
<223> OTHER INFORMATION: nopaline synthase gene terminator
```

```
<220> FEATURE:
<221> NAME/KEY: misc_feature
<222> LOCATION: (2149)..(2706)
<223> OTHER INFORMATION: a left T-DNA border region

<400> SEQUENCE: 13
ggccgcacta gtgatatccc gcggccatgg cggccgggag catgcgacgt cgggcccaat      60
tcgccctata gtgagtcgta ttacaattca ctggccgtcg ttttacaacg tcgtgactgg     120
gaaaaccctg gcgttaccca acttaatcgc cttgcagcac atccccettt cgccagctgg     180 cgtaatagcg aagaggcccg caccgatcgc ccttcccaac agttgcgcag cctgaatggc     240
gaatggaaat tgtaaacgtt aatgggtttc tggagtttaa tgagctaagc acatacgtca     300
gaaaccatta ttgcgcgttc aaaagtcgcc taaggtcact atcagctagc aaatatttct     360
tgtcaaaaat gctccactga cgttccataa attcccctcg gtatccaatt agagtctcat     420
attcactctc aatccaaata atctgcaatg caattaccct atccgcaac ttctttacct     480 atttccgccc ggatccgggc aggttctccg gccgcttggg tggagaggct attcggctat     540
gactgggcac aacagacaat cggctgctct gatgccgccg tgttccggct gtcagcgcag     600
gggcgcccgg ttcttttttgt caagaccgac ctgtccggtg ccctgaatga actgcaggac     660
gaggcagcgc ggctatcgtg gctggccacg acgggcgttc cttgcgcagc tgtgctcgac     720
gttgtcactg aagcgggaag ggactggctg ctattgggcg aagtgccggg gcaggatctc     780
ctgtcatctc accttgctcc tgccgagaaa gtatccatca tggctgatgc aatgcggcgg     840
ctgcatacgc ttgatccggc tacctgccca ttcgaccacc aagcgaaaca tcgcatcgag     900
cgagcacgta ctcggatgga agccggtctt gtcgatcagg atgatctgga cgaagagcat     960 cagggggctcg cgccagccga actgttcgcc aggctcaagg cgcgcatgcc cgacggcgag    1020
gatctcgtcg tgacccatgg cgatgcctgc ttgccgaata tcatggtgga aaatggccgc    1080
ttttctggat tcatcgactg tggccggctg ggtgtggcgg accgctatca ggacatagcg    1140
ttggctaccc gtgatattgc tgaagagctt ggcggcgaat gggctgaccg cttcctcgtg    1200 cttttacggta tcgccgctcc cgattcgcag cgcatcgcct tctatcgcct tcttgacgag    1260
ttcttctgag cgggactctg ggttcgaaa tgaccgacca agcgacgccc aacctgccat    1320
cacgagattt cgattccacc gccgccttct atgaaaggtt gggcttcgga atcgttttcc    1380
gggacgccgg ctggatgatc ctccagcgcg ggatctcat gctggagttc ttcgcccacc    1440
ccgatccaac acttacgttt gcaacgtcca agagcaaata gaccacgaac gccggaaggt    1500
tgccgcagcg tgtggattgc gtctcaattc tctcttgcag gaatgcaatg atgaatatga    1560
tactgactat gaaactttga gggaatactg cctagcaccg tcacctcata acgtgcatca    1620
tgcatgccct gacaacatgg aacatcgcta tttttctgaa gaattatgct cgttggagga    1680
tgtcgcggca attgcagcta ttgccaacat cgaactaccc ctcacgcatg cattcatcaa    1740
tattattcat gcggggaaag gcaagattaa tccaactggc aaatcatcca gcgtgattgg    1800
taacttcagt tccagcgact tgattcgttt tggtgctacc cacgttttca ataaggacga    1860
gatggtggag taagaagga gtgcgtcgaa gcagatcgtt caaacatttg gcaataaagt    1920
ttcttaagat tgaatcctgt tgccggtctt gcgatgatta tcatataatt tctgttgaat    1980
tacgttaagc atgtaataat taacatgtaa tgcatgacgt tatttatgag atgggttttt    2040
atgattagag tcccgcaatt atacatttaa tacgcgatag aaaacaaaat atagcgcgca    2100
aactaggata aattatcgcg cgcggtgtca tctatgttac tagatcgaat taattccagg    2160
```

-continued

```
cggtgaaggg caatcagctg ttgcccgtct cactggtgaa agaaaaaacc accccagtac    2220
attaaaaacg tccgcaatgt gttattaagt tgtctaagcg tcaatttgtt tacaccacaa    2280
tatatcctgc caccagccag ccaacagctc cccgaccggc agctcggcac aaaatcacca    2340
ctcgatacag gcagcccatc agtccgggac ggcgtcagcg ggagagccgt tgtaaggcgg    2400
cagactttgc tcatgttacc gatgctattc ggaagaacgg caactaagct gccgggtttg    2460
aaacacggat gatctcgcgg agggtagcat gttgattgta acgatgacag agcgttgctg    2520
cctgtgatca aatatcatct ccctcgcaga gatccgaatt atcagccttc ttattcattt    2580
ctcgcttaac cgtgacaggc tgtcgatctt gagaactatg ccgacataat aggaaatcgc    2640
tggataaagc cgctgaggaa gctgagtggc gctatttctt tagaagtgaa cgttgacgat    2700
gtcgacggat cttttccgct gcataaccct gcttcgcgcc cattatagcg atttttccgg    2760
tatatccatc cttttcgca cgatatacag gattttgcca aagggttcgt gtagactttc    2820
cttggtgtat ccaacggcgt cagccgggca ggataggtga agtaggccca cccgcgagcg    2880
ggtgttcctt cttcactgtc ccttattcgc acctggcggt gctcaacggg aatcctgctc    2940
tgcgaggctg gccggctacc gccggcgtaa cagatgaggg caagcggatg gctgatgaaa    3000
ccaagccaac caggggtgat gctgccaact tactgattta gtgtatgatg gtgttttga    3060 ggtgctccag tggcttctgt ttctatcagc tgtccctcct gttcagctac tgacggggtg    3120
gtgcgtaacg gcaaaagcac cgccggacat cagcgctatc tctgctctca ctgccgtaaa    3180
acatggcaac tgcagttcac ttacaccgct tctcaacccg gtacgcacca gaaaatcatt    3240
gatatggcca tgaatggcgt tggatgccgg gcaacagccc gcattatggg cgttggcctc    3300
aacacgattt tacgtcactt aaaaaactca ggccgcagtc ggtaacctcg cgcatacagc    3360
cgggcagtga cgtcatcgtc tgcgcggaaa tggacgaaca gtgggctat gtcggggcta    3420 aatcgcgcca gcgctggctg ttttacgcgt atgacagtct ccggaagacg gttgttgcgc    3480
acgtattcgg tgaacgcact atggcgacgc tgggggcgtct tatgagcctg ctgtcaccct    3540
ttgacgtggt gatatggatg acggatggct ggccgctgta tgaatcccgc ctgaagggaa    3600
agctgcacgt aatcagcaag cgatatacgc agcgaattga gcggcataac ctgaatctga    3660
ggcagcacct ggcacggctg ggacggaagt cgctgtcgtt ctcaaaatcg gtggagctgc    3720
atgacaaagt catcgggcat tatctgaaca taaaacacta tcaataagtt ggagtcatta    3780
cccaaccagg aagggcagcc cacctatcaa ggtgtactgc cttccagacg aacgaagagc    3840
gattgaggaa aaggcggcgg cggccggcat gagcctgtcg gcctacctgc tggccgtcgg    3900
ccagggctac aaaatcacgg gcgtcgtgga ctatgagcac gtccgcgagc tggcccgcat    3960
caatggcgac ctgggccgcc tgggcggcct gctgaaactc tggctcaccg acgacccgcg    4020
cacggcgcgg ttcggtgatg ccacgatcct cgccctgctg gcgaagatcg aagagaagca    4080
ggacgagctt ggcaaggtca tgatgggcgt ggtccgcccg agggcagagc catgactttt    4140
ttagccgcta aaacggccgg ggggtgcgcg tgattgccaa gcacgtcccc atgcgctcca    4200
tcaagaagag cgacttcgcg gagctggtat tcgtgcaggg caagattcgg aataccaagt    4260
acgagaagga cggccagacg gtctacggga ccgacttcat tgccgataag gtggattatc    4320
tggacaccaa ggcaccaggc gggtcaaatc aggaataagg gcacattgcc ccggcgtgag    4380
tcggggcaat cccgcaagga gggtgaatga atcggacgtt tgaccggaag gcatacaggc    4440
aagaactgat cgacgcgggg ttttccgccg aggatgccga aaccatcgca agccgcaccg    4500
tcatgcgtgc gccccgcgaa accttccagt ccgtcggctc gatggtccag caagctacgg    4560
```

```
ccaagatcga gcgcgacagc gtgcaactgg ctccccctgc cctgcccgcg ccatcggccg    4620
ccgtggagcg ttcgcgtcgt ctcgaacagg aggcggcagg tttggcgaag tcgatgacca    4680
tcgacacgcg aggaactatg acgaccaaga agcgaaaaac cgccggcgag gacctggcaa    4740
aacaggtcag cgaggccaag caggccgcgt tgctgaaaca cacgaagcag cagatcaagg    4800
aaatgcagct ttccttgttc gatattgcgc cgtggccgga cacgatgcga gcgatgccaa    4860
acgacacggc ccgctctgcc ctgttcacca cgcgcaacaa gaaaatcccg cgcgaggcgc    4920
tgcaaaacaa ggtcattttc cacgtcaaca aggacgtgaa gatcacctac accggcgtcg    4980
agctgcgggc cgacgatgac gaactggtgt ggcagcaggt gttggagtac gcgaagcgca    5040 ccccctatcgg cgagccgatc accttcacgt tctacgagct ttgccaggac ctgggctggt    5100
cgatcaatgg ccgtattac acgaaggccg aggaatgcct gtcgcgccta caggcgacgg    5160
cgatgggctt cacgtccgac cgcgttgggc acctggaatc ggtgtcgctg ctgcaccgct    5220
tccgcgtcct ggaccgtggc aagaaaacgt cccgttgcca ggtcctgatc gacgaggaaa    5280
tcgtcgtgct gttgctggc gaccactaca cgaaattcat atgggagaag taccgcaagc    5340
tgtcgccgac ggcccgacgg atgttcgact atttcagctc gcaccgggag ccgtacccgc    5400
tcaagctgga aaccttccgc ctcatgtgcg gatcggattc cacccgcgtg aagaagtggc    5460
gcgagcaggt cggcgaagcc tgcgaagagt tgcgaggcag cggcctggtg gaacacgcct    5520
gggtcaatga tgacctggtg cattgcaaac gctagggcct tgtggggtca gttccggctg    5580
ggggttcagc agccagcgct ttactggcat ttcaggaaca agcgggcact gctcgacgca    5640
cttgcttcgc tcagtatcgc tcgggacgca cggcgcgctc tacgaactgc cgataaacag    5700
aggattaaaa ttgacaattg tgattaaggc tcagattcga cggcttggag cggccgacgt    5760
gcaggatttc cgcgagatcc gattgtcggc cctgaagaaa gctccagaga tgttcgggtc    5820
cgtttacgag cacgaggaga aaaagcccat ggaggcgttc gctgaacggt tgcgagatgc    5880
cgtggcattc ggcgcctaca tcgacggcga gatcattggg ctgtcggtct tcaaacagga    5940
ggacggcccc aaggacgctc acaaggcgca tctgtccggc gttttcgtgg agcccgaaca    6000
gcgaggccga ggggtcgccg gtatgctgct gcgggcgttg ccggcgggtt tattgctcgt    6060
gatgatcgtc cgacagattc caacgggaat ctggtggatg cgcatcttca tcctcggcgc    6120
acttaatatt tcgctattct ggagcttgtt gtttatttcg gtctaccgcc tgccgggcgg    6180
ggtcgcggcg acgtaggcg ctgtgcagcc gctgatggtc gtgttcatct ctgccgctct    6240
gctaggtagc ccgatacgat tgatggcggt cctgggggct atttgcggaa ctgcgggcgt    6300
ggcgctgttg gtgttgacac caaacgcagc gctagatcct gtcggcgtcg cagcgggcct    6360
ggcgggggcg gtttccatgg cgttcggaac cgtgctgacc cgcaagtggc aacctcccgt    6420
gcctctgctc acctttaccg cctggcaact ggcggccgga ggacttctgc tcgttccagt    6480
agctttagtg tttgatccgc caatcccgat gcctacagga accaatgttc tcggcctggc    6540
gtggctcggc ctgatcggag cgggtttaac ctacttcctt tggttccggg ggatctcgcg    6600
actcgaacct acagttgttt ccttactggg ctttctcagc cgggatggcg ctaagaagct    6660
attgccgccg atcttcatat gcggtgtgaa ataccgcaca gatgcgtaag gagaaaatac    6720
cgcatcaggc gctcttccgc ttcctcgctc actgactcgc tgcgctcggt cgttcggctg    6780
cggcgagcgg tatcagctca ctcaaaggcg gtaatacggt tatccacaga atcaggggat    6840
aacgcaggaa agaacatgtg agcaaaaggc cagcaaaagg ccaggaaccg taaaaaggcc    6900
gcgttgctgg cgtttttcca taggctccgc cccccctgacg agcatcacaa aaatcgacgc    6960
```

-continued

```
tcaagtcaga ggtggcgaaa cccgacagga ctataaagat accaggcgtt tccccctgga   7020
agctccctcg tgcgctctcc tgttccgacc ctgccgctta ccggatacct gtccgccttt   7080
ctcccttcgg gaagcgtggc gctttctcaa tgctcacgct gtaggtatct cagttcggtg   7140
taggtcgttc gctccaagct gggctgtgtg cacgaaccec ccgttcagcc cgaccgctgc   7200
gccttatccg gtaactatcg tcttgagtcc aacccggtaa gacacgactt atcgccactg   7260
gcagcagcca ctggtaacag gattagcaga gcgaggtatg taggcggtgc tacagagttc   7320
ttgaagtggt ggcctaacta cggctacact agaaggacag tatttggtat ctgcgctctg   7380
ctgaagccag ttaccttcgg aaaaagagtt ggtagctctt gatccggcaa acaaaccacc   7440
gctggtagcg gtggtttttt tgtttgcaag cagcagatta cgcgcagaaa aaaggatat   7500 caagaagatc ctttgatctt ttctacgggg tctgacgctc agtggaacga aaactcacgt   7560
taagggattt tggtcatgag attatcaaaa aggatcttca cctagatcct tttaaattaa   7620
aaatgaagtt ttaaatcaat ctaaagtata tatgagtaaa cttggtctga cagttaccaa   7680
tgcttaatca gtgaggcacc tatctcagcg atctgtctat ttcgttcatc catagttgcc   7740
tgactccccg tcgtgtagat aactacgata cgggagggct taccatctgg ccccagtgct   7800
gcaatgatac cgcgagaccc acgctcaccg gctccagatt tatcagcaat aaaccagcca   7860
gccggaaggg ccgagcgcag aagtggtcct gcaactttat ccgcctccat ccagtctatt   7920
aaacaagtgg cagcaacgga ttcgcaaacc tgtcacgcct tttgtgccaa agccgcgcc    7980 aggtttgcga tccgctgtgc caggcgttag gcgtcatatg aagatttcgg tgatccctga   8040
gcaggtggcg gaaacattgg atgctgagaa ccatttcatt gttcgtgaag tgttcgatgt   8100
gcacctatcc gaccaaggct ttgaactatc taccagaagt gtgagcccct accggaagga   8160
ttacatctcg gatgatgact ctgatgaaga ctctgcttgc tatggcgcat tcatcgacca   8220
agagcttgtc gggaagattg aactcaactc aacatggaac gatctagcct ctatcgaaca   8280
cattgttgtg tcgcacacgc accgaggcaa aggagtcgcg cacagtctca tcgaatttgc   8340
gaaaaagtgg gcactaagca gacagctcct tggcatacga ttagagacac aaacgaacaa   8400
tgtacctgcc tgcaatttgt acgcaaaatg tggctttact ctcggcggca ttgacctgtt   8460
cacgtataaa actagacctc aagtctcgaa cgaaacagcg atgtactggt actggttctc   8520
gggagcacag gatgacgcct aacaattcat tcaagccgac accgcttcgc ggcgcggctt   8580
aattcaggag ttaaacatca tgagggaagc ggtgatcgcc gaagtatcga ctcaactatc   8640
agaggtagtt ggcgtcatcg agcgccatct cgaaccgacg ttgctggccg tacatttgta   8700
cggctccgca gtggatggcg gcctgaagcc acacagtgat attgatttgc tggttacggt   8760
gaccgtaagg cttgatgaaa caacgcggcg agctttgatc aacgaccttt tggaaacttc   8820
ggcttcccct ggagagagcg agattctccg cgctgtagaa gtcaccattg ttgtgcacga   8880
cgacatcatt ccgtggcgtt atccagctaa gcgcgaactg caatttggag aatggcagcg   8940
caatgacatt cttgcaggta tcttcgagcc agccacgatc gacattgatc tggctatctt   9000
gctgacaaaa gcaagagaac atagcgttgc cttggtaggt ccagcggcgg aggaactctt   9060
tgatccggtt cctgaacagg atctatttga ggcgctaaat gaaaccttaa cgctatggaa   9120
ctcgccgccc gactgggctg cgatgagcg aaatgtagtg cttacgttgt cccgcatttg   9180
gtacagcgca gtaaccggca aaatcgcgcc gaaggatgtc gctgccgact gggcaatgga   9240
gcgcctgccg gcccagtatc agcccgtcat acttgaagct aggcaggctt atcttggaca   9300
agaagatcgc ttggcctcgc gcgcagatca gttggaagaa tttgttcact acgtgaaagg   9360
```

-continued

```
cgagatcacc aaggtagtcg gcaaataatg tctaacaatt cgttcaagcc gacgccgctt   9420
cgcggcgcgg cttaactcaa gcgttagaga gctggggaag actatgcgcg atctgttgaa   9480
ggtggttcta agcctcgtac ttgcgatggc atcggggcag gcacttgctg acctgccaat   9540
tgttttagtg gatgaagctc gtcttcccta tgactactcc ccatccaact acgacatttc   9600
tccaagcaac tacgcaaact ccataagcaa ttacgacaat agtccatcaa attacgacaa   9660
ctctgagagc aactacgata atagttcatc caattacgac aatagtcgca acggaaatcg   9720
taggcttata tatagcgcaa atgggtctcg cactttcgcc ggctactacg tcattgccaa   9780
caatgggaca acgaacttct tttccacatc tggcaaaagg atgttctaca ccccaaaagg   9840
ggggcgcggc gtctatggcg gcaaagatgg gagcttctgc ggggcattgg tcgtcataaa   9900
tggccaattt tcgcttgccc tgacagataa cggcctgaag atcatgtatc taagcaacta   9960
gcctgctctc taataaaatg ttaggagctt ggctgccatt tttggggtga ggccgttcgc  10020
ggccgagggg cgcagcccct gggggatggg gaggcccgcg ttagcgggcc gggagggttc  10080
gagaaggggg ggcaccccccc ttcggcgtgc gcggtcacgc gccagggcgc agccctggtt  10140
aaaaacaagg tttataaata ttggtttaaa agcaggttaa aagacaggtt agcggtggcc  10200
gaaaaacggg cggaaaccct tgcaaatgct ggattttctg cctgtggaca gcccctcaaa  10260
tgtcaatagg tgcgcccctc atctgtcagc actctgcccc tcaagtgtca aggatcgcgc  10320
ccctcatctg tcagtagtcg cgcccctcaa gtgtcaatac cgcagggcac ttatccccag  10380
gcttgtccac atcatctgtg ggaaactcgc gtaaaatcag gcgttttcgc cgatttgcga  10440
ggctggccag ctccacgtcg ccggccgaaa tcgagcctgc ccctcatctg tcaacgccgc  10500
gccgggtgag tcgcccctc aagtgtcaac gtccgcccct catctgtcag tgagggccaa  10560
gttttccgcg aggtatccac aacgccggcg gccggccgcg gtgtctcgca cacggcttcg  10620
acggcgtttc tggcgcgttt gcagggccat agacggccgc cagcccagcg gcgagggcaa  10680
ccagcccggt gagcgtcgga aagggtcgac atcttgctgc gttcggatat tttcgtggag  10740
ttcccgccac agaccggat tgaaggcgag atccagcaac tcgcgccaga tcatcctgtg  10800
acggaacttt ggcgcgtgat gactggccag gacgtcggcc gaaagagcga caagcagatc  10860
acgattttcg acagcgtcgg atttgcgatc gaggattttt cggcgctgcg ctacgtccgc  10920
gaccgcgttg agggatcaag ccacagcagc ccactcgacc ttctagccga cccagacgag  10980
ccaagggatc tttttggaat gctgctccgt cgtcaggctt tccgacgttt gggtggttga  11040
acagaagtca ttatcgtacg gaatgccagc actcccgagg ggaaccctgt ggttggcatg  11100
cacatacaaa tggacgaacg gataaacctt tcacgccct tttaaatatc cgttattcta  11160
ataaacgctc ttttctctta ggtttacccg ccaatatatc ctgtcaaaca ctgatagttt  11220
aaactgaagg cgggaaacga caatctgatc atgagcggag aattaaggga gtcacgttat  11280
gacccccgcc gatgacgcgg gacaagccgt tttacgtttg gaactgacag aaccgcaacg  11340
attgaaggag ccactcagcc ccaatacgca aaccgcctct ccccgcgcgt tggccgattc  11400
attaatgcag ctggcacgac aggtttcccg actggaaagc gggcagtgag cgcaacgcaa  11460
ttaatgtgag ttagctcact cattaggcac cccaggcttt acactttatg cttccggctc  11520
gtatgttgtg tggaattgtg agcggataac aatttcacac aggaaacagc tatgaccatg  11580
attacgccaa gctatttagg tgacactata gaatactcaa gctatgcatc caacgcgttg  11640
ggagctctcc catatcgacc tgcaggcggc cgctcgacga attaattcca atcccacaaa  11700
aatctgagct taacagcaca gttgctcctc tcagagcaga atcgggtatt caacaccctc  11760
```

```
atatcaacta ctacgttgtg tataacggtc cacatgccgg tatatacgat gactggggtt    11820
gtacaaaggc ggcaacaaac ggcgttcccg gagttgcaca caagaaattt gccactatta    11880
cagaggcaag agcagcagct gacgcgtaca caacaagtca gcaaacagac aggttgaact    11940
tcatccccaa aggagaagct caactcaagc ccaagagctt tgctaaggcc ctaacaagcc    12000
caccaaagca aaaagcccac tggctcacgc taggaaccaa aaggcccagc agtgatccag    12060
ccccaaaaga gatctccttt gccccggaga ttacaatgga cgatttcctc tatctttacg    12120
atctaggaag gaagttcgaa ggtgaaggtg acgacactat gttcaccact gataatgaga    12180
aggttagcct cttcaatttc agaaagaatg ctgacccaca gatggttaga gaggcctacg    12240
cagcaggtct catcaagacg atctacccga gtaacaatct ccaggagatc aaataccttc    12300
ccaagaaggt taaagatgca gtcaaaagat tcaggactaa ttgcatcaag aacacagaga    12360
aagacatatt tctcaagatc agaagtacta ttccagtatg gacgattcaa ggcttgcttc    12420
ataaaccaag gcaagtaata gagattggag tctctaaaaa ggtagttcct actgaatcta    12480
aggccatgca tggagtctaa gattcaaatc gaggatctaa cagaactcgc cgtgaagact    12540
ggcgaacagt tcatacagag tcttttacga ctcaatgaca agaagaaaat cttcgtcaac    12600
atggtggagc acgacactct ggtctactcc aaaaatgtca agatacagt ctcagaagac    12660
caaagggcta ttgagacttt tcaacaaagg ataatttcgg gaaacctcct cggattccat    12720
tgcccagcta tctgtcactt catcgaaagg acagtagaaa aggaaggtgg ctcctacaaa    12780
tgccatcatt gcgataaagg aaaggctatc attcaagatc tctctgccga cagtggtccc    12840
aaagatggac ccccacccac gaggagcatc gtggaaaaag aagacgttcc aaccacgtct    12900
tcaaagcaag tggattgatg tgacatctcc actgacgtaa gggatgacgc acaatcccac    12960
tatccttcgc aagaccctttc ctctatataa ggaagttcat ttcatttgga gaggacacgc    13020
tcgaggctag catggatctc gggccccaaa taatgatttt attttgactg atagtgacct    13080
gttcgttgca acaaattgat gagcaatgct tttttataat gccaactttg tacaaaaaag    13140
ctgaacgaga aacgtaaaat gatataaata tcaatatatt aaattagatt ttgcataaaa    13200
aacagactac ataatactgt aaaacacaac atatccagtc actatgaatc aactacttag    13260
atggtattag tgacctgtag tcgaccgaca gccttccaaa tgttcttcgg gtgatgctgc    13320
caacttagtc gaccgacagc cttccaaatg ttcttctcaa acggaatcgt cgtatccagc    13380
ctactcgcta ttgtcctcaa tgccgtatta aatcataaaa agaaataaga aaaagaggtg    13440
cgagcctctt ttttgtgtga caaaataaaa acatctacct attcatatac gctagtgtca    13500
tagtcctgaa aatcatctgc atcaagaaca atttcacaac tcttatactt ttctcttaca    13560
agtcgttcgg cttcatctgg attttcagcc tctatactta ctaaacgtga taaagtttct    13620
gtaatttcta ctgtatcgac ctgcagactg gctgtgtata agggagcctg acatttatat    13680
tccccagaac atcaggttaa tggcgttttt gatgtcattt tcgcggtggc tgagatcagc    13740
cacttcttcc ccgataacgg agaccggcac actggccata tcggtggtca tcatgcgcca    13800
gctttcatcc ccgatatgca ccaccgggta aagttcacgg gagactttat ctgacagcag    13860
acgtgcactg gccaggggga tcaccatccg tcgcccgggc gtgtcaataa tatcactctg    13920
tacatccaca aacagacgat aacgctctct cttttatag gtgtaaacct taaactgcat    13980
ttcaccagtc cctgttctcg tcagcaaaag agccgttcat ttcaataaac cgggcgacct    14040
cagccatccc ttcctgattt tccgctttcc agcgttcggc acgcagacga cgggcttcat    14100
tctgcatggt tgtgcttacc agaccggaga tattgacatc atatatgcct tgagcaactg    14160
```

```
atagctgtcg ctgtcaactg tcactgtaat acgctgcttc atagcacacc tcttttttgac    14220 atacttcggg tagtgccgat caacgtctca ttttcgccaa aagttggccc agggcttccc     14280
ggtatcaaca gggacaccag gatttattta ttctgcgaag tgatcttccg tcacaggtat    14340
ttattcggcg caaagtgcgt cgggtgatgc tgccaactta gtcgactaca ggtcactaat    14400
accatctaag tagttgattc atagtgactg gatatgttgt gttttacagt attatgtagt    14460 ctgttttta tgcaaaatct aatttaatat attgatattt atatcatttt acgtttctcg     14520
ttcagctttc ttgtacaaag ttggcattat aagaaagcat tgcttatcaa tttgttgcaa    14580
cgaacaggtc actatcagtc aaaataaaat cattatttgc catccagctg cagctcctcg    14640
aggaattcgg taccccaatt ggtaaggaaa taattatttt cttttttcct tttagtataa    14700
aatagttaag tgatgttaat tagtatgatt ataataatat agttgttata attgtgaaaa    14760
aataatttat aaatatattg tttacataaa caacatagta atgtaaaaaa atatgacaag    14820
tgatgtgtaa gacgaagaag ataaaagttg agagtaagta tattatttt aatgaatttg      14880 atcgaacatg taagatgata tacggccggt aagaggttcc aactttcacc ataatgaaat    14940
aagatcacta ccgggcgtat ttttgagtt atcgagattt tcaggagcta aggaagctaa      15000
aatggagaaa aaaatcactg gatataccac cgttgatata tcccaatggc atcgtaaaga    15060
acattttgag gcatttcagt cagttgctca atgtacctat aaccagaccg ttcagctgga    15120
tattacggcc ttttttaaga ccgtaaagaa aaataagcac aagttttatc cggcctttat    15180
tcacattctt gcccgcctga tgaatgctca tccggaattc cgtatggcaa tgaaagacgg    15240
tgagctggtg atatgggata gtgttcaccc ttgttacacc gttttccatg agcaaactga    15300
aacgttttca tcgctctgga gtgaatacca cgacgatttc cggcagtttc tacacatata    15360
ttcgcaagat gtggcgtgtt acggtgaaaa cctggcctat ttccctaaag ggtttattga    15420
gaatatgttt ttcgtctcag ccaatccctg ggtgagtttc accagttttg atttaaacgt    15480
ggccaatatg gacaacttct tcgccccccgt tttcaccatg ggcaaatatt atacgcaagg    15540
cgacaaggtg ctgatgccgc tggcgattca ggttcatcat gccgtctgtg atggcttcca    15600
tgtcggcaga atgcttaatg aattacaaca gtactgcgat gagtggcagg gcggggcgta    15660
atcgcgtgga tccggcttac taaaagccag ataacagtat gcgtatttgc gcgctgattt    15720
ttgcggtata agaatatata ctgatatgtc gggcccataa tagtaattct agctggtttg    15780
atgaattaaa tatcaatgat aaaatactat agtaaaaata agaataaata aattaaaata    15840 atatttttt atgattaata gtttattata taattaaata tctataccat tactaaatat     15900
tttagtttaa aagttaataa atattttgtt agaaattcca atctgcttgt aatttatcaa    15960
taaacaaaat attaaataac aagctaaagt aacaaataat atcaaactaa tagaaacagt    16020
aatctaatgt aacaaaacat aatctaatgc taatataaca aagcgcaaga tctatcattt    16080
tatatagtat tattttcaat caacattctt attaatttct aaataatact tgtagtttta    16140
ttaacttcta aatggattga ctattaatta aatgaattag tcgaacatga ataaacaagg    16200
taacatgata gatcatgtca ttgtgttatc attgatctta catttggatt gattacagtt    16260
gggaaattgg gttcgaaatc gataagcttg gatcctctag agagctgcag ctggatggca    16320
aataatgatt ttattttgac tgatagtgac ctgttcgttg caacaaattg ataagcaatg    16380 cttcttata atgccaactt tgtacaagaa agctgaacga gaaacgtaaa atgatataaa    16440
tatcaatata ttaaattaga ttttgcataa aaaacagact acataatact gtaaaacaca    16500
acatatccag tcactatgaa tcaactactt agatggtatt agtgacctgt agtcgactaa    16560
```

-continued

```
gttggcagca tcacccgacg cactttgcgc cgaataaata cctgtgacgg aagatcactt    16620
cgcagaataa ataaatcctg gtgtccctgt tgataccggg aagccctggg ccaacttttg    16680
gcgaaaatga gacgttgatc ggcactaccc atttcacaac tcttatactt ttctcttaca    16740
agtcgttcgg cttcatctgg attttcagcc tctatactta ctaaacgtga taaagtttct    16800
gtaatttcta ctgtatcgac ctgcagactg gctgtgtata agggagcctg acatttatat    16860
tccccagaac atcaggttaa tggcgttttt gatgtcattt tcgcggtggc tgagatcagc    16920
cacttcttcc ccgataacgg agaccggcac actggccata tcggtggtca tcatgcgcca    16980
gctttcatcc ccgatatgca ccaccgggta aagttcacgg gagactttat ctgacagcag    17040
acgtgcactg gccaggggga tcaccatccg tcgcccgggc gtgtcaataa tatcactctg    17100
tacatccaca aacagacgat aacgctctc tcttttatag gtgtaaacct taaactgcat    17160
ttcaccagtc cctgttctcg tcagcaaaag agccgttcat ttcaataaac cgggcgacct    17220
cagccatccc ttcctgattt tccgctttcc agcgttcggc acgcagacga cgggcttcat    17280
tctgcatggt tgtgcttacc agaccggaga tattgacatc atatatgcct tgagcaactg    17340
atagctgtcg ctgtcaactg tcactgtaat acgctgcttc atagcacacc tcttttttgac   17400 atacttctgt tcttgatgca gatgattttc aggactatga cactagcgta tatgaatagg    17460
tagatgtttt tattttgtca cacaaaaaag aggctcgcac ctcttttttct tatttctttt    17520 tatgatttaa tacggcattg aggacaatag cgagtaggct ggatacgacg attccgtttg    17580
agaagaacat ttggaaggct gtcggtcgac taagttggca gcatcacccg aagaacattt    17640
ggaaggctgt cggtcgacta caggtcacta ataccatcta agtagttgat tcatagtgac    17700
tggatatgtt gtgttttaca gtattatgta gtctgttttt tatgcaaaat ctaatttaat    17760
atattgatat ttatatcatt ttacgtttct cgttcagctt ttttgtacaa agttggcatt    17820
ataaaaaagc attgctcatc aatttgttgc aacgaacagg tcactatcag tcaaaataaa    17880
atcattattt ggggcccgag atccatgcta gctctagagt cctgctttaa tgagatatgc    17940
gagacgccta tgatcgcatg atatttgctt tcaattctgt tgtgcacgtt gtaaaaaacc    18000
tgagcatgtg tagctcagat ccttaccgcc ggtttcggtt cattctaatg aatatatcac    18060
ccgttactat cgtatttttta tgaataatat tctccgttca atttactgat tgtaccctac    18120
tacttatatg tacaatatta aaatgaaaac aatatattgt gctgaatagg tttatagcga    18180
catctatgat agagcgccac aataacaaac aattgcgttt tattattaca aatccaattt    18240
taaaaaaagc ggcagaaccg gtcaaaccta aaagactgat tacataaatc ttattcaaat    18300
ttcaaaaggc cccaggggct agtatctacg acacaccgag cggcgaacta ataacgttca    18360
ctgaagggaa ctccggttcc ccgccggcgc gcatgggtga gattccttga agttgagtat    18420
tggccgtccg ctctaccgaa agttacgggc accattcaac ccggtccagc acggcggccg    18480
ggtaaccgac ttgctgcccc gagaattatg cagcattttt ttggtgtatg tgggccccaa    18540
atgaagtgca ggtcaaacct tgacagtgac gacaaatcgt tgggcgggtc cagggcgaat    18600
tttgcgacaa catgtcgagg ctcagcagga cctgcaggca tgcaagctag cttactagtg    18660
atgcatattc tatagtgtca cctaaatctg c                                   18691
```

<210> SEQ ID NO 14
<211> LENGTH: 59
<212> TYPE: DNA
<213> ORGANISM: Artificial sequence

```
<220> FEATURE:
<223> OTHER INFORMATION: forward primer used for the amplification of
      200 and 400 bp CHS fragments

<400> SEQUENCE: 14
ggggacaagt ttgtacaaaa aagcaggctg cactgctaac cctgagaacc atgtgcttc         59

<210> SEQ ID NO 15
<211> LENGTH: 59
<212> TYPE: DNA
<213> ORGANISM: Artificial sequence
<220> FEATURE:
<223> OTHER INFORMATION: reverse primer for amplification of 400 bp CHS
      fragment

<400> SEQUENCE: 15
ggggaccact ttgtacaaga aagctgggtc gcttgacgga aggacggaga ccaagaagc         59

<210> SEQ ID NO 16
<211> LENGTH: 59
<212> TYPE: DNA
<213> ORGANISM: Artificial sequence
<220> FEATURE:
<223> OTHER INFORMATION: reverse primer for amplification of 200bp CHS
      fragment

<400> SEQUENCE: 16
ggggaccact ttgtacaaga aagctgggta ggagccatgt aagcacacat gtgtgggtt         59

<210> SEQ ID NO 17
<211> LENGTH: 100
<212> TYPE: DNA
<213> ORGANISM: Artificial sequence
<220> FEATURE:
<223> OTHER INFORMATION: forward primer for amplification of 100bp CHS
      fragment

<400> SEQUENCE: 17
ggggacaagt ttgtacaaaa aagcaggctg cactgctaac cctgagaacc atgtgcttca        60
ggcggagtat cctgactact acttccgcat caccaacagt                             100

<210> SEQ ID NO 18
<211> LENGTH: 100
<212> TYPE: DNA
<213> ORGANISM: Artificial sequence
<220> FEATURE:
<223> OTHER INFORMATION: reverse primer for amplification of 100 bp CHS
      fragment

<400> SEQUENCE: 18
ggggaccact ttgtacaaga aagctgggta acttctcctt gaggtcggtc atgtgttcac        60
tgttggtgat gcggaagtag tagtcaggat actccgcctg                             100

<210> SEQ ID NO 19
<211> LENGTH: 79
<212> TYPE: DNA
<213> ORGANISM: Artificial sequence
<220> FEATURE:
<223> OTHER INFORMATION: forward primer for amplification of 50 bp CHS
      fragment

<400> SEQUENCE: 19
ggggacaagt ttgtacaaaa aagcaggctg cactgctaac cctgagaacc atgtgcttca        60
ggcggagtat cctgactac                                                     79
```

```
<210> SEQ ID NO 20
<211> LENGTH: 79
<212> TYPE: DNA
<213> ORGANISM: Artificial sequence
<220> FEATURE:
<223> OTHER INFORMATION: reverse primer for 50 bp CHS fragment

<400> SEQUENCE: 20
ggggaccact tgtacaaga aagctgggtg tagtcaggat actccgcctg aagcacatgg      60
ttctcagggt tagcagtgc                                                 79

<210> SEQ ID NO 21
<211> LENGTH: 54
<212> TYPE: DNA
<213> ORGANISM: Artificial sequence
<220> FEATURE:
<223> OTHER INFORMATION: forward primer for amplification of the 25 bp
      CHS fragment

<400> SEQUENCE: 21
ggggacaagt ttgtacaaaa aagcaggctg cactgctaac cctgagaacc atgt          54

<210> SEQ ID NO 22
<211> LENGTH: 54
<212> TYPE: DNA
<213> ORGANISM: Artificial sequence
<220> FEATURE:
<223> OTHER INFORMATION: reverse primer for amplification of the 25 bp
      CHS fragment

<400> SEQUENCE: 22
ggggaccact ttgtacaaga aagctgggta catggttctc agggttagca gtgc           54

<210> SEQ ID NO 23
<211> LENGTH: 17862
<212> TYPE: DNA
<213> ORGANISM: Artificial sequence
<220> FEATURE:
<223> OTHER INFORMATION: acceptor vector pHELLSGATE4

<400> SEQUENCE: 23
ggccgcacta gtgatatccc gcggccatgg cggccgggag catgcgacgt cgggcccaat     60
tcgccctata gtgagtcgta ttacaattca ctggccgtcg ttttacaacg tcgtgactgg   120
gaaaaccctg gcgttaccca acttaatcgc cttgcagcac atccccctt  cgccagctgg   180 cgtaatagcg aagaggcccg caccgatcgc ccttcccaac agttgcgcag cctgaatggc   240
gaatggaaat tgtaaacgtt aatggggtttc tggagtttaa tgagctaagc acatacgtca   300
gaaaccatta ttgcgcgttc aaaagtcgcc taaggtcact atcagctagc aaatatttct   360
tgtcaaaaat gctccactga cgttccataa attcccctcg gtatccaatt agagtctcat   420
attcactctc aatccaaata atctgcaatg gcaattacct tatccgcaac ttctttacct   480
atttccgccc ggatccgggc aggttctccg gccgcttggg tggagaggct attcggctat   540
gactgggcac aacagacaat cggctgctct gatgccgccg tgttccggct gtcagcgcag   600
gggcgcccgg ttcttttttgt caagaccgac ctgtccggtg ccctgaatga actgcaggac   660
gaggcagcgc ggctatcgtg ctggccacg acgggcgttc cttgcgcagc tgtgctcgac   720
gttgtcactg aagcgggaag ggactggctg ctattgggcg aagtgccggg gcaggatctc   780
ctgtcatctc accttgctcc tgccgagaaa gtatccatca tggctgatgc aatgcggcgg   840
ctgcatacgc ttgatccggc tacctgccca ttcgaccacc aagcgaaaca tcgcatcgag   900
```

-continued

```
cgagcacgta ctcggatgga agccggtctt gtcgatcagg atgatctgga cgaagagcat      960
caggggctcg cgccagccga actgttcgcc aggctcaagg cgcgcatgcc cgacggcgag     1020
gatctcgtcg tgacccatgg cgatgcctgc ttgccgaata tcatggtgga aaatggccgc     1080
ttttctggat tcatcgactg tggccggctg ggtgtggcgg accgctatca ggacatagcg     1140
ttggctaccc gtgatattgc tgaagagctt ggcggcgaat gggctgaccg cttcctcgtg     1200
ctttacggta tcgccgctcc cgattcgcag cgcatcgcct tctatcgcct tcttgacgag     1260
ttcttctgag cgggactctg gggttcgaaa tgaccgacca agcgacgccc aacctgccat     1320
cacgagattt cgattccacc gccgccttct atgaaaggtt gggcttcgga atcgttttcc     1380
gggacgccgg ctggatgatc tccagcgcg gggatctcat gctggagttc ttcgcccacc      1440
ccgatccaac acttacgttt gcaacgtcca agagcaaata gaccacgaac gccggaaggt     1500
tgccgcagcg tgtggattgc gtctcaattc tctcttgcag gaatgcaatg atgaatatga     1560
tactgactat gaaactttga gggaatactg cctagcaccg tcacctcata acgtgcatca     1620
tgcatgccct gacaacatgg aacatcgcta ttttctgaa gaattatgct cgttggagga      1680
tgtcgcggca attgcagcta ttgccaacat cgaactaccc ctcacgcatg cattcatcaa     1740
tattattcat gcggggaaag gcaagattaa tccaactggc aaatcatcca gcgtgattgg     1800
taacttcagt tccagcgact tgattcgttt tggtgctacc cacgttttca ataaggacga     1860
gatggtggag taaagaagga gtgcgtcgaa gcagatcgtt caaacatttg caataaagt      1920
ttcttaagat tgaatcctgt tgccggtctt gcgatgatta tcatataatt tctgttgaat     1980
tacgttaagc atgtaataat taacatgtaa tgcatgacgt tatttatgag atgggttttt     2040
atgattagag tcccgcaatt atacatttaa tacgcgatag aaaacaaaat atagcgcgca     2100
aactaggata aattatcgcg cgcggtgtca tctatgttac tagatcgaat taattccagg     2160
cggtgaaggg caatcagctg ttgcccgtct cactggtgaa aagaaaaacc accccagtac     2220
attaaaaacg tccgcaatgt gttattaagt tgtctaagcg tcaatttgtt tacaccacaa     2280
tatatcctgc caccagccag ccaacagctc cccgaccggc agctcggcac aaaatcacca     2340
ctcgatacag gcagcccatc agtccgggac ggcgtcagcg ggagagccgt tgtaaggcgg     2400
cagactttgc tcatgttacc gatgctattc ggaagaacgg caactaagct gccgggtttg     2460
aaacacggat gatctcgcgg agggtagcat gttgattgta acgatgacag agcgttgctg     2520
cctgtgatca aatatcatct ccctcgcaga gatccgaatt atcagccttc ttattcattt     2580
ctcgcttaac cgtgacaggc tgtcgatctt gagaactatg ccgacataat aggaaatcgc     2640
tggataaagc cgctgaggaa gctgagtggc gctatttctt tagaagtgaa cgttgacgat     2700
gtcgacggat ctttccgct gcataaccct gcttcggggt cattatagcg attttttcgg      2760
tatatccatc cttttttcgca cgatatacag gattttgcca aagggttcgt gtagactttc    2820
cttggtgtat ccaacggcgt cagccgggca ggataggtga agtaggccca cccgcgagcg     2880
ggtgttcctt cttcactgtc ccttattcgc acctggcggt gctcaacggg aatcctgctc     2940
tgcgaggctg gccggctacc gccggcgtaa cagatgaggg caagcggatg ctgatgaaa      3000
ccaagccaac caggggtgat gctgccaact tactgattta tgtatgatg gtgttttga       3060
ggtgctccag tggcttctgt ttctatcagc tgtccctcct gttcagctac tgacggggtg     3120
gtgcgtaacg gcaaaagcac cgccggacat cagcgctatc tctgctctca ctgccgtaaa     3180
acatggcaac tgcagttcac ttacaccgct tctcaacccg gtacgcacca gaaaatcatt     3240
gatatggcca tgaatggcgt tggatgccgg gcaacagccc gcattatggg cgttggcctc     3300
```

```
aacacgattt tacgtcactt aaaaaactca ggccgcagtc ggtaacctcg cgcatacagc    3360
cgggcagtga cgtcatcgtc tgcgcggaaa tggacgaaca gtggggctat gtcggggcta    3420
aatcgcgcca gcgctggctg ttttacgcgt atgacagtct ccggaagacg gttgttgcgc    3480
acgtattcgg tgaacgcact atggcgacgc tgggcgtct tatgagcctg ctgtcaccct     3540
ttgacgtggt gatatggatg acggatggct ggccgctgta tgaatcccgc ctgaagggaa    3600
agctgcacgt aatcagcaag cgatatacgc agcgaattga gcggcataac ctgaatctga    3660
ggcagcacct ggcacggctg ggacggaagt cgctgtcgtt ctcaaaatcg gtggagctgc    3720
atgacaaagt catcgggcat tatctgaaca taaaacacta tcaataagtt ggagtcatta    3780
cccaaccagg aagggcagcc cacctatcaa ggtgtactgc cttccagacg aacgaagagc    3840
gattgaggaa aaggcggcgg cggccggcat gagcctgtcg gcctacctgc tggccgtcgg    3900
ccagggctac aaaatcacgg gcgtcgtgga ctatgagcac gtccgcgagc tggcccgcat    3960
caatggcgac ctgggccgcc tgggcggcct gctgaaactc tggctcaccg acgacccgcg    4020
cacggcgcgg ttcggtgatg ccacgatcct cgccctgctg gcgaagatcg aagagaagca    4080
ggacgagctt ggcaaggtca tgatgggcgt ggtccgcccg agggcagagc catgactttt    4140
ttagccgcta aaacggccgg ggggtgcgcg tgattgccaa gcacgtcccc atgcgctcca    4200
tcaagaagag cgacttcgcg gagctggtat tcgtgcaggg caagattcgg aataccaagt    4260
acgagaagga cggccagacg gtctacggga ccgacttcat tgccgataag gtggattatc    4320
tggacaccaa ggcaccaggc gggtcaaatc aggaataagg gcacattgcc ccggcgtgag    4380
tcggggcaat cccgcaagga gggtgaatga atcggacgtt tgaccggaag gcatacaggc    4440
aagaactgat cgacgcgggg ttttccgccg aggatgccga aaccatcgca agccgcaccg    4500
tcatgcgtgc gccccgcgaa accttccagt ccgtcggctc gatggtccag caagctacgg    4560
ccaagatcga gcgcgacagc gtgcaactgg ctccccctgc cctgcccgcg ccatcggccg    4620
ccgtggagcg ttcgcgtcgt ctcgaacagg aggcggcagg tttggcgaag tcgatgacca    4680
tcgacacgcg aggaactatg acgaccaaga agcgaaaaac cgccggcgag gacctggcaa    4740
aacaggtcag cgaggccaag caggccgcgt tgctgaaaca cacgaagcag cagatcaagg    4800
aaatgcagct ttccttgttc gatattgcgc cgtggccgga cacgatgcga gcgatgccaa    4860
acgacacggc ccgctctgcc ctgttcacca cgcgcaacaa gaaaatcccg cgcgaggcgc    4920
tgcaaaacaa ggtcattttc cacgtcaaca aggacgtgaa gatcacctac accggcgtcg    4980
agctgcgggc cgacgatgac gaactggtgt ggcagcaggt gttggagtac gcgaagcgca    5040
cccctatcgg cgagccgatc accttcacgt tctacgagct ttgccaggac ctgggctggt    5100
cgatcaatgg ccggtattac acgaaggccg aggaatgcct gtcgcgccta caggcgacgg    5160
cgatgggctt cacgtccgac gcgttgggc acctggaatc ggtgtcgctg ctgcaccgct    5220
tccgcgtcct ggaccgtggc aagaaaacgt cccgttgcca ggtcctgatc gacgaggaaa    5280
tcgtcgtgct gtttgctggc gaccactaca cgaaattcat atgggagaag taccgcaagc    5340
tgtcgccgac ggcccgacgg atgttcgact atttcagctc gcaccgggag ccgtacccgc    5400
tcaagctgga aaccttccgc ctcatgtgcg gatcggattc cacccgcgtg aagaagtggc    5460
gcgagcaggt cggcgaagcc tgcgaagagt tgcgaggcag cggcctggtg aacacgcctt    5520
gggtcaatga tgacctggtg cattgcaaac gctagggcct tgtggggtca gttccggctg    5580
ggggttcagc agccagcgct ttactggcat ttcaggaaca agcgggcact gctcgacgca    5640
cttgcttcgc tcagtatcgc tcgggacgca cggcgcgctc tacgaactgc cgataaacag    5700
```

```
aggattaaaa ttgacaattg tgattaaggc tcagattcga cggcttggag cggccgacgt    5760
gcaggatttc cgcgagatcc gattgtcggc cctgaagaaa gctccagaga tgttcgggtc    5820
cgtttacgag cacgaggaga aaaagcccat ggaggcgttc gctgaacggt tgcgagatgc    5880
cgtggcattc ggcgcctaca tcgacggcga gatcattggg ctgtcggtct tcaaacagga    5940
ggacggcccc aaggacgctc acaaggcgca tctgtccggc gttttcgtgg agcccgaaca    6000
gcgaggccga ggggtcgccg gtatgctgct gcgggcgttg ccggcgggtt tattgctcgt    6060
gatgatcgtc cgacagattc aacgggaat ctggtggatg cgcatcttca tcctcggcgc    6120
acttaatatt tcgctattct ggagcttgtt gtttatttcg gtctaccgcc tgccgggcgg    6180
ggtcgcggcg acggtaggcg ctgtgcagcc gctgatggtc gtgttcatct ctgccgctct    6240
gctaggtagc ccgatacgat tgatggcggt cctgggggct atttgcggaa ctgcgggcgt    6300
ggcgctgttg gtgttgacac caaacgcagc gctagatcct gtcggcgtcg cagcgggcct    6360 ggcggggggcg gtttccatgg cgttcggaac cgtgctgacc cgcaagtggc aacctcccgt    6420
gcctctgctc acctttaccg cctggcaact ggcggccgga ggacttctgc tcgttccagt    6480
agctttagtg tttgatccgc caatcccgat gcctacagga accaatgttc tcggcctggc    6540
gtggctcggc ctgatcggag cgggtttaac ctacttcctt tggttccggg ggatctcgcg    6600
actcgaacct acagttgttt ccttactggg cttctcagc cgggatggcg ctaagaagct    6660
attgccgccg atcttcatat gcggtgtgaa ataccgcaca gatgcgtaag gagaaaatac    6720
cgcatcaggc gctcttccgc ttcctcgctc actgactcgc tgcgctcggt cgttcggctg    6780
cggcgagcgg tatcagctca ctcaaaggcg gtaatacggt tatccacaga atcaggggat    6840
aacgcaggaa agaacatgtg agcaaaaggc cagcaaaagg ccaggaaccg taaaaaggcc    6900
gcgttgctgg cgtttttcca taggctccgc ccccctgacg agcatcacaa aaatcgacgc    6960
tcaagtcaga ggtggcgaaa cccgacagga ctataaagat accaggcgtt ccccctggaa    7020
agctccctcg tgcgctctcc tgttccgacc ctgccgctta ccggatacct gtccgccttt    7080
ctcccttcgg gaagcgtggc gctttctcaa tgctcacgct gtaggtatct cagttcggtg    7140
taggtcgttc gctccaagct gggctgtgtg cacgaacccc ccgttcagcc cgaccgctgc    7200
gccttatccg gtaactatcg tcttgagtcc aacccggtaa gacacgactt atcgccactg    7260
gcagcagcca ctggtaacag gattagcaga gcgaggtatg taggcggtgc tacagagttc    7320
ttgaagtggt ggcctaacta cggctacact agaaggacag tatttggtat ctgcgctctg    7380
ctgaagccag ttaccttcgg aaaaagagtt ggtagctctt gatccggcaa acaaaccacc    7440
gctggtagcg gtggtttttt tgtttgcaag cagcagatta cgcgcagaaa aaaaggatat    7500
caagaagatc ctttgatctt ttctacgggg tctgacgctc agtggaacga aaactcacgt    7560
taagggattt tggtcatgag attatcaaaa aggatcttca cctagatcct tttaaattaa    7620
aaatgaagtt ttaaatcaat ctaaagtata tatgagtaaa cttggtctga cagttaccaa    7680
tgcttaatca gtgaggcacc tatctcagcg atctgtctat ttcgttcatc catagttgcc    7740
tgactccccg tcgtgtagat aactacgata cgggagggct taccatctgg ccccagtgct    7800
gcaatgatac cgcgagaccc acgctcaccg gctccagatt tatcagcaat aaaccagcca    7860
gccggaaggg ccgagcgcag aagtggtcct gcaactttat ccgcctccat ccagtctatt    7920
aaacaagtgg cagcaacgga ttcgcaaacc tgtcacgcct tttgtgccaa agccgcgcc    7980 aggtttgcga tccgctgtgc caggcgttag gcgtcatatg aagatttcgg tgatccctga    8040
gcaggtggcg gaaacattgg atgctgagaa ccatttcatt gttcgtgaag tgttcgatgt    8100
```

```
gcacctatcc gaccaaggct ttgaactatc taccagaagt gtgagcccct accggaagga   8160
ttacatctcg gatgatgact ctgatgaaga ctctgcttgc tatggcgcat tcatcgacca   8220
agagcttgtc gggaagattg aactcaactc aacatggaac gatctagcct ctatcgaaca   8280
cattgttgtg tcgcacacgc accgaggcaa aggagtcgcg cacagtctca tcgaatttgc   8340
gaaaaagtgg gcactaagca gacagctcct tggcatacga ttagagacac aaacgaacaa   8400
tgtacctgcc tgcaatttgt acgcaaaatg tggctttact ctcggcggca ttgacctgtt   8460
cacgtataaa actagacctc aagtctcgaa cgaaacagcg atgtactggt actggttctc   8520
gggagcacag gatgacgcct aacaattcat tcaagccgac accgcttcgc ggcgcggctt   8580
aattcaggag ttaaacatca tgagggaagc ggtgatcgcc gaagtatcga ctcaactatc   8640
agaggtagtt ggcgtcatcg agcgccatct cgaaccgacg ttgctggccg tacatttgta   8700
cggctccgca gtggatggcg gcctgaagcc acacagtgat attgatttgc tggttacggt   8760
gaccgtaagg cttgatgaaa caacgcggcg agctttgatc aacgaccttt ggaaacttc   8820
ggcttcccct ggagagagcg agattctccg cgctgtagaa gtcaccattg ttgtgcacga   8880
cgacatcatt ccgtggcgtt atccagctaa gcgcgaactg caatttggag aatggcagcg   8940
caatgacatt cttgcaggta tcttcgagcc agccacgatc gacattgatc tggctatctt   9000
gctgacaaaa gcaagagaac atagcgttgc cttggtaggt ccagcggcgg aggaactctt   9060
tgatccggtt cctgaacagg atctatttga ggcgctaaat gaaaccttaa cgctatggaa   9120
ctcgccgccc gactgggctg gcgatgagcg aaatgtagtg cttacgttgt cccgcatttg   9180
gtacagcgca gtaaccggca aaatcgcgcc gaaggatgtc gctgccgact gggcaatgga   9240
gcgcctgccg gcccagtatc agcccgtcat acttgaagct aggcaggctt atcttggaca   9300
agaagatcgc ttggcctcgc gcgcagatca gttggaagaa tttgttcact acgtgaaagg   9360
cgagatcacc aaggtagtcg gcaaataatg tctaacaatt cgttcaagcc gacgccgctt   9420
cgcggcgcgg cttaactcaa gcgttagaga ctggggaag actatgcgcg atctgttgaa   9480
ggtggttcta agcctcgtac ttgcgatggc atcggggcag gcacttgctg acctgccaat   9540
tgttttagtg gatgaagctc gtcttcccta tgactactcc ccatccaact acgacatttc   9600
tccaagcaac tacgcaaact ccataagcaa ttacgacaat agtccatcaa attacgacaa   9660
ctctgagagc aactacgata atagttcatc caattacgac aatagtcgca acggaaatcg   9720
taggcttata tatagcgcaa atgggtctcg cactttcgcc ggctactacg tcattgccaa   9780
caatgggaca acgaacttct tttccacatc tggcaaaagg atgttctaca ccccaaaagg   9840
ggggcgcggc gtctatggcg gcaaagatgg gagcttctgc ggggcattgg tcgtcataaa   9900
tggccaattt tcgcttgccc tgacagataa cggcctgaag atcatgtatc taagcaacta   9960
gcctgctctc taataaaatg ttaggagctt ggctgccatt tttggggtga ggccgttcgc  10020
ggccgagggg cgcagcccct ggggggatgg gaggcccgcg ttagcgggcc gggagggttc  10080
gagaaggggg ggcaccccc ttcggcgtgc gcggtcacgc gccagggcgc agccctggtt  10140
aaaaacaagg tttataaata ttggtttaaa agcaggttaa aagacaggtt agcggtggcc  10200
gaaaaacggg cggaaccct tgcaaatgct ggattttctg cctgtggaca gcccctcaaa  10260
tgtcaatagg tgcgcccctc atctgtcagc actctgcccc tcaagtgtca aggatcgcgc  10320
ccctcatctg tcagtagtcg cgccctcaa gtgtcaatac cgcagggcac ttatccccag  10380
gcttgtccac atcatctgtg ggaaactcgc gtaaaatcag gcgttttcgc cgatttgcga  10440
ggctggccag ctccacgtcg ccggccgaaa tcgagcctgc ccctcatctg tcaacgccgc  10500
```

```
gccgggtgag tcggcccctc aagtgtcaac gtccgcccct catctgtcag tgagggccaa    10560
gttttccgcg aggtatccac aacgccggcg gccggccgcg gtgtctcgca cacggcttcg    10620
acggcgtttc tggcgcgttt gcagggccat agacggccgc cagcccagcg gcgagggcaa    10680
ccagcccggt gagcgtcgga aagggtcgac atcttgctgc gttcggatat tttcgtggag    10740
ttcccgccac agacccggat tgaaggcgag atccagcaac tcgcgccaga tcatcctgtg    10800
acggaacttt ggcgcgtgat gactggccag gacgtcggcc gaaagagcga caagcagatc    10860
acgattttcg acagcgtcgg atttgcgatc gaggattttt cggcgctgcg ctacgtccgc    10920
gaccgcgttg agggatcaag ccacagcagc ccactcgacc ttctagccga cccagacgag    10980
ccaagggatc tttttggaat gctgctccgt cgtcaggctt ccgacgtttt gggtggttga    11040
acagaagtca ttatcgtacg gaatgccagc actcccgagg ggaaccctgt ggttggcatg    11100
cacatacaaa tggacgaacg gataaacctt ttcacgccct tttaaatatc cgttattcta    11160
ataaacgctc ttttctctta ggtttacccg ccaatatatc ctgtcaaaca ctgatagttt    11220
aaactgaagg cgggaaacga caatctgatc atgagcggag aattaaggga gtcacgttat    11280
gacccccgcc gatgacgcgg gacaagccgt tttacgtttg gaactgacag aaccgcaacg    11340
attgaaggag ccactcagcc ccaatacgca aaccgcctct ccccgcgcgt tggccgattc    11400
attaatgcag ctggcacgac aggtttcccg actggaaagc gggcagtgag cgcaacgcaa    11460
ttaatgtgag ttagctcact cattaggcac cccaggcttt acactttatg cttccggctc    11520
gtatgttgtg tggaattgtg agcggataac aatttcacac aggaaacagc tatgaccatg    11580
attacgccaa gctatttagg tgacactata gaatactcaa gctatgcatc caacgcgttg    11640
ggagctctcc catatcgacc tgcaggcggc cgctcgacga attaattcca atcccacaaa    11700
aatctgagct taacagcaca gttgctcctc tcagagcaga atcgggtatt caacaccctc    11760
atatcaacta ctacgttgtg tataacggtc cacatgccgg tatatacgat gactggggtt    11820
gtacaaaggc ggcaacaaac ggcgttccg gagttgcaca caagaaattt gccactatta    11880
cagaggcaag agcagcagct gacgcgtaca caacaagtca gcaaacagac aggttgaact    11940 tcatcoccaa aggagaagct caactcaagc ccaagagctt gctaaggcc ctaacaagcc    12000 caccaaagca aaaagcccac tggctcacgc taggaaccaa aaggcccagc agtgatccag    12060
ccccaaaaga gatctccttt gccccggaga ttacaatgga cgatttcctc tatctttacg    12120
atctaggaag gaagttcgaa ggtgaaggtg acgacactat gttcaccact gataatgaga    12180
aggttagcct cttcaatttc agaaagaatg ctgacccaca gatggttaga gaggcctacg    12240
cagcaggtct catcaagacg atctacccga gtaacaatct ccaggagatc aaataccttc    12300
ccaagaaggt taaagatgca gtcaaaagat tcaggactaa ttgcatcaag aacacagaga    12360
aagacatatt tctcaagatc agaagtacta ttccagtatg gacgattcaa ggcttgcttc    12420
ataaaccaag gcaagtaata gagattggag tctctaaaaa ggtagttcct actgaatcta    12480
aggccatgca tggagtctaa gattcaaatc gaggatctaa cagaactcgc cgtgaagact    12540
ggcgaacagt tcatacagag tcttttacga ctcaatgaca agaagaaaat cttcgtcaac    12600
atggtggagc acgacactct ggtctactcc aaaaatgtca agatacagt ctcagaagac    12660 caaagggcta ttgagacttt tcaacaaagg ataatttcgg gaaacctcct cggattccat    12720
tgcccagcta tctgtcactt catcgaaagg acagtagaaa aggaaggtgg ctcctacaaa    12780
tgccatcatt gcgataaagg aaaggctatc attcaagatc tctctgccga cagtggtccc    12840
aaagatggac ccccacccac gaggagcatc gtggaaaaag aagacgttcc aaccacgtct    12900
```

```
tcaaagcaag tggattgatg tgacatctcc actgacgtaa gggatgacgc acaatcccac    12960
tatccttcgc aagacccttc ctctatataa ggaagttcat ttcatttgga gaggacacgc    13020
tcgaggctag catggatctc gggccccaaa taatgatttt attttgactg atagtgacct    13080
gttcgttgca acaaattgat gagcaatgct tttttataat gccaactttg tacaaaaaag    13140
ctgaacgaga aacgtaaaat gatataaata tcaatatatt aaattagatt ttgcataaaa    13200
aacagactac ataatactgt aaaacacaac atatccagtc actatgaatc aactacttag    13260
atggtattag tgacctgtag tcgaccgaca gccttccaaa tgttcttcgg gtgatgctgc    13320
caacttagtc gaccgacagc cttccaaatg ttcttctcaa acggaatcgt cgtatccagc    13380
ctactcgcta ttgtcctcaa tgccgtatta aatcataaaa agaaataaga aaaagaggtg    13440
cgagcctctt ttttgtgtga caaaataaaa acatctacct attcatatac gctagtgtca    13500
tagtcctgaa aatcatctgc atcaagaaca atttcacaac tcttatactt ttctcttaca    13560
agtcgttcgg cttcatctgg attttcagcc tctatactta ctaaacgtga taaagtttct    13620
gtaatttcta ctgtatcgac ctgcagactg gctgtgtata agggagcctg acatttatat    13680
tccccagaac atcaggttaa tggcgttttt gatgtcattt tcgcggtggc tgagatcagc    13740
cacttcttcc ccgataacgg agaccggcac actggccata tcggtggtca tcatgcgcca    13800
gctttcatcc ccgatatgca ccaccgggta aagttcacgg gagactttat ctgacagcag    13860
acgtgcactg gccaggggga tcaccatccg tcgcccgggc gtgtcaataa tatcactctg    13920
tacatccaca aacagacgat aacggctctc tcttttatag gtgtaaacct taaactgcat    13980
ttcaccagtc cctgttctcg tcagcaaaag agccgttcat ttcaataaac cgggcgacct    14040
cagccatccc ttcctgattt tccgcttttcc agcgttcggc acgcagacga cgggcttcat    14100
tctgcatggt tgtgcttacc agaccggaga tattgacatc atatatgcct tgagcaactg    14160
atagctgtcg ctgtcaactg tcactgtaat acgctgcttc atagcacacc tcttttttgac   14220 atacttcggg tagtgccgat caacgtctca ttttcgccaa aagttggccc agggcttccc    14280
ggtatcaaca gggacaccag gatttattta ttctgcgaag tgatcttccg tcacaggtat    14340
ttattcggcg caaagtgcgt cgggtgatgc tgccaactta gtcgactaca ggtcactaat    14400
accatctaag tagttgattc atagtgactg gatatgttgt gttttacagt attatgtagt    14460 ctgttttta tgcaaaatct aatttaatat attgatattt atatcatttt acgtttctcg     14520
ttcagctttc ttgtacaaag ttggcattat aagaaagcat tgcttatcaa tttgttgcaa    14580
cgaacaggtc actatcagtc aaaataaaat cattatttgc catccagctg cagctcctcg    14640
aggaattcgg tacccagct  tggtaaggaa ataattattt tctttttttcc ttttagtata   14700 aaatagttaa gtgatgttaa ttagtatgat tataataata tagttgttat aattgtgaaa    14760
aaataattta taaatatatt gtttacataa acaacatagt aatgtaaaaa aatatgacaa    14820
gtgatgtgta agacgaagaa gataaaagtt gagagtaagt atattatttt taatgaattt    14880
gatcgaacat gtaagatgat atactagcat taatatttgt tttaatcata atagtaattc    14940
tagctggttt gatgaattaa atatcaatga taaaatacta tagtaaaaat aagaataaat    15000
aaattaaaat aatatttttt tatgattaat agtttattat ataattaaat atctatacca    15060
ttactaaata ttttagttta aaagttaata aatatttgt tagaaattcc aatctgcttg     15120
taatttatca ataaacaaaa tattaaataa caagctaaag taacaaataa tatcaaacta    15180
atagaaacag taatcaatg taacaaaaca taatctaatg ctaatataac aaagcgcaag     15240
atctatcatt ttatatagta ttatttttcaa tcaacattct tattaattttc taaataatac   15300
```

```
ttgtagtttt attaacttct aaatggattg actattaatt aaatgaatta gtcgaacatg   15360
aataaacaag gtaacatgat agatcatgtc attgtgttat cattgatctt acatttggat   15420
tgattacagt tgggaagctg ggttcgaaat cgataagctt ggatcctcta gagagctgca   15480
gctggatggc aaataatgat tttattttga ctgatagtga cctgttcgtt gcaacaaatt   15540
gataagcaat gctttcttat aatgccaact ttgtacaaga aagctgaacg agaaacgtaa   15600
aatgatataa atatcaatat attaaattag attttgcata aaaaacagac tacataatac   15660
tgtaaaacac aacatatcca gtcactatga atcaactact tagatggtat tagtgacctg   15720
tagtcgacta agttggcagc atcacccgac gcactttgcg ccgaataaat acctgtgacg   15780
gaagatcact tcgcagaata aataaatcct ggtgtccctg ttgataccgg gaagccctgg   15840
gccaactttt ggcgaaaatg agacgttgat cggcactacc catttcacaa ctcttatact   15900
tttctcttac aagtcgttcg gcttcatctg gattttcagc ctctatactt actaaacgtg   15960
ataaagtttc tgtaatttct actgtatcga cctgcagact ggctgtgtat aagggagcct   16020
gacatttata ttccccagaa catcaggtta atggcgtttt tgatgtcatt ttcgcggtgg   16080
ctgagatcag ccacttcttc cccgataacg gagaccggca cactggccat atcggtggtc   16140
atcatgcgcc agctttcatc cccgatatgc accaccgggt aaagttcacg ggagacttta   16200
tctgacagca gacgtgcact ggccagggga tcaccatcc gtcgcccggg cgtgtcaata   16260
atatcactct gtacatccac aaacagacga taacggctct ctcttttata ggtgtaaacc   16320
ttaaactgca tttcaccagt ccctgttctc gtcagcaaaa gagccgttca tttcaataaa   16380
ccggcgacc tcagccatcc cttcctgatt ttccgctttc cagcgttcgg cacgcagacg   16440
acgggcttca ttctgcatgg ttgtgcttac cagaccggag atattgacat catatatgcc   16500
ttgagcaact gatagctgtc gctgtcaact gtcactgtaa tacgctgctt catagcacac   16560
ctctttttga catacttctg ttcttgatgc agatgatttt caggactatg acactagcgt   16620
atatgaatag gtagatgttt ttattttgtc acacaaaaaa gaggctcgca cctctttttc   16680
ttatttcttt ttatgattta atacggcatt gaggacaata gcgagtaggc tggatacgac   16740
gattccgttt gagaagaaca tttggaaggc tgtcggtcga ctaagttggc agcatcaccc   16800
gaagaacatt tggaaggctg tcggtcgact acaggtcact aataccatct aagtagttga   16860
ttcatagtga ctggatatgt tgtgttttac agtattatgt agtctgtttt ttatgcaaaa   16920
tctaatttaa tatattgata tttatatcat tttacgtttc tcgttcagct ttttgtaca   16980
aagttggcat tataaaaag cattgctcat caatttgttg caacgaacag gtcactatca   17040
gtcaaaataa aatcattatt tggggcccga gatccatgct agctctagag tcctgcttta   17100
atgagatatg cgagacgcct atgatcgcat gatatttgct ttcaattctg ttgtgcacgt   17160
tgtaaaaaac ctgagcatgt gtagctcaga tccttaccgc cggtttcggt tcattctaat   17220
gaatatatca cccgttacta tcgtattttt atgaataata ttctccgttc aatttactga   17280
ttgtacccta ctacttatat gtacaatatt aaaatgaaaa caatatattg tgctgaatag   17340
gtttatagcg acatctatga tagagcgcca caataacaaa caattgcgtt ttattattac   17400
aaatccaatt ttaaaaaaag cggcagaacc ggtcaaacct aaaagactga ttacataaat   17460
cttattcaaa tttcaaaagg ccccaggggc tagtatctac gacacaccga gcggcgaact   17520
aataacgttc actgaaggga actccggttc cccgccggcg cgcatgggtg agattccttg   17580
aagttgagta ttggccgtcc gctctaccga aagttacggg caccattcaa cccggtccag   17640
cacggcggcc gggtaaccga cttgctgccc cgagaattat gcagcatttt tttggtgtat   17700
```

-continued

```
gtgggcccca aatgaagtgc aggtcaaacc ttgacagtga cgacaaatcg ttgggcgggt      17760
ccagggcgaa ttttgcgaca acatgtcgag gctcagcagg acctgcaggc atgcaagcta      17820
gcttactagt gatgcatatt ctatagtgtc acctaaatct gc                         17862

<210> SEQ ID NO 24
<211> LENGTH: 17476
<212> TYPE: DNA
<213> ORGANISM: Artificial sequence
<220> FEATURE:
<223> OTHER INFORMATION: acceptor vector pHELLSGATE8

<400> SEQUENCE: 24
ggccgcacta gtgatatccc gcggccatgg cggccgggag catgcgacgt cgggcccaat        60
tcgccctata gtgagtcgta ttacaattca ctggccgtcg ttttacaacg tcgtgactgg       120
gaaaaccctg gcgttaccca acttaatcgc cttgcagcac atccccottt cgccagctgg       180 cgtaatagcg aagaggcccg caccgatcgc ccttcccaac agttgcgcag cctgaatggc       240
gaatggaaat tgtaaacgtt aatgggtttc tggagtttaa tgagctaagc acatacgtca       300
gaaaccatta ttgcgcgttc aaaagtcgcc taaggtcact atcagctagc aaatatttct       360
tgtcaaaaat gctccactga cgttccataa attcccctcg gtatccaatt agagtctcat       420
attcactctc aatccaaata atctgcaatg gcaattacct tatccgcaac ttctttacct       480
atttccgccc ggatccgggc aggttctccg gccgcttggg tggagaggct attcggctat       540
gactgggcac aacagacaat cggctgctct gatgccgccg tgttccggct gtcagcgcag       600
gggcgcccgg ttcttttttgt caagaccgac ctgtccggtg ccctgaatga actgcaggac       660
gaggcagcgc ggctatcgtg gctggccacg acgggcgttc cttgcgcagc tgtgctcgac       720
gttgtcactg aagcgggaag ggactggctg ctattgggcg aagtgccggg gcaggatctc       780
ctgtcatctc accttgctcc tgccgagaaa gtatccatca tggctgatgc aatgcggcgg       840
ctgcatacgc ttgatccggc tacctgccca ttcgaccacc aagcgaaaca tcgcatcgag       900
cgagcacgta ctcggatgga agccggtctt gtcgatcagg atgatctgga cgaagagcat       960
caggggctcg cgccagccga actgttcgcc aggctcaagg cgcgcatgcc cgacggcgag      1020
gatctcgtcg tgacccatgg cgatgcctgc ttgccgaata tcatggtgga aaatggccgc      1080
ttttctggat tcatcgactg tggccggctg ggtgtggcgg accgctatca ggacatagcg      1140
ttggctaccc gtgatattgc tgaagagctt ggcggcgaat gggctgaccg cttcctcgtg      1200
ctttacggta tcgccgctcc cgattcgcag cgcatcgcct tctatcgcct tcttgacgag      1260
ttcttctgag cgggactctg gggttcgaaa tgaccgacca agcgacgccc aacctgccat      1320
cacgagattt cgattccacc gccgccttct atgaaaggtt gggcttcgga atcgttttcc      1380
gggacgccgg ctggatgatc ctccagcgcg ggatctcat gctggagttc ttcgcccacc      1440
ccgatccaac acttacgttt gcaacgtcca agagcaaata gaccacgaac gcggaaggt      1500 tgccgcagcg tgtggattgc gtctcaattc tctcttgcag gaatgcaatg atgaatatga      1560
tactgactat gaaactttga gggaatactg cctagcaccg tcacctcata acgtgcatca      1620
tgcatgccct gacaacatgg aacatcgcta tttttctgaa gaattatgct cgttggagga      1680
tgtcgcggca attgcagcta ttgccaacat cgaactaccc ctcacgcatg cattcatcaa      1740
tattattcat gcggggaaag gcaagattaa tccaactggc aaatcatcca gcgtgattgg      1800
taacttcagt tccagcgact tgattcgttt tggtgctacc cacgttttca ataaggacga      1860
gatggtggag taaagaagga gtgcgtcgaa gcagatcgtt caaacatttg gcaataaagt      1920
```

```
ttcttaagat tgaatcctgt tgccggtctt gcgatgatta tcatataatt tctgttgaat    1980
tacgttaagc atgtaataat taacatgtaa tgcatgacgt tatttatgag atgggttttt    2040
atgattagag tcccgcaatt atacatttaa tacgcgatag aaaacaaaat atagcgcgca    2100
aactaggata aattatcgcg cgcggtgtca tctatgttac tagatcgaat taattccagg    2160
cggtgaaggg caatcagctg ttgcccgtct cactggtgaa aagaaaaacc accccagtac    2220
attaaaaacg tccgcaatgt gttattaagt tgtctaagcg tcaatttgtt tacaccacaa    2280
tatatcctgc caccagccag ccaacagctc cccgaccggc agctcggcac aaaatcacca    2340
ctcgatacag gcagcccatc agtccgggac ggcgtcagcg ggagagccgt tgtaaggcgg    2400
cagactttgc tcatgttacc gatgctattc ggaagaacgg caactaagct gccgggtttg    2460
aaacacggat gatctcgcgg agggtagcat gttgattgta acgatgacag agcgttgctg    2520
cctgtgatca aatatcatct ccctcgcaga gatccgaatt atcagccttc ttattcattt    2580
ctcgcttaac cgtgacaggc tgtcgatctt gagaactatg ccgacataat aggaaatcgc    2640
tggataaagc cgctgaggaa gctgagtggc gctatttctt tagaagtgaa cgttgacgat    2700
gtcgacggat cttttccgct gcataaccct gcttcggggt cattatagcg atttttttcgg    2760 tatatccatc cttttttcgca cgatatacag gattttgcca aagggttcgt gtagactttc    2820
cttggtgtat ccaacggcgt cagccgggca ggataggtga agtaggccca cccgcgagcg    2880
ggtgttcctt cttcactgtc ccttattcgc acctggcggt gctcaacggg aatcctgctc    2940
tgcgaggctg gccggctacc gccggcgtaa cagatgaggg caagcggatg gctgatgaaa    3000
ccaagccaac caggggtgat gctgccaact tactgattta gtgtatgatg gtgttttttga    3060 ggtgctccag tggcttctgt ttctatcagc tgtccctcct gttcagctac tgacggggtg    3120
gtgcgtaacg gcaaaagcac cgccggacat cagcgctatc tctgctctca ctgccgtaaa    3180
acatggcaac tgcagttcac ttacaccgct tctcaacccg gtacgcacca gaaaatcatt    3240
gatatggcca tgaatggcgt tggatgccgg gcaacagccc gcattatggg cgttggcctc    3300
aacacgattt tacgtcactt aaaaaactca ggccgcagtc ggtaacctcg cgcatacagc    3360
cgggcagtga cgtcatcgtc tgcgcggaaa tggacgaaca gtggggctat gtcgggcta    3420 aatcgcgcca cgctggctg ttttacgcgt atgacagtct ccggaagacg gttgttgcgc    3480
acgtattcgg tgaacgcact atggcgacgc tggggcgtct tatgagcctg ctgtcaccct    3540
ttgacgtggt gatatggatg acggatggct ggccgctgta tgaatcccgc ctgaagggaa    3600
agctgcacgt aatcagcaag cgatatacgc agcgaattga gcggcataac ctgaatctga    3660
ggcagcacct ggcacggctg ggacggaagt cgctgtcgtt ctcaaaatcg gtggagctgc    3720
atgacaaagt catcgggcat tatctgaaca taaaacacta tcaataagtt ggagtcatta    3780
cccaaccagg aagggcagcc cacctatcaa ggtgtactgc cttccagacg aacgaagagc    3840
gattgaggaa aaggcggcgg cggccggcat gagcctgtcg gcctacctgc tggccgtcgg    3900
ccagggctac aaaatcacgg gcgtcgtgga ctatgagcac gtccgcgagc tggcccgcat    3960
caatggcgac ctgggccgcc tgggcggcct gctgaaactc tggctcaccg acgacccgcg    4020
cacggcgcgg ttcggtgatg ccacgatcct cgccctgctg gcgaagatcg aagagaagca    4080
ggacgagctt ggcaaggtca tgatgggcgt ggtccgcccg agggcagagc catgactttt    4140
ttagccgcta aaacggccgg ggggtgcgcg tgattgccaa gcacgtcccc atgcgctcca    4200
tcaagaagag cgacttcgcg gagctggtat tcgtgcaggg caagattcgg aataccaagt    4260
acgagaagga cggccagacg gtctacggga ccgacttcat tgccgataag gtggattatc    4320
```

```
tggacaccaa ggcaccaggc gggtcaaatc aggaataagg gcacattgcc ccggcgtgag    4380
tcggggcaat cccgcaagga gggtgaatga atcggacgtt tgaccggaag gcatacaggc    4440
aagaactgat cgacgcgggg ttttccgccg aggatgccga aaccatcgca agccgcaccg    4500
tcatgcgtgc gccccgcgaa accttccagt ccgtcggctc gatggtccag caagctacgg    4560
ccaagatcga gcgcgacagc gtgcaactgg ctcccctgc cctgcccgcg ccatcggccg      4620
ccgtggagcg ttcgcgtcgt ctcgaacagg aggcggcagg tttggcgaag tcgatgacca    4680
tcgacacgcg aggaactatg acgaccaaga agcgaaaaac cgccggcgag gacctggcaa    4740
aacaggtcag cgaggccaag caggccgcgt tgctgaaaca cacgaagcag cagatcaagg    4800
aaatgcagct ttccttgttc gatattgcgc cgtggccgga cacgatgcga gcgatgccaa    4860
acgacacggc ccgtctctgcc ctgttcacca cgcgcaacaa gaaaatcccg cgcgaggcgc    4920
tgcaaaacaa ggtcattttc cacgtcaaca aggacgtgaa gatcacctac accggcgtcg    4980
agctgcgggc cgacgatgac gaactggtgt ggcagcaggt gttggagtac gcgaagcgca    5040
cccctatcgg cgagccgatc accttcacgt tctacgagct ttgccaggac ctgggctggt    5100
cgatcaatgg ccgtattac acgaaggccg aggaatgcct gtcgcgccta caggcgacgg      5160
cgatgggctt cacgtccgac cgcgttgggc acctggaatc ggtgtcgctg ctgcaccgct    5220
tccgcgtcct ggaccgtggc aagaaaacgt cccgttgcca ggtcctgatc gacgaggaaa    5280
tcgtcgtgct gtttgctggc gaccactaca cgaaattcat atgggagaag taccgcaagc    5340
tgtcgccgac ggcccgacgg atgttcgact atttcagctc gcaccgggag ccgtacccgc    5400
tcaagctgga aaccttccgc ctcatgtgcg gatcggattc caccgcgtg aagaagtggc       5460 gcgagcaggt cggcgaagcc tgcgaagagt tgcgaggcag cggcctggtg aacacgcct    5520 gggtcaatga tgacctggtg cattgcaaac gctagggcct tgtggggtca gttccggctg    5580
ggggttcagc agccagcgct ttactggcat tcaggaaca agcgggcact gctcgacgca     5640
cttgcttcgc tcagtatcgc tcgggacgca cggcgcgctc tacgaactgc cgataaacag    5700
aggattaaaa ttgacaattg tgattaaggc tcagattcga cggcttggag cggccgacgt    5760
gcaggatttc cgcgagatcc gattgtcggc cctgaagaaa gctccagaga tgttcgggtc    5820
cgtttacgag cacgaggaga aaaagcccat ggaggcgttc gctgaacggt tgcgagatgc    5880
cgtggcattc ggcgcctaca tcgacggcga gatcattggg ctgtcggtct tcaaacagga    5940
ggacggcccc aaggacgctc acaaggcgca tctgtccggc gttttcgtgg agcccgaaca    6000
gcgaggccga ggggtcgccg gtatgctgct gcgggcgttg ccggcgggtt tattgctcgt    6060
gatgatcgtc cgacagattc caacgggaat ctggtggatg cgcatcttca tcctcggcgc    6120
acttaatatt tcgctattct ggagcttgtt gtttatttcg gtctaccgcc tgccgggcgg    6180
ggtcgcggcg acggtaggcg ctgtgcagcc gctgatggtc gtgttcatct ctgccgctct    6240
gctaggtagc ccgatacgat tgatggcggt cctgggggct atttgcggaa ctgcgggcgt    6300
ggcgctgttg gtgttgacac caaacgcagc gctagatcct gtcggcgtcg cagcgggcct    6360
ggcggggggc gtttccatgg cgttcggaac cgtgctgacc gcaagtggc aacctcccgt       6420 gcctctgctc acctttaccg cctggcaact ggcggccgga ggacttctgc tcgttccagt    6480
agctttagtg tttgatccgc caatcccgat gcctacagga accaatgttc tcggcctggc    6540
gtggctcggc ctgatcggag cgggtttaac ctacttcctt tggttccggg ggatctcgcg    6600
actcgaacct acagttgttt ccttactggg cttttctcagc cggatgcgcg ctaagaagct    6660
attgccgccg atcttcatat gcggtgtgaa ataccgcaca gatgcgtaag gagaaaatac    6720
```

```
cgcatcaggc gctcttccgc ttcctcgctc actgactcgc tgcgctcggt cgttcggctg   6780
cggcgagcgg tatcagctca ctcaaaggcg gtaatacggt tatccacaga atcaggggat   6840
aacgcaggaa agaacatgtg agcaaaaggc cagcaaaagg ccaggaaccg taaaaaggcc   6900
gcgttgctgg cgtttttcca taggctccgc cccctgacg agcatcacaa aaatcgacgc    6960
tcaagtcaga ggtggcgaaa cccgacagga ctataaagat accaggcgtt ccccctgga   7020 agctccctcg tgcgctctcc tgttccgacc ctgccgctta ccggatacct gtccgccttt   7080
ctcccttcgg gaagcgtggc gctttctcaa tgctcacgct gtaggtatct cagttcggtg   7140
taggtcgttc gctccaagct gggctgtgtg cacgaacccc ccgttcagcc cgaccgctgc   7200
gccttatccg gtaactatcg tcttgagtcc aacccggtaa gacacgactt atcgccactg   7260
gcagcagcca ctggtaacag gattagcaga gcgaggtatg taggcggtgc tacagagttc   7320
ttgaagtggt ggcctaacta cggctacact agaaggacag tatttggtat ctgcgctctg   7380
ctgaagccag ttaccttcgg aaaaagagtt ggtagctctt gatccggcaa acaaaccacc   7440
gctggtagcg gtggttttt tgtttgcaag cagcagatta cgcgcagaaa aaaggatat    7500 caagaagatc ctttgatctt ttctacgggg tctgacgctc agtggaacga aaactcacgt   7560
taagggattt tggtcatgag attatcaaaa aggatcttca cctagatcct tttaaattaa   7620
aaatgaagtt ttaaatcaat ctaaagtata tatgagtaaa cttggtctga cagttaccaa   7680
tgcttaatca gtgaggcacc tatctcagcg atctgtctat ttcgttcatc catagttgcc   7740
tgactccccg tcgtgtagat aactacgata cgggagggct taccatctgg ccccagtgct   7800
gcaatgatac cgcgagaccc acgctcaccg gctccagatt tatcagcaat aaaccagcca   7860
gccggaaggg ccgagcgcag aagtggtcct gcaactttat ccgcctccat ccagtctatt   7920
aaacaagtgg cagcaacgga ttcgcaaacc tgtcacgcct tttgtgccaa agccgcgcc   7980 aggtttgcga tccgctgtgc caggcgttag gcgtcatatg aagatttcgg tgatccctga   8040
gcaggtggcg gaaacattgg atgctgagaa ccatttcatt gttcgtgaag tgttcgatgt   8100
gcacctatcc gaccaaggct ttgaactatc taccagaagt gtgagcccct accggaagga   8160
ttacatctcg gatgatgact ctgatgaaga ctctgcttgc tatggcgcat tcatcgacca   8220
agagcttgtc gggaagattg aactcaactc aacatggaac gatctagcct ctatcgaaca   8280
cattgttgtg tcgcacacgc accgaggcaa aggagtcgcg cacagtctca tcgaatttgc   8340
gaaaaagtgg gcactaagca gacagctcct tggcatacga ttagagacac aaacgaacaa   8400
tgtacctgcc tgcaatttgt acgcaaaatg tggctttact ctcggcggca ttgacctgtt   8460
cacgtataaa actagacctc aagtctcgaa cgaaacagcg atgtactggt actggttctc   8520
gggagcacag gatgacgcct aacaattcat tcaagccgac accgcttcgc ggcgcggctt   8580
aattcaggag ttaaacatca tgagggaagc ggtgatcgcc gaagtatcga ctcaactatc   8640
agaggtagtt ggcgtcatcg agcgccatct cgaaccgacg ttgctggccg tacatttgta   8700
cggctccgca gtggatggcg gcctgaagcc acacagtgat attgatttgc tggttacggt   8760
gaccgtaagg cttgatgaaa caacgcgcg agctttgatc aacgaccttt tggaaacttc   8820
ggcttcccct ggagagagcg agattctccg cgctgtagaa gtcaccattg ttgtgcacga   8880
cgacatcatt ccgtggcgtt atccagctaa gcgcgaactg caatttggag aatggcagcg   8940
caatgacatt cttgcaggta tcttcgagcc agccacgatc gacattgatc tggctatctt   9000
gctgacaaaa gcaagagaac atagcgttgc cttggtaggt ccagcggcgg aggaactctt   9060
tgatccggtt cctgaacagg atctatttga ggcgctaaat gaaaccttaa cgctatggaa   9120
```

-continued

```
ctcgccgccc gactgggctg gcgatgagcg aaatgtagtg cttacgttgt cccgcatttg    9180
gtacagcgca gtaaccggca aaatcgcgcc gaaggatgtc gctgccgact gggcaatgga    9240
gcgcctgccg gcccagtatc agcccgtcat acttgaagct aggcaggctt atcttggaca    9300
agaagatcgc ttggcctcgc gcgcagatca gttggaagaa tttgttcact acgtgaaagg    9360
cgagatcacc aaggtagtcg gcaaataatg tctaacaatt cgttcaagcc gacgccgctt    9420
cgcggcgcgg cttaactcaa gcgttagaga gctggggaag actatgcgcg atctgttgaa    9480
ggtggttcta agcctcgtac ttgcgatggc atcggggcag gcacttgctg acctgccaat    9540
tgttttagtg gatgaagctc gtcttcccta tgactactcc ccatccaact acgacatttc    9600
tccaagcaac tacgacaact ccataagcaa ttacgacaat agtccatcaa attacgacaa    9660
ctctgagagc aactacgata atagttcatc caattacgac aatagtcgca acggaaatcg    9720
taggcttata tatagcgcaa atgggtctcg cactttcgcc ggctactacg tcattgccaa    9780
caatgggaca acgaacttct tttccacatc tggcaaaagg atgttctaca ccccaaaagg    9840
ggggcgcggc gtctatggcg gcaaagatgg gagcttctgc ggggcattgg tcgtcataaa    9900
tggccaattt tcgcttgccc tgacagataa cggcctgaag atcatgtatc taagcaacta    9960
gcctgctctc taataaaatg ttaggagctt ggctgccatt tttggggtga ggccgttcgc   10020
ggccgagggg cgcagcccct gggggatgg gaggcccgcg ttagcgggcc gggagggttc   10080
gagaaggggg ggcacccccc ttcggcgtgc gcggtcacgc gccagggcgc agccctggtt   10140
aaaaacaagg tttataaata ttggtttaaa agcaggttaa aagacaggtt agcggtggcc   10200
gaaaaacggg cggaaaccct tgcaaatgct ggattttctg cctgtggaca gcccctcaaa   10260
tgtcaatagg tgcgcccctc atctgtcagc actctgcccc tcaagtgtca aggatcgcgc   10320
ccctcatctg tcagtagtcg cgcccctcaa gtgtcaatac cgcagggcac ttatccccag   10380
gcttgtccac atcatctgtg ggaaactcgc gtaaaatcag gcgttttcgc cgatttgcga   10440
ggctggccag ctccacgtcg ccggccgaaa tcgagcctgc ccctcatctg tcaacgccgc   10500
gccgggtgag tcggcccctc aagtgtcaac gtccgcccct catctgtcag tgagggccaa   10560
gttttccgcg aggtatccac aacgccggcg gccggccgcg gtgtctcgca cacggcttcg   10620
acggcgtttc tggcgcgttt gcagggccat agacggccgc cagcccagcg gcgagggcaa   10680
ccagcccggt gagcgtcgga aagggtcgac atcttgctgc gttcggatat tttcgtggag   10740
ttcccgccac agaccggat tgaaggcgag atccagcaac tcgcgccaga tcatcctgtg   10800
acggaacttt ggcgcgtgat gactggcag gacgtcggcc gaaagagcga caagcagatc   10860
acgattttcg acagcgtcgg atttgcgatc gaggattttt cggcgctgcg ctacgtccgc   10920
gaccgcgttg agggatcaag ccacagcagc ccactcgacc ttctagccga cccagacgag   10980
ccaagggatc tttttggaat gctgctccgt cgtcaggctt tccgacgttt ggtggttga    11040 acagaagtca ttatcgtacg gaatgccagc actcccgagg ggaaccctgt ggttggcatg   11100
cacatacaaa tggacgaacg gataaacctt ttcacgccct tttaaatatc cgttattcta   11160
ataaacgctc ttttctctta ggtttacccg ccaatatatc ctgtcaaaca ctgatagttt   11220
aaactgaagg cggaaaacga caatctgatc atgagcggag aattaaggga gtcacgttat   11280 gaccccgcc gatgacgcgg gacaagccgt tttacgtttg gaactgacag aaccgcaacg   11340
attgaaggag ccactcagcc ccaatacgca aaccgcctct cccgcgcgt tggccgattc   11400 attaatgcag ctggcacgac aggtttcccg actggaaagc gggcagtgag cgcaacgcaa   11460
ttaatgtgag ttagctcact cattaggcac cccaggcttt acactttatg cttccggctc   11520
```

```
gtatgttgtg tggaattgtg agcggataac aatttcacac aggaaacagc tatgaccatg   11580
attacgccaa gctatttagg tgacactata gaatactcaa gctatgcatc caacgcgttg   11640
ggagctctcc catatcgacc tgcaggcggc cgctcgacga attaattcca atcccacaaa   11700
aatctgagct taacagcaca gttgctcctc tcagagcaga atcgggtatt caacaccctc   11760
atatcaacta ctacgttgtg tataacggtc cacatgccgg tatatacgat gactggggtt   11820
gtacaaaggc ggcaacaaac ggcgttcccg gagttgcaca caagaaattt gccactatta   11880
cagaggcaag agcagcagct gacgcgtaca caacaagtca gcaaacagac aggttgaact   11940
tcatccccaa aggagaagct caactcaagc ccaagagctt tgctaaggcc ctaacaagcc   12000
caccaaagca aaaagcccac tggctcacgc taggaaccaa aaggcccagc agtgatccag   12060
ccccaaaaga gatctccttt gccccggaga ttacaatgga cgatttcctc tatctttacg   12120
atctaggaag gaagttcgaa ggtgaaggtg acgacactat gttcaccact gataatgaga   12180
aggttagcct cttcaatttc agaaagaatg ctgacccaca gatggttaga gaggcctacg   12240
cagcaggtct catcaagacg atctacccga gtaacaatct ccaggagatc aaataccttc   12300
ccaagaaggt taaagatgca gtcaaaagat tcaggactaa ttgcatcaag aacacagaga   12360
aagacatatt tctcaagatc agaagtacta ttccagtatg gacgattcaa ggcttgcttc   12420
ataaaccaag gcaagtaata gagattggag tctctaaaaa ggtagttcct actgaatcta   12480
aggccatgca tggagtctaa gattcaaatc gaggatctaa cagaactcgc cgtgaagact   12540
ggcgaacagt tcatacagag tcttttacga ctcaatgaca agaagaaaat cttcgtcaac   12600
atggtggagc acgacactct ggtctactcc aaaaatgtca agatacagt ctcagaagac   12660 caaagggcta ttgagacttt tcaacaaagg ataatttcgg gaaacctcct cggattccat   12720
tgcccagcta tctgtcactt catcgaaagg acagtagaaa aggaaggtgg ctcctacaaa   12780
tgccatcatt gcgataaagg aaaggctatc attcaagatc tctctgccga cagtggtccc   12840
aaagatggac ccccacccac gaggagcatc gtggaaaaag aagacgttcc aaccacgtct   12900
tcaaagcaag tggattgatg tgacatctcc actgacgtaa gggatgacgc acaatcccac   12960
tatccttcgc aagacccttc ctctatataa ggaagttcat ttcatttgga gaggacacgc   13020
tcgagacaag tttgtacaaa aaagctgaac gagaaacgta aaatgatata atatccaata   13080
tattaaatta gattttgcat aaaaaacaga ctacataata ctgtaaaaca caacatatcc   13140
agtcactatg aatcaactac ttagatggta ttagtgacct gtagtcgacc gacagccttc   13200
caaatgttct tcgggtgatg ctgccaactt agtcgaccga cagccttcca aatgttcttc   13260
tcaaacggaa tcgtcgtatc cagcctactc gctattgtcc tcaatgccgt attaaatcat   13320
aaaaagaaat aagaaaaaga ggtgcgagcc tcttttttgt gtgacaaaat aaaaacatct   13380
acctattcat atacgctagt gtcatagtcc tgaaaatcat ctgcatcaag aacaatttca   13440
caactcttat acttttctct tacaagtcgt tcggcttcat ctggattttc agcctctata   13500
cttactaaac gtgataaagt ttctgtaatt tctactgtat cgacctgcag actggctgtg   13560
tataagggag cctgacattt atattcccca gaacatcagg ttaatggcgt ttttgatgtc   13620
attttcgcgg tggctgagat cagccacttc ttccccgata acggagaccg gcacactggc   13680
catatcggtg gtcatcatgc gccagctttc atccccgata tgcaccaccg ggtaaagttc   13740
acgggagact ttatctgaca gcagacgtgc actggccagg gggatcacca tccgtcgccc   13800
gggcgtgtca ataatatcac tctgtacatc cacaaacaga cgataacggc tctctctttt   13860
ataggtgtaa accttaaact gcatttcacc agtccctgtt ctcgtcagca aaagagccgt   13920
```

```
tcatttcaat aaaccgggcg acctcagcca tcccttcctg attttccgct ttccagcgtt   13980
cggcacgcag acgacgggct tcattctgca tggttgtgct taccagaccg gagatattga   14040
catcatatat gccttgagca actgatagct gtcgctgtca actgtcactg taatacgctg   14100
cttcatagca caccctctttt tgacatactt cgggtagtgc cgatcaacgt ctcattttcg   14160
ccaaaagttg gcccagggct tcccggtatc aacagggaca ccaggattta tttattctgc   14220
gaagtgatct tccgtcacag gtatttattc ggcgcaaagt gcgtcgggtg atgctgccaa   14280
cttagtcgac tacaggtcac taataccatc taagtagttg attcatagtg actggatatg   14340
ttgtgtttta cagtattatg tagtctgttt tttatgcaaa atctaattta atatattgat   14400
atttatatca ttttacgttt ctcgttcagc tttcttgtac aaagtggtct cgaggaattc   14460
ggtaccccag cttggtaagg aaataattat tttcttttt ccttttagta taaaatagtt   14520
aagtgatgtt aattagtatg attataataa tatagttgtt ataattgtga aaaataatt   14580 tataaatata ttgtttacat aaacaacata gtaatgtaaa aaaatatgac aagtgatgtg   14640
taagacgaag aagataaaag ttgagagtaa gtatattatt tttaatgaat ttgatcgaac   14700
atgtaagatg atatactagc attaatattt gttttaatca taatagtaat tctagctggt   14760
ttgatgaatt aaatatcaat gataaaatac tatagtaaaa ataagaataa ataaattaaa   14820
ataatatttt tttatgatta atagtttatt atataattaa atatctatac cattactaaa   14880
tattttagtt taaaagttaa taaatatttt gttagaaatt ccaatctgct tgtaatttat   14940
caataaacaa aatattaaat aacaagctaa agtaacaaat aatatcaaac taatagaaac   15000
agtaatctaa tgtaacaaaa cataatctaa tgctaatata acaaagcgca agatctatca   15060
ttttatatag tattattttc aatcaacatt cttattaatt tctaaataat acttgtagtt   15120
ttattaactt ctaaatggat tgactattaa ttaaatgaat tagtcgaaca tgaataaaca   15180
aggtaacatg atagatcatg tcattgtgtt atcattgatc ttacatttgg attgattaca   15240
gttgggaagc tgggttcgaa atcgataagc ttggatcctc tagaccactt tgtacaagaa   15300
agctgaacga gaaacgtaaa atgatataaa tatcaatata ttaaattaga ttttgcataa   15360
aaaacagact acataaatact gtaaaacaca acatatccag tcactatgaa tcaactactt   15420
agatggtatt agtgacctgt agtcgactaa gttggcagca tcacccgacg cactttgcgc   15480
cgaataaata cctgtgacgg aagatcactt cgcagaataa ataaatcctg gtgtccctgt   15540
tgataccggg aagccctggg ccaacttttg gcgaaaatga gacgttgatc ggatttcaca   15600
actcttatac ttttctctta caagtcgttc ggcttcatct ggattttcag cctctatact   15660
tactaaacgt gataaagttt ctgtaatttc tactgtatcg acctgcagac tggctgtgta   15720
taagggagcc tgacatttat attccccaga acatcaggtt aatggcgttt ttgatgtcat   15780
tttcgcggtg gctgagatca gccacttctt ccccgataac ggagaccggc acactggcca   15840
tatcggtggt catcatgcgc cagctttcat ccccgatatg caccaccggg taaagttcac   15900
gggagacttt atctgacagc agacgtgcac tggccagggg gatcaccatc cgtcgcccgg   15960
gcgtgtcaat aatatcactc tgtacatcca caaacagacg ataacggctc tctcttttat   16020
aggtgtaaac cttaaactgc atttcaccag tccctgttct cgtcagcaaa agagccgttc   16080
atttcaataa accggcgac ctcagccatc ccttcctgat tttccgcttt ccagcgttcg   16140
gcacgcagac gacgggcttc attctgcatg gttgtgctta ccagaccgga gatattgaca   16200
tcatatatgc cttgagcaac tgatagctgt cgctgtcaac tgtcactgta atacgctgct   16260
tcatagcaca cctcttttg acatacttct gttcttgatg cagatgattt tcaggactat   16320
```

| | |
|---|---|
| gacactagcg tatatgaata ggtagatgtt tttattttgt cacacaaaaa agaggctcgc | 16380 |
| acctcttttt cttatttctt tttatgattt aatacggcat tgaggacaat agcgagtagg | 16440 |
| ctggatacga cgattccgtt tgagaagaac atttggaagg ctgtcggtcg actaagttgg | 16500 |
| cagcatcacc cgaagaacat ttggaaggct gtcggtcgac tacaggtcac taataccatc | 16560 |
| taagtagttg attcatagtg actggatatg ttgtgtttta cagtattatg tagtctgttt | 16620 |
| tttatgcaaa atcaatttta atatattgat atttatatca ttttacgttt ctcgttcagc | 16680 |
| ttttttgtac aaacttgtct agagtcctgc tttaatgaga tatgcgagac gcctatgatc | 16740 |
| gcatgatatt tgctttcaat tctgttgtgc acgttgtaaa aaacctgagc atgtgtagct | 16800 |
| cagatcctta ccgccggttt cggttcattc taatgaatat atcacccgtt actatcgtat | 16860 |
| ttttatgaat aatattctcc gttcaattta ctgattgtac cctactactt atatgtacaa | 16920 |
| tattaaaatg aaaacaatat attgtgctga ataggtttat agcgacatct atgatagagc | 16980 |
| gccacaataa caaacaattg cgttttatta ttacaaatcc aattttaaaa aaagcggcag | 17040 |
| aaccggtcaa acctaaaaga ctgattacat aaatcttatt caaatttcaa aaggccccag | 17100 |
| gggctagtat ctacgacaca ccgagcggcg aactaataac gttcactgaa gggaactccg | 17160 |
| gttccccgcc ggcgcgcatg ggtgagattc cttgaagttg agtattggcc gtccgctcta | 17220 |
| ccgaaagtta cgggcaccat tcaacccggt ccagcacggc ggccgggtaa ccgacttgct | 17280 |
| gccccgagaa ttatgcagca ttttttggt gtatgtgggc cccaaatgaa gtgcaggtca | 17340 |
| aaccttgaca gtgacgacaa atcgttgggc gggtccaggg cgaattttgc gacaacatgt | 17400 |
| cgaggctcag caggacctgc aggcatgcaa gctagcttac tagtgatgca tattctatag | 17460 |
| tgtcacctaa atctgc | 17476 |

```
<210> SEQ ID NO 25
<211> LENGTH: 17458
<212> TYPE: DNA
<213> ORGANISM: Artificial sequence
<220> FEATURE:
<223> OTHER INFORMATION: acceptor vector pHELLSGATE11

<400> SEQUENCE: 25
```

| | |
|---|---|
| ggccgcacta gtgatatccc gcggccatgg cggccgggag catgcgacgt cgggcccaat | 60 |
| tcgccctata gtgagtcgta ttacaattca ctggccgtcg ttttacaacg tcgtgactgg | 120 |
| gaaaaccctg gcgttaccca acttaatcgc cttgcagcac atcccccttt cgccagctgg | 180 |
| cgtaatagcg aagaggcccg caccgatcgc ccttcccaac agttgcgcag cctgaatggc | 240 |
| gaatggaaat tgtaaacgtt aatgggtttc tggagtttaa tgagctaagc acatacgtca | 300 |
| gaaaccatta ttgcgcgttc aaaagtcgcc taaggtcact atcagctagc aaatatttct | 360 |
| tgtcaaaaat gctccactga cgttccataa attcccctcg gtatccaatt agagtctcat | 420 |
| attcactctc aatccaaata atctgcaatg gcaattacct tatccgcaac ttctttacct | 480 |
| atttccgccc ggatccgggc aggttctccg gccgcttggg tggagaggct attcggctat | 540 |
| gactgggcac aacagacaat cggctgctct gatgccgccg tgttccggct gtcagcgcag | 600 |
| gggcgcccgg ttcttttgt caagaccgac ctgtccggtg ccctgaatga actgcaggac | 660 |
| gaggcagcgc ggctatcgtg gctggccacg acgggcgttc cttgcgcagc tgtgctcgac | 720 |
| gttgtcactg aagcgggaag ggactggctg ctattgggcg aagtgccggg gcaggatctc | 780 |
| ctgtcatctc accttgctcc tgccgagaaa gtatccatca tggctgatgc aatgcggcgg | 840 |
| ctgcatacgc ttgatccggc tacctgccca ttcgaccacc aagcgaaaca tcgcatcgag | 900 |

```
cgagcacgta ctcggatgga agccggtctt gtcgatcagg atgatctgga cgaagagcat    960
caggggctcg cgccagccga actgttcgcc aggctcaagg cgcgcatgcc cgacggcgag   1020
gatctcgtcg tgacccatgg cgatgcctgc ttgccgaata tcatggtgga aaatggccgc   1080
ttttctggat tcatcgactg tggccggctg ggtgtggcgg accgctatca ggacatagcg   1140
ttggctaccc gtgatattgc tgaagagctt ggcggcgaat gggctgaccg cttcctcgtg   1200
ctttacggta tcgccgctcc cgattcgcag cgcatcgcct tctatcgcct tcttgacgag   1260
ttcttctgag cgggactctg gggttcgaaa tgaccgacca agcgacgccc aacctgccat   1320
cacgagattt cgattccacc gccgccttct atgaaaggtt gggcttcgga atcgttttcc   1380
gggacgccgg ctggatgatc ctccagcgcg gggatctcat gctggagttc ttcgcccacc   1440
ccgatccaac acttacgttt gcaacgtcca agagcaaata gaccacgaac gccggaaggt   1500
tgccgcagcg tgtggattgc gtctcaattc tctcttgcag gaatgcaatg atgaatatga   1560
tactgactat gaaactttga gggaatactg cctagcaccg tcacctcata acgtgcatca   1620
tgcatgccct gacaacatgg aacatcgcta ttttctgaa gaattatgct cgttggagga   1680
tgtcgcggca attgcagcta ttgccaacat cgaactaccc ctcacgcatg cattcatcaa   1740
tattattcat gcggggaaag gcaagattaa tccaactggc aaatcatcca gcgtgattgg   1800
taacttcagt tccagcgact tgattcgttt tggtgctacc cacgttttca ataaggacga   1860
gatggtggag taaagaagga gtgcgtcgaa gcagatcgtt caaacatttg caataaagt   1920
ttcttaagat tgaatcctgt tgccggtctt cgatgatta tcatataatt tctgttgaat   1980
tacgttaagc atgtaataat taacatgtaa tgcatgacgt tatttatgag atgggttttt   2040
atgattagag tcccgcaatt atacatttaa tacgcgatag aaaacaaaat atagcgcgca   2100
aactaggata aattatcgcg cgcggtgtca tctatgttac tagatcgaat taattccagg   2160
cggtgaaggg caatcagctg ttgcccgtct cactggtgaa aagaaaaacc accccagtac   2220
attaaaaacg tccgcaatgt gttattaagt tgtctaagcg tcaatttgtt tacaccacaa   2280
tatatcctgc caccagccag ccaacagctc cccgaccggc agctcggcac aaaatcacca   2340
ctcgatacag gcagcccatc agtccgggac ggcgtcagcg ggagagccgt tgtaaggcgg   2400
cagactttgc tcatgttacc gatgctattc ggaagaacgg caactaagct gccgggtttg   2460
aaacacggat gatctcgcgg agggtagcat gttgattgta acgatgacag agcgttgctg   2520
cctgtgatca aatatcatct ccctcgcaga gatccgaatt atcagccttc ttattcattt   2580
ctcgcttaac cgtgacaggc tgtcgatctt gagaactatg ccgacataat aggaaatcgc   2640
tggataaagc cgctgaggaa gctgagtggc gctatttctt tagaagtgaa cgttgacgat   2700
gtcgacggat cttttccgct gcataaccct gcttcggggt cattatagcg attttttcgg   2760
tatatccatc cttttttcgca cgatatacag gattttgcca aagggttcgt gtagactttc   2820
cttggtgtat ccaacggcgt cagccgggca ggataggtga agtaggccca cccgcgagcg   2880
ggtgttcctt cttcactgtc ccttattcgc acctggcggt gctcaacggg aatcctgctc   2940
tgcgaggctg gccggctacc gccggcgtaa cagatgaggg caagcggatg gctgatgaaa   3000
ccaagccaac caggggtgat gctgccaact tactgattta gtgtatgatg gtgttttttga   3060
ggtgctccag tggcttctgt ttctatcagc tgtccctcct gttcagctac tgacggggtg   3120
gtgcgtaacg gcaaaagcac cgccggacat cagcgctatc tctgctctca ctgccgtaaa   3180
acatggcaac tgcagttcac ttacaccgct tctcaacccg gtacgcacca gaaaatcatt   3240
gatatggcca tgaatggcgt tggatgccgg gcaacagccc gcattatggg cgttggcctc   3300
```

-continued

```
aacacgattt tacgtcactt aaaaaactca ggccgcagtc ggtaacctcg cgcatacagc    3360
cgggcagtga cgtcatcgtc tgcgcggaaa tggacgaaca gtggggctat gtcgggcta     3420 aatcgcgcca gcgctggctg ttttacgcgt atgacagtct ccggaagacg gttgttgcgc    3480
acgtattcgg tgaacgcact atggcgacgc tgggcgtct tatgagcctg ctgtcaccct     3540
ttgacgtggt gatatggatg acggatggct ggccgctgta tgaatcccgc ctgaagggaa    3600
agctgcacgt aatcagcaag cgatatacgc agcgaattga gcggcataac ctgaatctga    3660
ggcagcacct ggcacggctg ggacggaagt cgctgtcgtt ctcaaaatcg gtggagctgc    3720
atgacaaagt catcgggcat tatctgaaca taaaacacta tcaataagtt ggagtcatta    3780
cccaaccagg aagggcagcc cacctatcaa ggtgtactgc cttccagacg aacgaagagc    3840
gattgaggaa aaggcggcgg cggccggcat gagcctgtcg gcctacctgc tggccgtcgg    3900
ccagggctac aaaatcacgg gcgtcgtgga ctatgagcac gtccgcgagc tggcccgcat    3960
caatggcgac ctgggccgcc tgggcggcct gctgaaactc tggctcaccg acgacccgcg    4020
cacggcgcgg ttcggtgatg ccacgatcct cgccctgctg gcgaagatcg aagagaagca    4080
ggacgagctt ggcaaggtca tgatgggcgt ggtccgcccg agggcagagc catgactttt    4140
ttagccgcta aaacggccgg ggggtgcgcg tgattgccaa gcacgtcccc atgcgctcca    4200
tcaagaagag cgacttcgcg gagctggtat tcgtgcaggg caagattcgg aataccaagt    4260
acgagaagga cggccagacg gtctacggga ccgacttcat tgccgataag gtggattatc    4320
tggacaccaa ggcaccaggc gggtcaaatc aggaataagg gcacattgcc ccggcgtgag    4380
tcggggcaat cccgcaagga gggtgaatga atcggacgtt tgaccggaag gcatacaggc    4440
aagaactgat cgacgcgggg ttttccgccg aggatgccga aaccatcgca agccgcaccg    4500
tcatgcgtgc gccccgcgaa accttccagt ccgtcggctc gatggtccag caagctacgg    4560
ccaagatcga gcgcgacagc gtgcaactgg ctcccctgc cctgcccgcg ccatcggccg     4620
ccgtggagcg ttcgcgtcgt ctcgaacagg aggcggcagg tttggcgaag tcgatgacca    4680
tcgacacgcg aggaactatg acgaccaaga agcgaaaaac cgccggcgag gacctggcaa    4740
aacaggtcag cgaggccaag caggccgcgt tgctgaaaca cacgaagcag cagatcaagg    4800
aaatgcagct ttccttgttc gatattgcgc cgtggccgga cacgatgcga gcgatgccaa    4860
acgacacggc ccgctctgcc ctgttcacca cgcgcaacaa gaaaatcccg cgcgaggcgc    4920
tgcaaaacaa ggtcattttc cacgtcaaca aggacgtgaa gatcacctac accggcgtcg    4980
agctgcgggc cgacgatgac gaactggtgt ggcagcaggt gttggagtac gcgaagcgca    5040 ccccctatcgg cgagccgatc accttcacgt tctacgagct ttgccaggac ctgggctggt    5100
cgatcaatgg ccggtattac acgaaggccg aggaatgcct gtcgcgccta caggcgacgg    5160
cgatgggctt cacgtccgac cgcgttgggc acctggaatc ggtgtcgctg ctgcaccgct    5220
tccgcgtcct ggaccgtggc aagaaaacgt cccgttgcca ggtcctgatc gacgaggaaa    5280
tcgtcgtgct gtttgctggc gaccactaca cgaaattcat atgggagaag taccgcaagc    5340
tgtcgccgac ggcccgacgg atgttcgact atttcagctc gcaccgggag ccgtacccgc    5400
tcaagctgga aaccttccgc ctcatgtgcg gatcggattc cacccgcgtg aagaagtggc    5460
gcgagcaggt cggcgaagcc tgcgaagagt tgcgaggcag cggcctggtg aacacgcctt    5520
gggtcaatga tgacctggtg cattgcaaac gctagggcct tgtgggtgtca gttccggctg    5580 ggggttcagc agccagcgct ttactggcat ttcaggaaca agcgggcact gctcgacgca    5640
cttgcttcgc tcagtatcgc tcgggacgca cggcgcgctc tacgaactgc cgataaacag    5700
```

```
aggattaaaa ttgacaattg tgattaaggc tcagattcga cggcttggag cggccgacgt   5760
gcaggatttc cgcgagatcc gattgtcggc cctgaagaaa gctccagaga tgttcgggtc   5820
cgtttacgag cacgaggaga aaaagcccat ggaggcgttc gctgaacggt tgcgagatgc   5880
cgtggcattc ggcgcctaca tcgacggcga gatcattggg ctgtcggtct tcaaacagga   5940
ggacggcccc aaggacgctc acaaggcgca tctgtccggc gttttcgtgg agcccgaaca   6000
gcgaggccga ggggtcgccg gtatgctgct gcgggcgttg ccggcgggtt tattgctcgt   6060
gatgatcgtc cgacagattc aacgggaat ctggtggatg cgcatcttca tcctcggcgc   6120
acttaatatt tcgctattct ggagcttgtt gtttatttcg gtctaccgcc tgccgggcgg   6180
ggtcgcggcg acggtaggcg ctgtgcagcc gctgatggtc gtgttcatct ctgccgctct   6240
gctaggtagc ccgatacgat tgatggcggt cctgggggct atttgcggaa ctgcgggcgt   6300
ggcgctgttg gtgttgacac caaacgcagc gctagatcct gtcggcgtcg cagcgggcct   6360 ggcggggcg gtttccatgg cgttcggaac cgtgctgacc cgcaagtggc aacctcccgt   6420
gcctctgctc acctttaccg cctggcaact ggcggccgga ggacttctgc tcgttccagt   6480
agctttagtg tttgatccgc caatcccgat gcctacagga accaatgttc tcggcctggc   6540
gtggctcggc ctgatcggag cgggtttaac ctacttcctt tggttccggg ggatctcgcg   6600
actcgaacct acagttgttt ccttactggg ctttctcagc cgggatggcg ctaagaagct   6660
attgccgccg atcttcatat gcggtgtgaa ataccgcaca gatgcgtaag gagaaaatac   6720
cgcatcaggc gctcttccgc ttcctcgctc actgactcgc tgcgctcggt cgttcggctg   6780
cggcgagcgg tatcagctca ctcaaaggcg gtaatacggt tatccacaga atcaggggat   6840
aacgcaggaa agaacatgtg agcaaaaggc cagcaaaagg ccaggaaccg taaaaaggcc   6900
gcgttgctgg cgttttccca taggctccgc cccctgacg agcatcacaa aaatcgacgc   6960
tcaagtcaga ggtggcgaaa cccgacagga ctataaagat accaggcgtt ccccctgga   7020 agctccctcg tgcgctctcc tgttccgacc ctgccgctta ccggatacct gtccgccttt   7080
ctcccttcgg gaagcgtggc gctttctcaa tgctcacgct gtaggtatct cagttcggtg   7140
taggtcgttc gctccaagct gggctgtgtg cacgaacccc ccgttcagcc cgaccgctgc   7200
gccttatccg gtaactatcg tcttgagtcc aacccggtaa gacacgactt atcgccactg   7260
gcagcagcca ctggtaacag gattagcaga gcgaggtatg taggcggtgc tacagagttc   7320
ttgaagtggt ggcctaacta cggctacact agaaggacag tatttggtat ctgcgctctg   7380
ctgaagccag ttaccttcgg aaaaagagtt ggtagctctt gatccggcaa acaaaccacc   7440
gctggtagcg gtggtttttt tgtttgcaag cagcagatta cgcgcagaaa aaaaggatat   7500
caagaagatc ctttgatctt ttctacgggg tctgacgctc agtggaacga aaactcacgt   7560
taagggattt tggtcatgag attatcaaaa aggatcttca cctagatcct tttaaattaa   7620
aaatgaagtt ttaaatcaat ctaaagtata tatgagtaaa cttggtctga cagttaccaa   7680
tgcttaatca gtgaggcacc tatctcagcg atctgtctat ttcgttcatc catagttgcc   7740
tgactccccg tcgtgtagat aactacgata cgggagggct taccatctgg ccccagtgct   7800
gcaatgatac cgcgagaccc acgctcaccg gctccagatt tatcagcaat aaaccagcca   7860 gccgaaggg ccgagcgcag aagtggtcct gcaactttat ccgcctccat ccagtctatt   7920
aaacaagtgg cagcaacgga ttcgcaaacc tgtcacgcct tttgtgccaa agccgcgcc   7980 aggtttgcga tccgctgtgc caggcgttag gcgtcatatg aagatttcgg tgatccctga   8040
gcaggtggcg gaaacattgg atgctgagaa ccatttcatt gttcgtgaag tgttcgatgt   8100
```

```
gcacctatcc gaccaaggct ttgaactatc taccagaagt gtgagcccct accggaagga   8160
ttacatctcg gatgatgact ctgatgaaga ctctgcttgc tatggcgcat tcatcgacca   8220
agagcttgtc gggaagattg aactcaactc aacatggaac gatctagcct ctatcgaaca   8280
cattgttgtg tcgcacacgc accgaggcaa aggagtcgcg cacagtctca tcgaatttgc   8340
gaaaaagtgg gcactaagca gacagctcct tggcatacga ttagagacac aaacgaacaa   8400
tgtacctgcc tgcaatttgt acgcaaaatg tggctttact ctcggcggca ttgacctgtt   8460
cacgtataaa actagacctc aagtctcgaa cgaaacagcg atgtactggt actggttctc   8520
gggagcacag gatgacgcct aacaattcat tcaagccgac accgcttcgc ggcgcggctt   8580
aattcaggag ttaaacatca tgagggaagc ggtgatcgcc gaagtatcga ctcaactatc   8640
agaggtagtt ggcgtcatcg agcgccatct cgaaccgacg ttgctggccg tacatttgta   8700
cggctccgca gtggatggcg gcctgaagcc acacagtgat attgatttgc tggttacggt   8760
gaccgtaagg cttgatgaaa caacgcggcg agctttgatc aacgaccttt tggaaacttc   8820
ggcttcccct ggagagagcg agattctccg cgctgtagaa gtcaccattg ttgtgcacga   8880
cgacatcatt ccgtggcgtt atccagctaa gcgcgaactg caatttggag aatggcagcg   8940
caatgacatt cttgcaggta tcttcgagcc agccacgatc gacattgatc tggctatctt   9000
gctgacaaaa gcaagagaac atagcgttgc cttggtaggt ccagcggcgg aggaactctt   9060
tgatccggtt cctgaacagg atctatttga ggcgctaaat gaaaccttaa cgctatggaa   9120
ctcgccgccc gactgggctg gcgatgagcg aaatgtagtg cttacgttgt cccgcatttg   9180
gtacagcgca gtaaccggca aaatcgcgcc gaaggatgtc gctgccgact gggcaatgga   9240
gcgcctgccg gcccagtatc agcccgtcat acttgaagct aggcaggctt atcttggaca   9300
agaagatcgc ttggcctcgc gcgcagatca gttggaagaa tttgttcact acgtgaaagg   9360
cgagatcacc aaggtagtcg gcaaataatg tctaacaatt cgttcaagcc gacgccgctt   9420
cgcggcgcgg cttaactcaa gcgttagaga gctggggaag actatgcgcg atctgttgaa   9480
ggtggttcta agcctcgtac ttgcgatggc atcggggcag gcacttgctg acctgccaat   9540
tgttttagtg gatgaagctc gtcttcccta tgactactcc ccatccaact acgacatttc   9600
tccaagcaac tacgacaact ccataagcaa ttacgacaat agtccatcaa attacgacaa   9660
ctctgagagc aactacgata atagttcatc caattacgac aatagtcgca acggaaatcg   9720
taggcttata tatagcgcaa atgggtctcg cactttcgcc ggctactacg tcattgccaa   9780
caatgggaca acgaacttct tttccacatc tggcaaaagg atgttctaca ccccaaaagg   9840
ggggcgcggc gtctatggcg gcaaagatgg gagcttctgc ggggcattgg tcgtcataaa   9900
tggccaattt tcgcttgccc tgacagataa cggcctgaag atcatgtatc taagcaacta   9960
gcctgctctc taataaaatg ttaggagctt ggctgccatt tttggggtga ggccgttcgc  10020
ggccgagggg cgcagcccct gggggatgg gaggcccgcg ttagcgggcc gggagggttc  10080 gagaagggg ggcaccccc ttcggcgtgc gcggtcacgc gccagggcgc agccctggtt  10140
aaaaacaagg tttataaata ttggtttaaa agcaggttaa aagacaggtt agcggtggcc  10200
gaaaaacggg cggaaccct tgcaaatgct ggattttctg cctgtggaca gcccctcaaa  10260
tgtcaatagg tgcgcccctc atctgtcagc actctgcccc tcaagtgtca aggatcgcgc  10320
ccctcatctg tcagtagtcg cgcccctcaa gtgtcaatac cgcagggcac ttatccccag  10380
gcttgtccac atcatctgtg ggaaactcgc gtaaaatcag gcgttttcgc cgatttgcga  10440
ggctggccag ctccacgtcg ccggccgaaa tcgagcctgc ccctcatctg tcaacgccgc  10500
```

```
gccgggtgag tcggcccctc aagtgtcaac gtccgcccct catctgtcag tgagggccaa    10560
gttttccgcg aggtatccac aacgccggcg gccggccgcg gtgtctcgca cacggcttcg    10620
acggcgtttc tggcgcgttt gcagggccat agacggccgc cagcccagcg gcgagggcaa    10680
ccagcccggt gagcgtcgga aagggtcgac atcttgctgc gttcggatat tttcgtggag    10740
ttcccgccac agacccggat tgaaggcgag atccagcaac tcgcgccaga tcatcctgtg    10800
acggaacttt ggcgcgtgat gactggccag gacgtcggcc gaaagagcga caagcagatc    10860
acgattttcg acagcgtcgg atttgcgatc gaggattttt cggcgctgcg ctacgtccgc    10920
gaccgcgttg agggatcaag ccacagcagc ccactcgacc ttctagccga cccagacgag    10980
ccaagggatc tttttggaat gctgctccgt cgtcaggctt ccgacgtttt gggtggttga    11040
acagaagtca ttatcgtacg gaatgccagc actcccgagg ggaaccctgt ggttggcatg    11100
cacatacaaa tggacgaacg gataaacctt ttcacgccct tttaaatatc cgttattcta    11160
ataaacgctc ttttctctta ggtttacccg ccaatatatc ctgtcaaaca ctgatagttt    11220
aaactgaagg cgggaaacga caatctgatc atgagcggag aattaaggga gtcacgttat    11280 gaccccccgcc gatgacgcgg gacaagccgt tttacgtttg gaactgacag aaccgcaacg    11340
attgaaggag ccactcagcc ccaatacgca aaccgcctct ccccgcgcgt tggccgattc    11400
attaatgcag ctggcacgac aggtttcccg actggaaagc gggcagtgag cgcaacgcaa    11460
ttaatgtgag ttagctcact cattaggcac cccaggcttt acactttatg cttccggctc    11520
gtatgttgtg tggaattgtg agcggataac aatttcacac aggaaacagc tatgaccatg    11580
attacgccaa gctatttagg tgacactata gaatactcaa gctatgcatc caacgcgttg    11640
ggagctctcc catatcgacc tgcaggcggc cgctcgacga attaattcca atcccacaaa    11700
aatctgagct taacagcaca gttgctcctc tcagagcaga atcgggtatt caacaccctc    11760
atatcaacta ctacgttgtg tataacggtc cacatgccgg tatatacgat gactgggggtt    11820 gtacaaaggc ggcaacaaac ggcgttccgc gagttgcaca caagaaattt gccactatta    11880
cagaggcaag agcagcagct gacgcgtaca caacaagtca gcaaacagac aggttgaact    11940
tcatccccaa aggagaagct caactcaagc ccaagagctt tgctaaggcc ctaacaagcc    12000
caccaaagca aaaagcccac tggctcacgc taggaaccaa aaggcccagc agtgatccag    12060
ccccaaaaga gatctccttt gccccggaga ttacaatgga cgatttcctc tatctttacg    12120
atctaggaag gaagttcgaa ggtgaaggtg acgacactat gttcaccact gataatgaga    12180
aggttagcct cttcaatttc agaaagaatg ctgacccaca gatggttaga gaggcctacg    12240
cagcaggtct catcaagacg atctacccga gtaacaatct ccaggagatc aaataccttc    12300
ccaagaaggt taaagatgca gtcaaaagat tcaggactaa ttgcatcaag aacacagaga    12360
aagacatatt tctcaagatc agaagtacta ttccagtatg gacgattcaa ggcttgcttc    12420 ataaccaag gcaagtaata gagattggag tctctaaaaa ggtagttcct actgaatcta    12480
aggccatgca tggagtctaa gattcaaatc gaggatctaa cagaactcgc cgtgaagact    12540
ggcgaacagt tcatacagag tcttttacga ctcaatgaca agaagaaaat cttcgtcaac    12600
atggtggagc acgacactct ggtctactcc aaaaatgtca agatacagt ctcagaagac    12660 caaagggcta ttgagacttt tcaacaaagg ataatttcgg gaaacctcct cggattccat    12720
tgcccagcta tctgtcactt catcgaaagg acagtagaaa aggaaggtgg ctcctacaaa    12780
tgccatcatt gcgataaagg aaaggctatc attcaagatc tctctgccga cagtggtccc    12840
aaagatggac ccccacccac gaggagcatc gtggaaaaag aagacgttcc aaccacgtct    12900
```

```
tcaaagcaag tggattgatg tgacatctcc actgacgtaa gggatgacgc acaatcccac   12960
tatccttcgc aagacccttc ctctatataa ggaagttcat ttcatttgga gaggacacgc   13020
tcgagacaag tttgtacaaa aaagctgaac gagaaacgta aaatgatata aatatcaata   13080
tattaaatta gattttgcat aaaaaacaga ctacataata ctgtaaaaca caacatatcc   13140
agtcactatg aatcaactac ttagatggta ttagtgacct gtagtcgacc gacagccttc   13200
caaatgttct tcgggtgatg ctgccaactt agtcgaccga cagccttcca aatgttcttc   13260
tcaaacggaa tcgtcgtatc cagcctactc gctattgtcc tcaatgccgt attaaatcat   13320
aaaaagaaat aagaaaaaga ggtgcgagcc tcttttttgt gtgacaaaat aaaaacatct   13380
acctattcat atacgctagt gtcatagtcc tgaaaatcat ctgcatcaag aacaatttca   13440
caactcttat acttttctct tacaagtcgt tcggcttcat ctggattttc agcctctata   13500
cttactaaac gtgataaagt ttctgtaatt tctactgtat cgacctgcag actggctgtg   13560
tataagggag cctgacattt atattcccca gaacatcagg ttaatggcgt ttttgatgtc   13620
attttcgcgg tggctgagat cagccacttc ttccccgata acggagaccg gcacactggc   13680
catatcggtg gtcatcatgc gccagctttc atccccgata tgcaccaccg ggtaaagttc   13740
acgggagact ttatctgaca gcagacgtgc actggccagg gggatcacca tccgtcgccc   13800
gggcgtgtca ataatatcac tctgtacatc cacaaacaga cgataacggc tctctctttt   13860
ataggtgtaa accttaaact gcatttcacc agtccctgtt ctcgtcagca aaagagccgt   13920
tcatttcaat aaaccgggcg acctcagcca tcccttcctg attttccgct ttccagcgtt   13980
cggcacgcag acgacgggct tcattctgca tggttgtgct taccagaccg gagatattga   14040
catcatatat gccttgagca actgatagct gtcgctgtca actgtcactg taatacgctg   14100
cttcatagca cacctctttt tgacatactt cgggtagtgc cgatcaacgt ctcattttcg   14160
ccaaaagttg gcccagggct tcccggtatc aacagggaca ccaggattta tttattctgc   14220
gaagtgatct tccgtcacag gtatttattc ggcgcaaagt gcgtcgggtg atgctgccaa   14280
cttagtcgac tacaggtcac taataccatc taagtagttg attcatagtg actggatatg   14340
ttgtgtttta cagtattatg tagtctgttt tttatgcaaa atctaattta atatattgat   14400
atttatatca ttttacgttt ctcgttcagc tttcttgtac aaagtggtct cgaggaattc   14460
ggtaccaact gtaaggaaat aattattttc ttttttcctt ttagtataaa atagttaagt   14520
gatgttaatt agtatgatta taataatata gttgttataa ttgtgaaaaa ataatttata   14580
aatatattgt ttacataaac aacatagtaa tgtaaaaaaa tatgacaagt gatgtgtaag   14640
acgaagaaga taaagttgaa gagtaagtat attattttta atgaatttga tcgaacatgt   14700
aagatgatat actagcatta atatttgttt taatcataat agtaattcta gctggtttga   14760
tgaattaaat atcaatgata aaatactata gtaaaaataa gaataaataa attaaaataa   14820
tattttttta tgattaatag tttattatat aattaaatat ctataccatt actaaatatt   14880
ttagtttaaa agttaataaa tattttgtta gaaattccaa tctgcttgta atttatcaat   14940
aaacaaaata ttaaataaca agctaaagta acaaataata tcaaactaat agaaacagta   15000
atctaatgta acaaaacata atctaatgct aatataacaa agcgcaagat ctatcatttt   15060
atatagtatt attttcaatc aacattctta ttaatttcta ataatacttt gtagtttat   15120 taacttctaa atggattgac tattaattaa atgaattagt cgaacatgaa taaacaaggt   15180
aacatgatag atcatgtcat tgtgttatca ttgatcttac atttggattg attacagtta   15240
cttaccttaa gcttggatcc tctagaccac tttgtacaag aaagctgaac gagaaacgta   15300
```

```
aaatgatata aatatcaata tattaaatta gattttgcat aaaaaacaga ctacataata    15360
ctgtaaaaca caacatatcc agtcactatg aatcaactac ttagatggta ttagtgacct    15420
gtagtcgact aagttggcag catcacccga cgcactttgc gccgaataaa tacctgtgac    15480
ggaagatcac ttcgcagaat aaataaatcc tggtgtccct gttgataccg ggaagccctg    15540
ggccaacttt tggcgaaaat gagacgttga tcggatttca caactcttat acttttctct    15600
tacaagtcgt tcggcttcat ctggattttc agcctctata cttactaaac gtgataaagt    15660
ttctgtaatt tctactgtat cgacctgcag actggctgtg tataagggag cctgacattt    15720
atattcccca gaacatcagg ttaatggcgt ttttgatgtc attttcgcgg tggctgagat    15780
cagccacttc ttccccgata acggagaccg gcacactggc catatcggtg gtcatcatgc    15840
gccagctttc atccccgata tgcaccaccg ggtaaagttc acgggagact ttatctgaca    15900
gcagacgtgc actggccagg gggatcacca tccgtcgccc gggcgtgtca ataatatcac    15960
tctgtacatc cacaaacaga cgataacggc tctctctttt ataggtgtaa accttaaact    16020
gcatttcacc agtccctgtt ctcgtcagca aaagagccgt tcatttcaat aaaccgggcg    16080
acctcagcca tcccttcctg attttccgct ttccagcgtt cggcacgcag acgacgggct    16140
tcattctgca tggttgtgct taccagaccg gagatattga catcatatat gccttgagca    16200
actgatagct gtcgctgtca actgtcactg taatacgctg cttcatagca cacctctttt    16260
tgacatactt ctgttcttga tgcagatgat tttcaggact atgacactag cgtatatgaa    16320
taggtagatg tttttatttt gtcacacaaa aaagaggctc gcacctcttt ttcttatttc    16380
tttttatgat ttaatacggc attgaggaca atagcgagta ggctggatac gacgattccg    16440
tttgagaaga acatttggaa ggctgtcggt cgactaagtt ggcagcatca cccgaagaac    16500
atttggaagg ctgtcggtcg actacaggtc actaatacca tctaagtagt tgattcatag    16560
tgactggata tgttgtgttt tacagtatta tgtagtctgt tttttatgca aaatctaatt    16620
taatatattg atatttatat cattttacgt ttctcgttca gctttttgt acaaacttgt     16680 ctagagtcct gctttaatga gatatgcgag acgcctatga tcgcatgata tttgctttca    16740
attctgttgt gcacgttgta aaaaacctga gcatgtgtag ctcagatcct taccgccggt    16800
ttcggttcat tctaatgaat atatcacccg ttactatcgt attttatga ataatattct      16860 ccgttcaatt tactgattgt accctactac ttatatgtac aatattaaaa tgaaaacaat    16920
atattgtgct gaataggttt atagcgacat ctatgataga gcgccacaat aacaaacaat    16980
tgcgttttat tattacaaat ccaatttaa aaaaagcggc agaaccggtc aaacctaaaa      17040
gactgattac ataaatctta ttcaaatttc aaaaggcccc agggctagt atctacgaca      17100 caccgagcgg cgaactaata acgttcactg aagggaactc cggttccccg ccggcgcgca    17160
tgggtgagat tccttgaagt tgagtattgg ccgtccgctc taccgaaagt tacgggcacc    17220
attcaacccg gtccagcacg gcggccgggt aaccgacttg ctgccccgag aattatgcag    17280
catttttttg gtgtatgtgg gccccaaatg aagtgcaggt caaaccttga cagtgacgac    17340
aaatcgttgg gcgggtccag ggcgaatttt gcgacaacat gtcgaggctc agcaggacct    17400
gcaggcatgc aagctagctt actagtgatg catattctat agtgtcacct aaatctgc      17458
```

<210> SEQ ID NO 26  
<211> LENGTH: 17681  
<212> TYPE: DNA  
<213> ORGANISM: Artificial sequence  
<220> FEATURE:  
<223> OTHER INFORMATION: acceptor vector pHELLSGATE12

<400> SEQUENCE: 26

```
ggccgcacta gtgatatccc gcggccatgg cggccgggag catgcgacgt cgggcccaat      60
tcgccctata gtgagtcgta ttacaattca ctggccgtcg ttttacaacg tcgtgactgg     120
gaaaaccctg gcgttaccca acttaatcgc cttgcagcac atccccottt cgccagctgg     180
cgtaatagcg aagaggcccg caccgatcgc ccttcccaac agttgcgcag cctgaatggc     240
gaatggaaat tgtaaacgtt aatgggtttc tggagtttaa tgagctaagc acatacgtca     300
gaaaccatta ttgcgcgttc aaaagtcgcc taaggtcact atcagctagc aaatatttct     360
tgtcaaaaat gctccactga cgttccataa attcccctcg gtatccaatt agagtctcat     420
attcactctc aatccaaata atctgcaatg gcaattacct tatccgcaac ttctttacct     480
atttccgccc ggatccgggc aggttctccg gccgcttggg tggagaggct attcggctat     540
gactgggcac aacagacaat cggctgctct gatgccgccg tgttccggct gtcagcgcag     600
gggcgcccgg ttcttttgt caagaccgac ctgtccggtg ccctgaatga actgcaggac     660
gaggcagcgc ggctatcgtg gctggccacg acgggcgttc cttgcgcagc tgtgctcgac     720
gttgtcactg aagcgggaag ggactggctg ctattgggcg aagtgccggg gcaggatctc     780
ctgtcatctc accttgctcc tgccgagaaa gtatccatca tggctgatgc aatgcggcgg     840
ctgcatacgc ttgatccggc tacctgccca ttcgaccacc aagcgaaaca tcgcatcgag     900
cgagcacgta ctcggatgga agccggtctt gtcgatcagg atgatctgga cgaagagcat     960
caggggctcg cgccagccga actgttcgcc aggctcaagg cgcgcatgcc cgacggcgag    1020
gatctcgtcg tgacccatgg cgatgcctgc ttgccgaata tcatggtgga aaatggccgc    1080
ttttctggat tcatcgactg tggccggctg ggtgtggcgg accgctatca ggacatagcg    1140
ttggctaccc gtgatattgc tgaagagctt ggcggcgaat gggctgaccg cttcctcgtg    1200
ctttacggta tcgccgctcc cgattcgcag cgcatcgcct tctatcgcct tcttgacgag    1260
ttcttctgag cgggactctg gggttcgaaa tgaccgacca agcgacgccc aacctgccat    1320
cacgagattt cgattccacc gccgccttct atgaaaggtt gggcttcgga atcgttttcc    1380
gggacgccgg ctggatgatc ctccagcgcg ggatctcat gctggagttc ttcgcccacc    1440
ccgatccaac acttacgttt gcaacgtcca agagcaaata gaccacgaac gccggaaggt    1500
tgccgcagcg tgtggattgc gtctcaattc tctcttgcag gaatgcaatg atgaatatga    1560
tactgactat gaaactttga gggaatactg cctagcaccg tcacctcata acgtgcatca    1620
tgcatgccct gacaacatgg aacatcgcta ttttttctgaa gaattatgct cgttggagga    1680
tgtcgcggca attgcagcta ttgccaacat cgaactaccc ctcacgcatg cattcatcaa    1740
tattattcat gcggggaaag gcaagattaa tccaactggc aaatcatcca gcgtgattgg    1800
taacttcagt tccagcgact tgattcgttt tggtgctacc cacgttttca ataaggacga    1860
gatggtggag taaagaagga gtgcgtcgaa gcagatcgtt caaacatttg gcaataaagt    1920
ttcttaagat tgaatcctgt tgccggtctt gcgatgatta tcatataatt tctgttgaat    1980
tacgttaagc atgtaataat taacatgtaa tgcatgacgt tatttatgag atgggttttt    2040
atgattagag tcccgcaatt atacatttaa tacgcgatag aaaacaaaat atagcgcgca    2100
aactaggata aattatcgcg cgcggtgtca tctatgttac tagatcgaat taattccagg    2160
cggtgaaggg caatcagctg ttgcccgtct cactggtgaa aagaaaaacc accccagtac    2220
attaaaaacg tccgcaatgt gttattaagt tgtctaagcg tcaatttgtt tacaccacaa    2280
tatatcctgc caccagccag ccaacagctc cccgaccggc agctcggcac aaaatcacca    2340
```

```
ctcgatacag gcagcccatc agtccgggac ggcgtcagcg ggagagccgt tgtaaggcgg    2400
cagactttgc tcatgttacc gatgctattc ggaagaacgg caactaagct gccgggtttg    2460
aaacacggat gatctcgcgg agggtagcat gttgattgta acgatgacag agcgttgctg    2520
cctgtgatca aatatcatct ccctcgcaga gatccgaatt atcagccttc ttattcattt    2580
ctcgcttaac cgtgacaggc tgtcgatctt gagaactatg ccgacataat aggaaatcgc    2640
tggataaagc cgctgaggaa gctgagtggc gctatttctt tagaagtgaa cgttgacgat    2700
gtcgacggat cttttccgct gcataaccct gcttcggggt cattatagcg attttttcgg    2760
tatatccatc cttttccgca cgatatacag gattttgcca aagggttcgt gtagactttc    2820
cttggtgtat ccaacggcgt cagccgggca ggataggtga agtaggccca cccgcgagcg    2880
ggtgttcctt cttcactgtc ccttattcgc acctggcggt gctcaacggg aatcctgctc    2940
tgcgaggctg ccggctacc gccggcgtaa cagatgaggg caagcggatg gctgatgaaa     3000
ccaagccaac caggggtgat gctgccaact tactgattta gtgtatgatg gtgttttga    3060 ggtgctccag tggcttctgt ttctatcagc tgtccctcct gttcagctac tgacggggtg    3120
gtgcgtaacg gcaaaagcac cgccggacat cagcgctatc tctgctctca ctgccgtaaa    3180
acatggcaac tgcagttcac ttacaccgct tctcaacccg gtacgcacca gaaaatcatt    3240
gatatggcca tgaatggcgt tggatgccgg gcaacagccc gcattatggg cgttggcctc    3300
aacacgattt tacgtcactt aaaaaactca ggccgcagtc ggtaacctcg cgcatacagc    3360
cgggcagtga cgtcatcgtc tgcgcggaaa tggacgaaca gtggggctat gtcgggcta    3420 aatcgcgcca gcgctggctg ttttacgcgt atgacagtct ccggaagacg gttgttgcgc    3480
acgtattcgg tgaacgcact atggcgacgc tggggcgtct tatgagcctg ctgtcaccct    3540
ttgacgtggt gatatggatg acggatggct ggccgctgta tgaatcccgc tgaagggaa     3600 agctgcacgt aatcagcaag cgatatacgc agcgaattga gcggcataac ctgaatctga    3660
ggcagcacct ggcacggctg ggacggaagt cgctgtcgtt ctcaaaatcg gtggagctgc    3720
atgacaaagt catcgggcat tatctgaaca taaaacacta tcaataagtt ggagtcatta    3780
cccaaccagg aagggcagcc cacctatcaa ggtgtactgc cttccagacg aacgaagagc    3840
gattgaggaa aaggcggcgg cggccggcat gagcctgtcg gcctacctgc tggccgtcgg    3900
ccagggctac aaaatcacgg gcgtcgtgga ctatgagcac gtccgcgagc tggcccgcat    3960
caatggcgac ctgggccgcc tgggcggcct gctgaaactc tggctcaccg acgacccgcg    4020
cacggcgcgg ttcggtgatg ccacgatcct cgccctgctg gcgaagatcg aagagaagca    4080
ggacgagctt ggcaaggtca tgatgggcgt ggtccgcccg agggcagagc catgactttt    4140
ttagccgcta aaacggccgg ggggtgcgcg tgattgccaa gcacgtcccc atgcgctcca    4200
tcaagaagag cgacttcgcg gagctggtat tcgtgcaggg caagattcgg aataccaagt    4260
acgagaagga cggccagacg gtctacggga ccgacttcat tgccgataag gtggattatc    4320
tggacaccaa ggcaccaggc gggtcaaatc aggaataagg gcacattgcc ccggcgtgag    4380
tcggggcaat cccgcaagga gggtgaatga atcggacgtt tgaccggaag gcatacaggc    4440
aagaactgat cgacgcgggg ttttccgccg aggatgccga aaccatcgca agccgcaccg    4500
tcatgcgtgc gccccgcgaa accttccagt ccgtcggctc gatggtccag caagctacgg    4560
ccaagatcga gcgcgacagc gtgcaactgg ctccccctgc cctgcccgcg ccatcggccg    4620
ccgtggagcg ttcgcgtcgt ctcgaacagg aggcggcagg tttggcgaag tcgatgacca    4680
tcgacacgcg aggaactatg acgaccaaga agcgaaaaac cgccggcgag gacctggcaa    4740
```

```
aacaggtcag cgaggccaag caggccgcgt tgctgaaaca cacgaagcag cagatcaagg   4800
aaatgcagct ttccttgttc gatattgcgc cgtggccgga cacgatgcga gcgatgccaa   4860
acgacacggc ccgctctgcc ctgttcacca cgcgcaacaa gaaaatcccg cgcgaggcgc   4920
tgcaaaacaa ggtcattttc cacgtcaaca aggacgtgaa gatcacctac accggcgtcg   4980
agctgcgggc cgacgatgac gaactggtgt ggcagcaggt gttggagtac gcgaagcgca   5040
cccctatcgg cgagccgatc accttcacgt tctacgagct tgccaggac ctgggctggt    5100 cgatcaatgg ccggtattac acgaaggccg aggaatgcct gtcgcgccta caggcgacgg   5160
cgatgggctt cacgtccgac cgcgttgggc acctggaatc ggtgtcgctg ctgcaccgct   5220
tccgcgtcct ggaccgtggc aagaaaacgt cccgttgcca ggtcctgatc gacgaggaaa   5280
tcgtcgtgct gtttgctggc gaccactaca cgaaattcat atgggagaag taccgcaagc   5340
tgtcgccgac ggcccgacgg atgttcgact atttcagctc gcaccgggag ccgtacccgc   5400
tcaagctgga aaccttccgc ctcatgtgcg gatcggattc cacccgcgtg aagaagtggc   5460
gcgagcaggt cggcgaagcc tgcgaagagt tgcgaggcag cggcctggtg aacacgcct    5520 gggtcaatga tgacctggtg cattgcaaac gctaggggcct tgtggggtca gttccggctg   5580
ggggttcagc agccagcgct ttactggcat ttcaggaaca agcgggcact gctcgacgca   5640
cttgcttcgc tcagtatcgc tcgggacgca cggcgcgctc tacgaactgc cgataaacag   5700
aggattaaaa ttgacaattg tgattaaggc tcagattcga cggcttggag cggccgacgt   5760
gcaggatttc cgcgagatcc gattgtcggc cctgaagaaa gctccagaga tgttcgggtc   5820
cgtttacgag cacgaggaga aaaagcccat ggaggcgttc gctgaacggt tgcgagatgc   5880
cgtggcattc ggcgcctaca tcgacggcga gatcattggg ctgtcggtct tcaaacagga   5940
ggacggcccc aaggacgctc acaaggcgca tctgtccggc gttttcgtgg agcccgaaca   6000
gcgaggccga ggggtcgccg gtatgctgct gcgggcgttg ccggcgggtt tattgctcgt   6060
gatgatcgtc cgacagattc caacgggaat ctggtggatg cgcatcttca tcctcggcgc   6120
acttaatatt tcgctattct ggagcttgtt gtttatttcg gtctaccgcc tgccgggcgg   6180
ggtcgcggcg acggtaggcg ctgtgcagcc gctgatggtc gtgttcatct ctgccgctct   6240
gctaggtagc ccgatacgat tgatggcggt cctgggggct atttgcggaa ctgcgggcgt   6300
ggcgctgttg gtgttgacac caaacgcagc gctagatcct gtcggcgtcg cagcgggcct   6360 ggcggggggcg gtttccatgg cgttcggaac cgtgctgacc cgcaagtggc aacctcccgt   6420
gcctctgctc acctttaccg cctggcaact ggcggccgga ggacttctgc tcgttccagt   6480
agctttagtg tttgatccgc caatcccgat gcctacagga accatgttc tcggcctggc    6540 gtggctcggc ctgatcggag cgggtttaac ctacttcctt tggttccggg ggatctcgcg   6600
actcgaacct acagttgttt ccttactggg ctttctcagc cgggatggcg ctaagaagct   6660
attgccgcca atcttcatat gcggtgtgaa ataccgcaca gatgcgtaag gagaaaatac   6720
cgcatcaggc gctcttccgc ttcctcgctc actgactcgc tgcgctcggt cgttcggctg   6780
cggcgagcgg tatcagctca ctcaaaggcg gtaatacggt tatccacaga atcagggggat   6840 aacgcaggaa agaacatgtg agcaaaaggc cagcaaaagg ccaggaaccg taaaaaggcc   6900
gcgttgctgg cgttttccca taggctccgc cccctgacg agcatcacaa aaatcgacgc   6960
tcaagtcaga ggtggcgaaa cccgacagga ctataaagat accaggcgtt tccccctgga   7020
agctccctcg tgcgctctcc tgttccgacc ctgccgctta ccggatacct gtccgccttt   7080
ctcccttcgg gaagcgtggc gctttctcaa tgctcacgct gtaggtatct cagttcggtg   7140
```

```
taggtcgttc gctccaagct gggctgtgtg cacgaacccc ccgttcagcc cgaccgctgc   7200
gccttatccg gtaactatcg tcttgagtcc aacccggtaa gacacgactt atcgccactg   7260
gcagcagcca ctggtaacag gattagcaga gcgaggtatg taggcggtgc tacagagttc   7320
ttgaagtggt ggcctaacta cggctacact agaaggacag tatttggtat ctgcgctctg   7380
ctgaagccag ttaccttcgg aaaaagagtt ggtagctctt gatccggcaa acaaaccacc   7440
gctggtagcg gtggtttttt tgtttgcaag cagcagatta cgcgcagaaa aaaggatat   7500 caagaagatc ctttgatctt ttctacgggg tctgacgctc agtggaacga aaactcacgt   7560
taagggattt tggtcatgag attatcaaaa aggatcttca cctagatcct tttaaattaa   7620
aaatgaagtt ttaaatcaat ctaaagtata tatgagtaaa cttggtctga cagttaccaa   7680
tgcttaatca gtgaggcacc tatctcagcg atctgtctat ttcgttcatc catagttgcc   7740 tgactcccg tcgtgtagat aactacgata cgggagggct taccatctgg ccccagtgct   7800
gcaatgatac cgcgagaccc acgctcaccg gctccagatt tatcagcaat aaaccagcca   7860
gccggaaggg ccgagcgcag aagtggtcct gcaactttat ccgcctccat ccagtctatt   7920
aaacaagtgg cagcaacgga ttcgcaaacc tgtcacgcct tttgtgccaa agccgcgcc   7980 aggtttgcga tccgctgtgc caggcgttag gcgtcatatg aagatttcgg tgatccctga   8040
gcaggtggcg gaaacattgg atgctgagaa ccatttcatt gttcgtgaag tgttcgatgt   8100
gcacctatcc gaccaaggct ttgaactatc taccagaagt gtgagcccct accggaagga   8160
ttacatctcg gatgatgact ctgatgaaga ctctgcttgc tatggcgcat tcatcgacca   8220
agagcttgtc gggaagattg aactcaactc aacatggaac gatctagcct ctatcgaaca   8280
cattgttgtg tcgcacacgc accgaggcaa aggagtcgcg cacagtctca tcgaatttgc   8340
gaaaaagtgg gcactaagca gacagctcct tggcatacga ttagagacac aaacgaacaa   8400
tgtacctgcc tgcaatttgt acgcaaaatg tggctttact ctcggcggca ttgacctgtt   8460
cacgtataaa actagacctc aagtctcgaa cgaaacagcg atgtactggt actggttctc   8520
gggagcacag gatgacgcct aacaattcat tcaagccgac accgcttcgc ggcgcggctt   8580
aattcaggag ttaaacatca tgagggaagc ggtgatcgcc gaagtatcga ctcaactatc   8640
agaggtagtt ggcgtcatcg agcgccatct cgaaccgacg ttgctggccg tacatttgta   8700
cggctccgca gtggatggcg gcctgaagcc acacagtgat attgatttgc tggttacggt   8760
gaccgtaagg cttgatgaaa caacgcggcg agctttgatc aacgaccttt tggaaacttc   8820
ggcttcccct ggagagagcg agattctccg cgctgtagaa gtcaccattg ttgtgcacga   8880
cgacatcatt ccgtggcgtt atccagctaa gcgcgaactg caatttggag aatggcagcg   8940
caatgacatt cttgcaggta tcttcagcc agccacgatc gacattgatc tggctatctt   9000
gctgacaaaa gcaagagaac atagcgttgc cttggtaggt ccagcggcgg aggaactctt   9060
tgatccggtt cctgaacagg atctatttga ggcgctaaat gaaaccttaa cgctatggaa   9120
ctcgccgccc gactgggctg gcgatgagcg aaatgtagtg cttacgttgt cccgcatttg   9180
gtacagcgca gtaaccggca aaatcgcgcc gaaggatgtc gctgccgact gggcaatgga   9240
gcgcctgccg gcccagtatc agcccgtcat acttgaagct aggcaggctt atcttggaca   9300
agaagatcgc ttggcctcgc gcgcagatca gttggaagaa tttgttcact acgtgaaagg   9360
cgagatcacc aaggtagtcg gcaaataatg tctaacaatt cgttcaagcc gacgccgctt   9420
cgcggcgcgc cttaactcaa gcgttagaga ctggggaag actatgcgcg atctgttgaa   9480
ggtggttcta agcctcgtac ttgcgatggc atcggggcag gcacttgctg acctgccaat   9540
```

```
tgttttagtg datgaagctc gtcttccta tgactactcc ccatccaact acgacatttc    9600
tccaagcaac tacgacaact ccataagcaa ttacgacaat agtccatcaa attacgacaa   9660
ctctgagagc aactacgata atagttcatc caattacgac aatagtcgca acggaaatcg   9720
taggcttata tatagcgcaa atgggtctcg cactttcgcc ggctactacg tcattgccaa   9780
caatgggaca cgaacttct tttccacatc tggcaaaagg atgttctaca ccccaaaagg    9840
ggggcgcggc gtctatggcg gcaaagatgg gagcttctgc ggggcattgg tcgtcataaa   9900
tggccaattt tcgcttgccc tgacagataa cggcctgaag atcatgtatc taagcaacta   9960
gcctgctctc taataaaatg ttaggagctt ggctgccatt tttggggtga ggccgttcgc  10020
ggccgagggg cgcagcccct gggggatgg gaggcccgcg ttagcgggcc gggagggttc   10080
gagaagggg ggcaccccc ttcggcgtgc gcggtcacgc gccagggcgc agccctggtt    10140
aaaaacaagg tttataaata ttggtttaaa agcaggttaa aagacaggtt agcggtggcc  10200
gaaaaacggg cggaaaccct tgcaaatgct ggatttctg cctgtggaca gccctcaaa    10260
tgtcaatagg tgcgcccctc atctgtcagc actctgcccc tcaagtgtca aggatcgcgc  10320
ccctcatctg tcagtagtcg cgcccctcaa gtgtcaatac cgcagggcac ttatccccag  10380
gcttgtccac atcatctgtg ggaaactcgc gtaaaatcag gcgttttcgc cgatttgcga  10440
ggctggccag ctccacgtcg ccggccgaaa tcgagcctgc ccctcatctg tcaacgccgc  10500
gccgggtgag tcggcccctc aagtgtcaac gtccgcccct catctgtcag tgagggccaa  10560
gttttccgcg aggtatccac aacgccggcg gccggccgcg gtgtctcgca cacggcttcg  10620
acggcgtttc tggcgcgttt gcagggccat agacggccgc cagcccagcg gcgagggcaa  10680
ccagcccggt gagcgtcgga aagggtcgac atcttgctgc gttcggatat tttcgtggag  10740
ttcccgccac agaccggat tgaaggcgag atccagcaac tcgcgccaga tcatcctgtg    10800
acggaacttt ggcgcgtgat gactggccag gacgtcggcc gaaagagcga caagcagatc  10860
acgattttcg acagcgtcgg atttgcgatc gaggattttt cggcgctgcg ctacgtccgc  10920
gaccgcgttg agggatcaag ccacagcagc ccactcgacc ttctagccga cccagacgag  10980
ccaagggatc tttttggaat gctgctccgt cgtcaggctt tccgacgttt gggtggttga  11040
acagaagtca ttatcgtacg gaatgccagc actcccgagg ggaaccctgt ggttggcatg  11100
cacatacaaa tggacgaacg gataaaacctt ttcacgcccct tttaaatatc cgttattcta  11160
ataaacgctc ttttctctta ggtttacccg ccaatatatc ctgtcaaaca ctgatagttt   11220
aaactgaagg cggaaacga caatctgatc atgagcggag aattaaggga gtcacgttat    11280
gaccccgcc gatgacgcgg gacaagccgt tttacgtttg gaactgacag aaccgcaacg    11340
attgaaggag ccactcagcc ccaatacgca aaccgcctct ccccgcgcgt tggccgattc    11400
attaatgcag ctggcacgac aggttttcccg actggaaagc gggcagtgag cgcaacgcaa    11460
ttaatgtgag ttagctcact cattaggcac cccaggcttt acactttatg cttccggctc   11520
gtatgttgtg tggaattgtg agcggataac aatttcacac aggaaacagc tatgaccatg   11580
attacgccaa gctatttagg tgacactata gaatactcaa gctatgcatc caacgcgttg   11640
ggagctctcc catatcgacc tgcaggcggc cgctcgacga attaattcca atcccacaaa   11700
aatctgagct taacagcaca gttgctcctc tcagagcaga atcgggtatt caacaccctc   11760
atatcaacta ctacgttgtg tataacggtc cacatgccgg tatatacgat gactgggtt    11820
gtacaaaggc ggcaacaaac ggcgttcccg gagttgcaca caagaaattt gccactatta  11880
cagaggcaag agcagcagct gacgcgtaca caacaagtca gcaaacagac aggttgaact   11940
```

```
tcatccccaa aggagaagct caactcaagc ccaagagctt tgctaaggcc ctaacaagcc    12000
caccaaagca aaaagcccac tggctcacgc taggaaccaa aaggcccagc agtgatccag    12060
ccccaaaaga gatctccttt gccccggaga ttacaatgga cgatttcctc tatctttacg    12120
atctaggaag gaagttcgaa ggtgaaggtg acgacactat gttcaccact gataatgaga    12180
aggttagcct cttcaatttc agaaagaatg ctgacccaca gatggttaga gaggcctacg    12240
cagcaggtct catcaagacg atctacccga gtaacaatct ccaggagatc aaataccttc    12300
ccaagaaggt taaagatgca gtcaaaagat tcaggactaa ttgcatcaag aacacagaga    12360
aagacatatt tctcaagatc agaagtacta ttccagtatg gacgattcaa ggcttgcttc    12420
ataaaccaag gcaagtaata gagattggag tctctaaaaa ggtagttcct actgaatcta    12480
aggccatgca tggagtctaa gattcaaatc gaggatctaa cagaactcgc cgtgaagact    12540
ggcgaacagt tcatacagag tcttttacga ctcaatgaca agaagaaaat cttcgtcaac    12600
atggtggagc acgacactct ggtctactcc aaaaatgtca agatacagt ctcagaagac    12660 caaagggcta ttgagacttt tcaacaaagg ataatttcgg gaaacctcct cggattccat    12720
tgcccagcta tctgtcactt catcgaaagg acagtagaaa aggaaggtgg ctcctacaaa    12780
tgccatcatt gcgataaagg aaaggctatc attcaagatc tctctgccga cagtggtccc    12840
aaagatggac ccccacccac gaggagcatc gtggaaaaag aagacgttcc aaccacgtct    12900
tcaaagcaag tggattgatg tgacatctcc actgacgtaa gggatgacgc acaatcccac    12960
tatccttcgc aagacccttc ctctatataa ggaagttcat ttcatttgga gaggacacgc    13020
tcgagacaag tttgtacaaa aaagctgaac gagaaacgta aatgatata aatatcaata    13080 tattaaatta gattttgcat aaaaaacaga ctacataata ctgtaaaaca caacatatcc    13140
agtcactatg aatcaactac ttagatggta ttagtgacct gtagtcgacc gacagccttc    13200
caaatgttct tcgggtgatg ctgccaactt agtcgaccga cagccttcca aatgttcttc    13260
tcaaacggaa tcgtcgtatc cagcctactc gctattgtcc tcaatgccgt attaaatcat    13320
aaaaagaaat aagaaaaaga ggtgcgagcc tcttttttgt gtgacaaaat aaaaacatct    13380
acctattcat atacgctagt gtcatagtcc tgaaaatcat ctgcatcaag aacaatttca    13440
caactcttat acttttctct tacaagtcgt tcggcttcat ctggattttc agcctctata    13500
cttactaaac gtgataaagt ttctgtaatt tctactgtat cgacctgcag actggctgtg    13560
tataagggag cctgacattt atattcccca gaacatcagg ttaatggcgt ttttgatgtc    13620
attttcgcgg tggctgagat cagccacttc ttccccgata acgagaccg gcacactggc    13680 catatcggtg gtcatcatgc gccagctttc atccccgata tgcaccaccg ggtaaagttc    13740
acgggagact ttatctgaca gcagacgtgc actggccagg gggatcacca tccgtcgccc    13800
gggcgtgtca ataatatcac tctgtacatc cacaaacaga cgataacggc tctctctttt    13860
ataggtgtaa accttaaact gcatttcacc agtccctgtt ctcgtcagca aaagagccgt    13920
tcatttcaat aaaccgggcg acctcagcca tcccttcctg attttccgct tccagcgtt    13980 cggcacgcag acgacgggct tcattctgca tggttgtgct taccagaccg gagatattga    14040
catcatatat gccttgagca actgatagct gtcgctgtca actgtcactg taatacgctg    14100
cttcatagca cacctctttt tgacatactt cgggtagtgc cgatcaacgt ctcattttcg    14160
ccaaaagttg gcccagggct tcccggtatc aacagggaca ccaggattta tttattctgc    14220
gaagtgatct tccgtcacag gtatttattc ggcgcaaagt gcgtcgggtg atgctgccaa    14280
cttagtcgac tacaggtcac taataccatc taagtagttg attcatagtg actggatatg    14340
```

```
ttgtgtttta cagtattatg tagtctgttt tttatgcaaa atctaattta atatattgat    14400
atttatatca ttttacgttt ctcgttcagc tttcttgtac aaagtggtct cgaggaattc    14460
ggtaccccag cttggtaagg aaataattat tttcttttt cctttagta taaaatagtt     14520 aagtgatgtt aattagtatg attataataa tatagttgtt ataattgtga aaaataatt    14580 tataaatata ttgtttacat aaacaacata gtaatgtaaa aaaatatgac aagtgatgtg    14640
taagacgaag aagataaaag ttgagagtaa gtatattatt tttaatgaat ttgatcgaac    14700
atgtaagatg atatactagc attaatattt gttttaatca taatagtaat tctagctggt    14760
ttgatgaatt aaatatcaat gataaaatac tatagtaaaa ataagaataa ataaattaaa    14820
ataatatttt tttatgatta atagtttatt ataattaa atatctatac cattactaaa     14880
tattttagtt taaaagttaa taaatatttt gttagaaatt ccaatctgct tgtaatttat    14940
caataaacaa aatattaaat aacaagctaa agtaacaaat aatatcaaac taatagaaac    15000
agtaatctaa tgtaacaaaa cataatctaa tgctaatata acaaagcgca agatctatca    15060
ttttatatag tattattttc aatcaacatt cttattaatt tctaaataat acttgtagtt    15120
ttattaactt ctaaatggat tgactattaa ttaaatgaat tagtcgaaca tgaataaaca    15180
aggtaacatg atagatcatg tcattgtgtt atcattgatc ttacatttgg attgattaca    15240
gttgggaagc tgggttcgaa atcgataagc ttgcgctgca gttatcatca tcatcataga    15300
cacacgaaat aaagtaatca gattatcagt taaagctatg taatatttgc gccataacca    15360
atcaattaaa aaatagatca gtttaaagaa agatcaaagc tcaaaaaaat aaaaagagaa    15420
aagggtccta accaagaaaa tgaaggagaa aaactagaaa tttacctgca caagcttgga    15480
tcctctagac cactttgtac aagaaagctg aacgagaaac gtaaaatgat ataaatatca    15540
atatattaaa ttagattttg cataaaaaac agactacata atactgtaaa acacaacata    15600
tccagtcact atgaatcaac tacttagatg gtattagtga cctgtagtcg actaagttgg    15660
cagcatcacc cgacgcactt tgcgccgaat aaatacctgt gacggaagat cacttcgcag    15720
aataaataaa tcctggtgtc cctgttgata ccgggaagcc ctgggccaac ttttggcgaa    15780
aatgagacgt tgatcggatt tcacaactct tatactttc tcttacaagt cgttcggctt     15840
catctggatt ttcagcctct atacttacta aacgtgataa agtttctgta atttctactg    15900
tatcgacctg cagactggct gtgtataagg gagcctgaca tttatattcc ccagaacatc    15960
aggttaatgg cgtttttgat gtcattttcg cggtggctga gatcagccac ttcttccccg    16020
ataacggaga ccggcacact ggccatatcg gtggtcatca tgcgccagct tcatccccg     16080 atatgcacca ccgggtaaag ttcacgggag actttatctg acagcagacg tgcactggcc    16140 aggggggatca ccatccgtcg cccgggcgtg tcaataatat cactctgtac atccacaaac   16200
agacgataac ggctctctct tttataggtg taaaccttaa actgcatttc accagtccct    16260
gttctcgtca gcaaaagagc cgttcatttc aataaaccgg cgacctcag ccatcccttc     16320 ctgatttcc gctttccagc gttcggcacg cagacgacgg gcttcattct gcatggttgt     16380
gcttaccaga ccggagatat tgacatcata tatgccttga gcaactgata gctgtcgctg    16440
tcaactgtca ctgtaatacg ctgcttcata gcacacctct ttttgacata cttctgttct    16500
tgatgcagat gattttcagg actatgacac tagcgtatat gaataggtag atgtttttat    16560
tttgtcacac aaaaaagagg ctcgcacctc tttttcttat ttcttttat gatttaatac     16620 ggcattgagg acaatagcga gtaggctgga tacgacgatt ccgtttgaga agaacatttg    16680
gaaggctgtc ggtcgactaa gttggcagca tcacccgaag aacatttgga aggctgtcgg    16740
```

-continued

```
tcgactacag gtcactaata ccatctaagt agttgattca tagtgactgg atatgttgtg    16800
ttttacagta ttatgtagtc tgtttttttat gcaaaatcta atttaatata ttgatattta   16860
tatcatttta cgtttctcgt tcagcttttt tgtacaaact tgtctagagt cctgctttaa    16920
tgagatatgc gagacgccta tgatcgcatg atatttgctt tcaattctgt tgtgcacgtt    16980
gtaaaaaacc tgagcatgtg tagctcagat ccttaccgcc ggtttcggtt cattctaatg    17040
aatatatcac ccgttactat cgtatttta tgaataatat tctccgttca atttactgat     17100
tgtaccctac tacttatatg tacaatatta aaatgaaaac aatatattgt gctgaatagg    17160
tttatagcga catctatgat agagcgccac aataacaaac aattgcgttt tattattaca    17220
aatccaattt taaaaaaagc ggcagaaccg gtcaaaccta aaagactgat tacataaatc    17280
ttattcaaat ttcaaaaggc cccaggggct agtatctacg acacaccgag cggcgaacta    17340
ataacgttca ctgaagggaa ctccggttcc ccgccggcgc gcatgggtga gattccttga    17400
agttgagtat tggccgtccg ctctaccgaa agttacgggc accattcaac ccggtccagc    17460
acggcggccg ggtaaccgac ttgctgcccc gagaattatg cagcattttt ttggtgtatg    17520
tgggccccaa atgaagtgca ggtcaaacct tgacagtgac gacaaatcgt tgggcgggtc    17580
cagggcgaat tttgcgacaa catgtcgagg ctcagcagga cctgcaggca tgcaagctag    17640
cttactagtg atgcatattc tatagtgtca cctaaatctg c                       17681
```